United States Patent [19]

Jasserand et al.

[11] Patent Number: 5,324,725

[45] Date of Patent: Jun. 28, 1994

[54] 7-FUSED 2-(PIPERAZINOALKYL) INDOLE DERIVATIVES, INTERMEDIATES AND COMPOSITIONS THEREOF

[75] Inventors: Daniel Jasserand, Lyons; Dominique Paris, Amberieux en Dombes; Patrice Demonchaux; Michel Cottin, both of Chatillon sur Chalaronne; Francois Floc'H, Limonest; Pierre Dupassieux, Chatillon sur Chalaronne; Richard White, Bourg en Bresse, all of France

[73] Assignee: Kali-Chemie Pharma GmbH, Hanover, Fed. Rep. of Germany

[21] Appl. No.: 933,476

[22] Filed: Aug. 21, 1992

[30] Foreign Application Priority Data

Aug. 23, 1991 [DE] Fed. Rep. of Germany ....... 4128015

[51] Int. Cl.$^5$ .................. C07D 471/06; C07D 487/06; A61K 31/435; A61K 31/55
[52] U.S. Cl. .................................. 514/214; 514/253; 514/294; 514/323; 540/581; 544/32; 544/101; 544/361; 544/372; 546/94; 546/200; 548/428
[58] Field of Search ................ 540/581; 544/361, 372; 546/94, 200; 514/214, 253, 294, 323

[56] References Cited

U.S. PATENT DOCUMENTS 3,468,882 9/1969 Laskowski .......................... 260/240
5,010,076 4/1991 Waldeck et al. .................... 514/221

FOREIGN PATENT DOCUMENTS 322016 6/1989 European Pat. Off. .
384349 8/1990 European Pat. Off. .
387618 9/1990 European Pat. Off. .

OTHER PUBLICATIONS

McKittrick et al., "Synthetic entries to 6-fluoro-7-substituted indole derivatives", *Heterocyclic Chem.*, 27:2151–63 (1990).
Steck et al., "some 5,6-dihydro-4H-pyrrolo [3,2,1-ij]-quinolines", *Heterocyclic Chem.*, 387–93 (1974).
*Chemical Abstracts*, vol. 54, Abstract No. 21091f-i (1960), Kost et al.
*Chemical Abstracts*, vol. 58, Abstract No. 4511g-h (1963), Kost et al.

Primary Examiner—Mukund J. Shah
Assistant Examiner—Philip I. Datlow
Attorney, Agent, or Firm—Evenson, McKeown, Edwards & Lenahan

[57] ABSTRACT

Pharmacologically active compounds having anti-allergic properties corresponding to the formula I

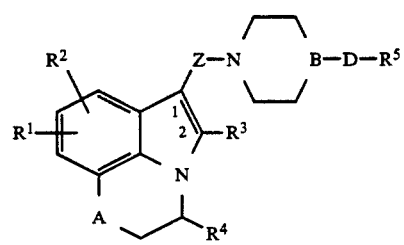

which can be mono- or disubstituted in the phenyl ring and their acid addition salts and/or S-mono- or dioxides of sulfur-containing compounds of the formula I are described, together with processes and intermediates for their preparation.

10 Claims, No Drawings

7-FUSED 2-(PIPERAZINOALKYL) INDOLE DERIVATIVES, INTERMEDIATES AND COMPOSITIONS THEREOF

BACKGROUND OF THE INVENTION

The present invention relates to novel 1,7-fused indole derivatives carrying a substituted piperazinoalkyl radical in the 3-position of the indole ring and salts thereof and to pharmaceutical preparations containing these compounds and to processes and intermediates for preparing these compounds.

Published European Patent Application No. EP 322,016 discloses esters and amides of 1,7-fused indole-2-carboxylic acid derivatives and cyclic alcohols or amines, which are selective antagonists of neuronal 5-HT receptors and are suitable for treating complaints induced by overstimulation of these receptors, for example in the gastrointestinal region.

Published European Patent Application No. EP 387,618 discloses amides of 1,7-fused indole-2-carboxylic acid derivatives with 3-amino-1,4-benzodiazepine derivatives. These compounds have CCK-antagonistic effects with an activity component promoting gastric emptying.

SUMMARY OF THE INVENTION

It is the object of the present invention to provide novel pharmaceutical active substances which can be employed as anti-allergics.

It is also an object of the invention to provide novel derivatives of b 1,7-fused indole compounds having useful pharmacological properties Another object of the invention is to provide new intermediate compounds and processes for preparing pharmacologically active 1,7-fused 2-(piperazinoalkyl)indole compounds.

It has now been found that the novel 1,7-fused 2-(piperazinoalkyl)indole derivatives according to the invention have useful pharmacological properties and exhibit anti-inflammatory and anti-allergic effects and have an advantageous activity profile with low toxicity and good tolerance. By virtue of their activity profile, the compounds of the invention are suitable as anti-inflammatory active substances and anti-allergics for the treatment of inflammatory and allergic diseases.

DETAILED DESCRIPTION OF THE INVENTION

The present invention therefore relates to novel compounds of the general formula I

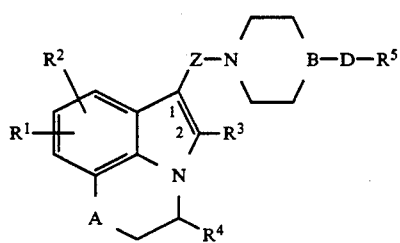

in which $R^1$ denotes hydrogen, lower alkoxy, lower alkylthio, hydroxyl, halogen, trifluoromethyl, nitro, amino, lower mono- or dialkylamino, $C_1$–$C_7$-alkyl which can optionally be substituted by hydroxyl, or denotes a phenyl-lower alkyl group which can optionally be substituted in the phenyl ring by lower alkyl, lower alkoxy, hydroxyl or halogen, or denotes $C_3$–$C_6$-cycloalkyl, $C_4$–$C_7$-cycloalkylalkyl, $C_3$–$C_7$-alkenyl, $C_2$–$C_7$-alkanoyl, lower alkanoyloxy, lower alkanoylamino, a benzoyl, benzoyloxy or benzoylamino group whose phenyl ring can optionally be substituted by lower alkyl, lower alkoxy, hydroxyl or halogen, or denotes a cinnamoyl, cinnamoyloxy or cinnamoylamino group whose phenyl ring can optionally be substituted by lower alkyl, lower alkoxy, hydroxyl or halogen;

$R^2$ denotes hydrogen, halogen, lower alkyl or, if $R^1$ is not hydroxyl or a hydroxyphenyl-containing group, also denotes lower alkoxy, $R^3$ denotes hydrogen, lower alkyl which is optionally substituted by hydroxyl, or denotes lower alkenyl, $C_3$–$C_6$-cycloalkyl, $C_4$–$C_7$-cycloalkylalkyl or a phenyl or phenyl-lower alkyl group, which can optionally be substituted in the phenyl ring by lower alkyl, halogen, lower alkoxy, hydroxyl or hydroxyalkoxy, but where $R^3$ can only contain a free hydroxyl group if R: does not contain a carbonyloxy group;

$R^4$ denotes hydrogen, $C_1$–$C_7$-alkyl which can optionally be substituted by hydroxyl, or denotes $C_3$–$C_7$-alkenyl, $C_3$–$C_6$-cycloalkyl, $C_4$–$C_7$-cycloalkylalkyl or a phenyl or phenyl-lower alkyl group which can optionally be substituted in the phenyl ring by lower alkyl, halogen, lower alkoxy, hydroxyl or hydroxyalkoxy, but where $R^4$ can only contain a free hydroxyl group if $R^1$ does not contain a carbonyloxy group;

A denotes an alkylene chain having 1-2 carbon atoms, which is optionally substituted by lower alkyl, or denotes a bond, oxygen or sulfur;

Z denotes an alkylene chain having 2-4 carbon atoms, which can optionally be substituted by lower alkyl or, if $R^1$ does not contain a carbonyloxy group, also by hydroxyl;

B denotes nitrogen or the CH group;

$R^5$ denotes a pyridyl or phenyl radical which is optionally substituted by lower alkyl, lower alkoxy or halogen, and D represents a bond or, if B denotes the CH group and $R^5$ denotes an optionally substituted phenyl radical, D can also represent the CO group, and their acid addition salts and/or S-mono- or dioxides of sulfur-containing compounds of the formula I.

If, in the compounds of the formula I, the substituents denote or contain lower alkyl groups, these alkyl groups can be straight-chain or branched and in particular contain 1–4, preferably or 2, carbon atoms and are most preferably methyl. If the substituents denote halogen or contain halogen substituents, fluorine, chlorine or bromine is preferred, particularly chlorine The substituent $R^1$ may denote hydrogen. Advantageous substitutents also include alkyl groups optionally substituted by hydroxyl and having 1–7, preferably 1–6 carbon atoms, in particular lower alkyl groups, for example methyl, an alkenyl group having up to 7, in particular up to 4 carbon atoms, halogen, hydroxyl, a lower alkoxy group, in particular methoxy, and acyl, acyloxy and acylamino radicals which contain alkanoyl having 2–7, preferably 2–5 carbon atoms, optionally substituted benzoyl or optionally substituted cinnamoyl, in particular radicals containing lower alkanoyl or benzoyl. Phenyl rings contained in the substituent $R^1$ are preferably unsubstituted, but can also be mono- or disubstituted by lower alkyl, in particular methyl, lower alkoxy, in particular methoxy, hydroxyl or halogen, in particular chlorine. A substituent $R^1$ may advantageously be located in the 5- or 4-position of the indole structure.

The substituent $R^2$ preferably represents hydrogen or may also denote halogen, in particular chlorine, lower alkyl, in particular methyl, or lower alkoxy, in particular methoxy.

The substituent $R^3$ may denote hydrogen, an aliphatic hydrocarbon radical such as lower alkyl or alkenyl or cyclic alkyl having up to 7 carbon atoms, where an alkyl radical can optionally be substituted by hydroxyl, or $R^3$ may also denote phenyl or phenyl-lower alkyl which is optionally substituted in the phenyl ring Advantageous groups include lower alkyl groups $R^3$, in particular methyl. Phenyl groups contained in the radical $R^3$ can be unsubstituted or mono- or disubstituted by the abovementioned radicals. Suitable substituents of the phenyl group include, for example, lower alkoxy, in particular methoxy, or else hydroxyl.

The substituent $R^4$ may denote hydrogen or an aliphatic hydrocarbon radical having up to 7 carbon atoms such as straight-chain, branched or cyclic alkyl or alkenyl, where an alkyl radical can optionally be substituted by hydroxyl, or $R^4$ may represent a phenyl or phenyl-lower alkyl group which is optionally substituted in the phenyl ring. An advantageous group is, for example, alkyl containing up to 7 carbon atoms.

A may denote an alkylene chain having 1-2 carbon atoms, which is optionally substituted by lower alkyl, or A may denote a bond or else oxygen or sulfur. Advantageous compounds include, for example, 5,6-dihydro-4H-pyrrolo[3,2,1-ij]quinoline derivatives of the formula I, i.e. compounds in which A represents a methylene group which is optionally substituted by lower alkyl.

Z represents an alkylene chain having 2-4, in particular 2 or 3, carbon atoms, which is optionally substituted by lower alkyl or hydroxyl. One suitable group, for example, is an unsubstituted ethylene chain or else an ethylene chain optionally substituted by lower alkyl or hydroxyl.

If the substituent $R^5$ represents a pyridyl radical, this can be unsubstituted or substituted by lower alkyl, lower alkoxy or halogen. For example, suitable pyridyl radicals include pyridyl radicals substituted by lower alkyl, particularly methyl, or unsubstituted pyridyl radicals. Preferably, a suitable group is a pyridin-2-yl group which can optionally be substituted. One particularly advantageous radical is the 4-methylpyridin-2-yl radical If $R^5$ denotes a phenyl radical, this can be unsubstituted or mono- or disubstituted by halogen, lower alkyl, in particular methyl, or lower alkoxy, in particular methoxy. If $R^5$ represents an optionally substituted phenyl radical, D preferably represents the CO group.

According to the invention, the novel compounds of the formula I and their acid addition salts and/or S-mono- or -dioxides of sulfur-containing compound of the formula I are obtained by a process in which, in a known manner a) to prepare compounds of the general formula Ia

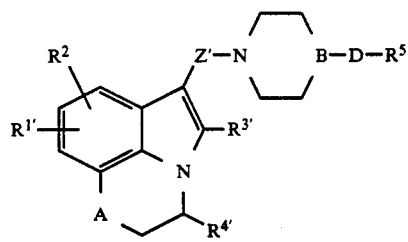

in which $R^1$ has the meaning given for $R^1$ with the exception of hydroxyl-substituted $C_1$-$C_7$-alkyl or mono- or di-lower alkylamino, $R^3$ and $R^4$ denote the radicals given for $R^3$ and $R^4$ with the exception of radicals containing lower hydroxyalkyl groups, $Z'$ has the meaning given for Z, but where the alkylene chain $Z'$ can contain a possible hydroxyl substituent only in the position adjacent to the indole structure, and $R^2$, $R^5$, A, B and D have the above meanings, compounds of the general formula II

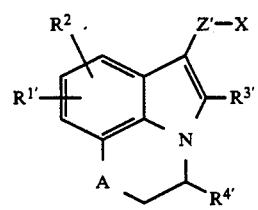

in which $R^1$ $R^2$, $R^3$, $R^4$, A and $Z'$ have the above meanings and X represents a leaving group which can be eliminated by aminolysis, are reacted with compounds of the general formula III

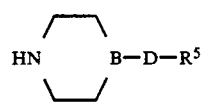

in which B, D and $R^5$ have the above meanings, or
b) to prepare compounds of the general formula Ib

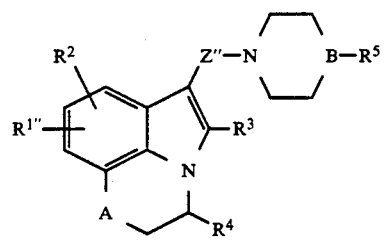

in which $R^2$, $R^3$, $R^4$, A, B and $R^5$ have the above meanings, $R^{1''}$ represents the radicals given for $R^1$ with the exception of CO-containing radicals, and $Z''$ represents a $-Z'''-CH_2$ chain, in which $Z'''$ denotes an alkylene chain having 1-3 carbon atoms, which can optionally be substituted by lower alkyl or also by hydroxyl, or, if $R^1$, $R^3$ and/or $R^4$ denote a radical containing a hydroxyalkyl or $R^1$ denotes a mono- or di-lower alkylamino group, $Z''$ also can have the meaning given for $Z'$, compounds of the general formula IV

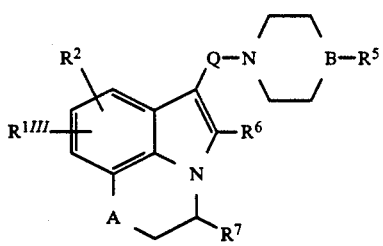

in which $R^2$, $R^5$, A and B have the above meanings, $R^{1III}$ denotes the radicals given for $R^1$ with the exception of radicals containing the COO group, the —CONH group or radicals containing a hydroxyalkyl group or denotes an N-formyl-substituted or N-lower alkanoyl-substituted amino or lower alkylamino group, $R^6$ has the meaning given for $R^3$ or denotes a lower alkoxycarbonyl or lower alkoxycarbonyl-lower alkyl group or a phenyl or phenyl-lower alkyl group substituted in the phenyl ring by lower alkoxycarbonyl-lower alkoxy, $R^7$ has the meaning given for $R^4$ or denotes a lower alkoxycarbonyl or lower alkoxycarbonyl-lower alkyl group or a phenyl or phenyl-lower alkyl group substituted in the phenyl ring by lower alkoxycarbonyl-lower alkoxy, and Q represents a —Q'—CO chain, in which Q' represents an alkylene chain having 1-3 carbon atoms, which can optionally be substituted by lower alkyl or by oxo, or Q denotes a substituted alkylene chain having 2-4 carbon atoms, which is substituted in the position adjacent to the indole structure by oxo and which can optionally be substituted by lower alkyl, or, if $R^{1III}$, $R^6$ and/or $R^7$ denote a CO-containing radical, Q also can have the meaning given for Z', are reduced, or c) to prepare compounds of the general formula Ic

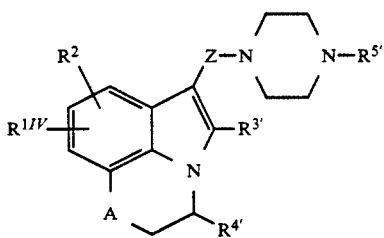

in which $R^2$, $R^3$, $R^4$, A and Z have the above meanings, $R^5$ represents a pyridyl radical which is optionally substituted by lower alkyl, lower alkoxy or halogen and $R^{1IV}$ has the meaning given for $R^1$ with the exception of hydroxyl-substituted $C_1$-$C_7$-alkyl, compounds of the general formula V

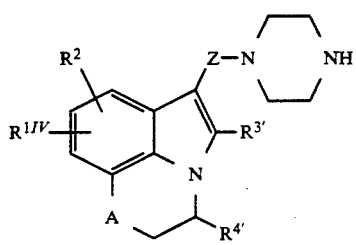

in which $R^{1IV}$, $R^2$, $R^3$, $R^4$, A and Z have the above meanings, are reacted with a compound of the formula VI $$X'—R^5 \qquad \text{VI}$$

in which $R^5$ has the above meaning and X' denotes halogen, or d) to prepare compounds of the general formula Id

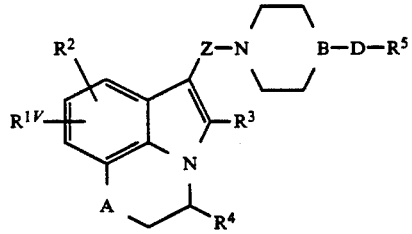

in which $R^2$, $R^3$, $R^4$, A, Z, B, D and $R^5$ have the above meanings and $R^{IV}$ denotes $C_2$-$C_7$-alkanoyl, lower alkanoyloxy, lower alkanoylamino, a benzoyl, benzoyloxy or benzoylamino group whose phenyl ring can optionally be substituted by lower alkyl, lower alkoxy, hydroxyl or halogen, or denotes a cinnamoyl, cinnamoyloxy or cinnamoylamino group whose phenyl ring can optionally be substituted by lower alkyl, lower alkoxy, hydroxyl or halogen, compounds of the formula Ie

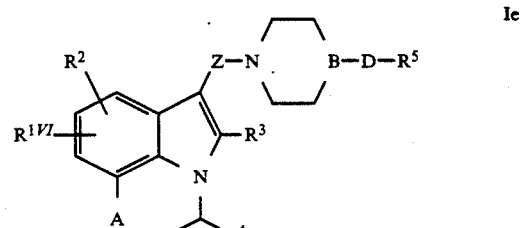

in which $R^2$, $R^3$, $R^4$, A, Z, B, D and $R^5$ have the above meanings and $R^{1VI}$ denotes hydrogen, amino or, if $R^3$, $R^4$ and/or Z do not contain any free hydroxyl groups, also denotes hydroxyl, are acylated with acids or reactive acid derivatives of the general formula VII $$R^8—Y \qquad \text{VII}$$

in which $R^8$ denotes $C_2$-$C_7$-alkanoyl, a benzoyl group whose phenyl ring can optionally be substituted by lower alkyl, lower alkoxy, hydroxyl or halogen, or denotes a cinnamoyl group whose phenyl ring can optionally be substituted by lower alkyl, lower alkoxy, hydroxyl or halogen, and Y denotes hydroxyl or a reactive group, and, if desired, in compounds of the formula I obtained, in which $R^1$ denotes methoxy or contains a methoxyphenyl group and/or $R^3$ and/or $R^4$ represent or contain a methoxyphenyl group, the methoxy group is cleaved to give the hydroxyl group, and/or in compounds of the formula I in which $R^1$, $R^3$ and/or $R^4$ contain a hydroxyalkyl group having at least 2 carbon atoms, this group is converted by elimination of water into a corresponding alkenyl group, or in compounds of the formula I in which only $R^1$ contains a hydroxyalkyl group, this group is oxidized to the corresponding alkanoyl group, and/or compounds of the formula I in which $R^1$ denotes amino are alkylated to give corresponding compounds of the formula I in which $R^1$ denotes lower mono- or dialkylamino, and/or sulfur-containing compounds of the formula I are converted into the corresponding S-mono- or -dioxides and, if desired, free compounds of the formula I are converted into their acid addition salts or the acid addition salts are converted into the free compounds of the formula I.

The reaction of compounds of the formula II with compounds of the formula III according to process variant a) can be carried out by customary methods for the alkylation of amines. The reaction is advantageously carried out under basic conditions in an organic solvent which is inert under the reaction conditions.

Suitable radicals X in the compounds of the formula II which can be eliminated by aminolysis include halogens such as chlorine, bromine or iodine, preferably bromine, or alternatively an acyloxy radical O—E, in which E represents a lower alkanoyl radical or an organic sulfonic acid radical, for example the radical of a lower alkanesulfonic acid, such as, for example, methanesulfonic acid, or of aromatic sulfonic acids, such as benzenesulfonic acid or benzenesulfonic acids substituted by lower alkyl or by halogen, for example toluenesulfonic acids or bromobenzenesulfonic acids. If compounds of the formula II contain free hydroxyl groups in the radicals $R^1$, $R^3$ and/or $R^4$, X preferably represents halogen. Suitable inert organic solvents include aprotic solvents, for example aromatic hydrocarbons such as toluene, xylene or benzene, cyclic ethers such as dioxane, dimethylformamide, lower alkanols such as ethanol or mixtures of the abovementioned solvents. Advantageously, the reaction is carried out at elevated temperatures, for example temperatures between 50 and 150° C. The reaction is also advantageously carried out with addition of an organic or inorganic base. However, an excess of the compound of formula III can also be used and this can be utilized as an internal base. Examples of suitable organic bases include tertiary organic amines, in particular tertiary lower alkylamines such as triethylamine, tripropylamines, N-lower alkylmorpholines or N-lower alkylpiperidines. Suitable inorganic bases include in particular alkali metal carbonates or bicarbonates. If desired, the reaction can be promoted by addition of a catalytically active amount of potassium iodide. Depending on the reaction conditions, the reaction time can be between 1 and 15 hours. During the reaction of the compounds of formula II with the piperazines of formula III, free amino groups $R^1$ must be protected in a known manner by protective groups which can easily be removed again. If desired, free phenolic hydroxyl groups can also be protected during the reaction by a protective group which can subsequently be easily removed again. Protective groups which can be selected are known protective groups which can be removed again in a known manner by solvolysis or hydrogenolysis. Suitable protective groups for amino groups and for phenolic OH groups which can easily be removed again are known, for example, from E. McOmie "Protective Groups in Organic Chemistry" Plenum Press 1971. For example, a suitable group for protecting an amino or lower alkyl amino group is the formyl or the acetyl group, which can be removed again by hydrolysis after completion of the reaction. Protective groups which can be selected for a possible phenolic hydroxyl group include known ether-protective groups which can be removed again by solvolysis or hydrogenolysis in a known manner, for example lower alkyl or benzyl groups. Of course, in selecting protective groups, the other radicals contained in the compound to be protected must be taken into account so that the protective groups can be easily removed using conditions under which other radicals present in the molecule are not attacked.

The reduction of compounds of the formula IV according to process variant b) can be carried out by customary methods for the reduction of amides and/or for the reduction of alkoxycarbonyl groups. Suitable reducing agents include complex metal hydrides. Thus, for example, to reduce amides of formula IV (Q=Q'—CO and/or $R^{1III}$=acylamino) complex metal hydrides capable of amide reduction, in particular aluminum hydrides such as lithium aluminum hydride or sodium (2-methoxyethoxy)dihydroaluminate, or else lithium borohydride or diborane are suitable. The reaction should be carried out in a sufficiently anhydrous solvent which is inert under the reaction conditions. Suitable solvents include, for example, cyclic ethers such as tetrahydrofuran or dioxane or open-chain ethers such as diethyl ether, ethylene glycol dimethyl ether or diethylene glycol dimethyl ether, optionally mixed with aromatic hydrocarbons such as benzene or toluene —CO groups contained in the radical $R^{1III}$ or the chain Q' are reduced under the reaction conditions to the corresponding —CH—OH groups. Depending on the reaction temperature and the type and amount of the reducing agent employed, a CO group of the Q' chain adjacent the CO group can also be completely reduced to the —CH$_2$ group, particularly when using lithium aluminum hydride or diborane, or mixtures of completely reduced compounds and compounds in which the CO group of the Q' chain has been reduced to the —CH—OH group can be obtained Mixtures of this type can be separated by customary methods, for example by chromatography. If the compounds of formula IV do not contain any amide function, i.e. only lower alkoxycarbonyl groups in the radicals $R^6$ or $R^7$, or a CO group in the radical $R^{1III}$ and/or a CO group of the chain Q adjacent to the indole structure are to be reduced to the hydroxymethyl group, besides the abovementioned complex metal hydrides, di-lower alkyl- aluminum hydrides such as dibutylaluminum hydride or else di-lower alkylborohydrides or sodium borohydride are also suitable as reducing agents.

Depending on the type of reducing agent used and the function to be reduced the reaction temperature can vary between 0° C. and the boiling temperature of the reaction mixture. Reaction with lithium aluminum hydride at the boiling temperature of the reaction mixture is suitable, for example, for reducing an amide function. The reaction time can be between 1 and 10 hours.

The reaction of compounds of the formula V with compounds of the formula VI according to process variant c) can be carried out by customary methods for the alkylation of amines. They can be carried out, for example, in the manner described for the reaction of the compounds of formula II with the compounds of formula III. Free amino or lower alkylamino groups $R^{1IV}$ must be protected during the reaction in a known manner by protective groups which can subsequently be removed again.

The acylation of compounds of formula Ie according to process variant d) can be carried out by known methods. Acids of the formula VIIa $$R^8\text{—OH} \qquad \qquad \text{VIIa}$$

in which $R^8$ has the above meaning, or their reactive acid derivatives, can be employed as acylating agents.

Suitable reactive derivatives are in particular acid halides, optionally mixed acid anhydrides and esters. Thus, reactive groups Y may represent, for example, halogens such as chlorine or bromine, lower alkoxy, or acyloxy radicals such as lower alkanoyloxy, the $R^8$—O— radical or organic sulfonic acid radicals, for example radicals of lower alkanesulfonic acid, such as, for example, methanesulfonic acid or of aromatic sulfonic acids such as benzenesulfonic acid or benzenesulfonic acids substituted by lower alkyl or halogen.

The acylation of such compounds of the formula Ie, in which $R^{1VI}$ denotes amino or hydroxyl, can be carried out b customary methods for the formation of ester or amide groups by acylation of aromatic amines or phenols. Thus, the acylation can advantageously be carried out in a solvent which is inert under the reaction conditions at temperatures between room temperature and the boiling point of the solvent. Suitable solvents include halogenated hydrocarbons such as dichloromethane, chloroform, dichloroethane or carbon tetrachloride, aromatic hydrocarbons such as benzene, toluene, xylene or chlorobenzene, cyclic ethers such as tetrahydrofuran or dioxane, dimethylformamide or mixtures of these solvents. The acylation can optionally be carried out, in particular if an acid halide or anhydride of the formula VII is used, in the presence of an acid-binding reagent. Suitable acid-binding agents include organic or inorganic bases Examples of suitable organic bases include tertiary organic amines, in particular tertiary lower alkylamines such as triethylamine, tripropylamines or N-lower alkylpiperidines. Particularly suitable inorganic bases include alkali metal carbonates or bicarbonates. If the acid itself or alternatively an ester is employed as the acylating agent, the reaction of the compound of formula Ie with the acid of the formula VII can advantageously be carried out in the presence of a dehydrating reagent, for example a coupling reagent known from peptide chemistry as suitable for amide formation. Examples of reagents of this type which may be mentioned, which also promote acylation in that they react in situ with the acid to form a reactive acid derivative, include in particular alkylcarbodiimides, for example cycloalkylcarbodiimides such as dicyclohexylcarbodiimide or 1-ethyl-3-[3-(dimethylamino)propyl]-carbodiimide, or carbonyldiimidazole or N-lower alkyl-2-halopyridinium salts, in particular halides or tosylates, preferably N-methyl-2-chloropyridinium iodide. Reaction in the presence of a dehydrating coupling reagent can advantageously be carried out at temperatures from −30° C. to +50° C. under neutral reaction conditions in solvents such as halogenated hydrocarbons and/or aromatic hydrocarbons.

The acylation of such compounds of the formula Ie in which $R^{1VI}$ denotes hydrogen can be carried out under customary conditions for acylating aromatic compounds, for example the conditions of a Friedel-Crafts acylation. Thus, the acylation can be carried out in the presence of a Lewis acid in an organic, highly anhydrous solvent which is inert under the reaction conditions. Lewis acids particularly suitable as Friedel-Crafts catalysts are known compounds such as aluminum halides, in particular aluminum trichloride, zinc halides such as zinc dichloride, tin halides or titanium halides such as tin tetrachloride or titanium tetrachloride or else boron halides such as boron trichloride or boron trifluoride. Suitable solvents which are inert under the reaction conditions include, for example, the abovementioned aliphatic halogenated hydrocarbons, for example chloroform, or alternatively carbon disulfide or nitrobenzene. The reaction can be carried out at temperatures between 0° C. and the boiling temperature of the solvent.

Depending on the starting material of formula Ie to be acylated and the reaction conditions, the reaction time for the acylation can be between 1 and 15 hours. If in the compounds of formula Ie $R^3$, $R^4$ and/or Z contain free hydroxyl groups, these are co-acylated in the acylation. The resulting ester groups can then be cleaved again by hydrolysis in a known manner. If desired, phenolic hydroxyl groups in the radicals $R^3$ or $R^4$ can also be protected by known ether-protective groups which can then be removed by hydrogenolysis or solvolysis.

In compounds of the formula I in which $R^1$ denotes methoxy or contains a methoxyphenyl group and/or $R^3$ and/or $R^4$ represent or contain a methoxyphenyl group, the methoxy group can be cleaved to give the hydroxyl group in a known manner using methods suitable for the cleavage of methoxyaryl ethers. For example, the ether cleavage can be carried out by treating with hydrogen iodide or hydrogen bromide in a solvent which is inert under the reaction conditions, for example acetic anhydride or acetic acid, or with iodotrimethylsilane or with boron tribromide in a halogenated hydrocarbon such as dichloromethane.

From compounds of the formula I, in which $R^1$, $R^3$ and/or $R^4$ contain a hydroxyalkyl group containing at least 2 carbon atoms, compounds of the formula I having a corresponding alkenyl group can be obtained by elimination of water. The elimination of water can be effected by customary methods for dehydrating alcohols by treating with acidic water-eliminating agents. Advantageously, the elimination of water is carried out in an inert organic solvent which forms an azeotropic mixture with water which can easily be removed by distillation. Thus, aromatic hydrocarbons such as, for example, benzene or toluene are suitable. Advantageously, the hydroxyalkyl-containing compound of the formula I is treated with the dehydrating agent at the boiling temperature of the solvent. Suitable dehydrating agents include strong inorganic acids such as, for example, sulfuric acid, or strong organic acids such as, for example, benzenesulfonic acids, which can optionally be substituted in the benzene ring by lower alkyl or halogen, or lower aliphatic halocarboxylic acids such as trifluoroacetic acid. If the hydroxyalkyl group in the compounds of the formula I is a tertiary alcohol group, less strongly active acids such as, for example, concentrated hydrochloric acid can also be employed. The reaction temperature and the reaction time can be varied depending on the strength of the acids employed for the elimination of water. Thus, the reaction times can be between 1 and 15 hours.

In compounds of the formula I in which only the radical $R^1$ contains a hydroxyalkyl group, this can be oxidized, if desired, to the corresponding alkanoyl group. The oxidation can be carried out by customary methods for oxidizing alcohols to aldehydes or ketones by treating with an oxidizing agent. Suitable oxidizing agents include, for example, inorganic oxidizing agents such as, for example, chromium(VI) compounds, for example chromate salts or pyridinium chlorochromate, manganese(IV) compounds or permanganates or else organic oxidizing agents, for example dimethyl sulfoxide complexes such as dimethyl sulfoxide/oxalyl chloride (Swern reagent) or dimethyl sulfoxide/acetic anhydride or dimethyl sulfoxide/trifluoroacetic anhydride. The reaction can be carried out in non-oxidizable solvents which are inert under the reaction conditions, for example halogenated hydrocarbons, at temperatures between −80° C. and room temperature.

Compounds of the formula I obtained, in which $R^1$ denotes amino, can subsequently be alkylated, if desired, to give the corresponding N-mono- or di-lower alkyl compounds in a known manner. Suitable alkylating agents include alkyl halides in particular iodides, alkyl sulfates or alkylsulfonic acid esters. The alkylation can be carried out by customary methods for alkylating anilines under basic conditions in a solvent which is inert under the reaction conditions. It can be carried out, for example, in the manner described for the reaction of the compounds of formula II with compounds of formula III. In general, in the subsequent alkylation of compounds of the formula I a mixture of mono- and dialkylated compounds is obtained in which the amount of dialkylated compounds varies depending on the amount of alkylating agent employed and the reaction conditions. The monoalkylated and dialkylated compounds can be separated from one another in a known manner, for example by chromatography on silica gel. The subsequent alkylation can also be carried out as a reductive alkylation in a known manner by reaction with a lower aldehyde, in particular formaldehyde, under reducing conditions. For example, the compounds can be reacted with the aldehyde in the presence of a reducing agent, for example formic acid. If desired, the reductive alkylation can also be carried out by reaction of the compound with the aldehyde and catalytic hydrogenation of the reaction mixture. A suitable hydrogenation catalyst is, for example, palladium on carbon.

Sulfur-containing compounds of the formula I, for example compounds of the formula I in which A denotes sulfur, can be oxidized in a known manner, if desired, to the corresponding S-mono- or -dioxides. In this reaction, possible alkylthio groups $R^1$ are also oxidized. Suitable oxidizing agents include, for example, hydrogen peroxide in the presence of an organic solvent containing hydroxyl groups, for example acetic acid or methanol, or peracids, for example peracetic acid in an aromatic hydrocarbon such as benzene, 3-chloroperbenzoic acid in an aprotic solvent which is inert under the reaction conditions such as a halohydrocarbon, for example dichloromethane or chloroform, or alternatively acetone, or sodium periodide in a mixture of acetone and a lower alcohol, in particular methanol Depending on the type of oxidizing agent used, the reaction temperature can vary and can be, for example, between −10° C. and 50° C. If desired, still further organic solvents which are inert under the reaction conditions, for example aromatic hydrocarbons such as benzene or toluene, can be added to the reaction medium During the oxidation, a mixture of S-monooxide and S-dioxide compounds is in general obtained in which the amount of S-dioxide compound can vary, depending on the amount of oxidizing agent employed, the oxidation temperature and the oxidation time. The S-monooxide and the S-dioxide can be separated from one another in a known manner, for example by chromatography on silica gel.

The compounds of the formula I can be isolated from the reaction mixture and purified in a known manner. Acid addition salts can be converted into the free bases in the customary manner and these can be converted, if desired, into pharmacologically acceptable acid addition salts in a known manner.

Suitable pharmacologically acceptable acid addition salts of the compounds of formula I include, for example, their salts with inorganic acids, for example halohydric acids, in particular hydrochloric acid, sulfuric acid or phosphoric acids, or with organic acids, for example lower aliphatic mono- or dicarboxylic acids such as maleic acid, fumaric acid, lactic acid, tartaric acid or acetic acid, or sulfonic acids, for example lower alkanesulfonic acids such as methanesulfonic acid or benzenesulfonic acids optionally substituted in the benzene ring by halogen or lower alkyl, such as p-toluenesulfonic acid, or cyclohexylaminosulfonic acid.

If $R^4$ does not denote hydrogen, the compounds of formula I contain an asymmetric center. Other asymmetric centers may possibly be present in individual substituents, for example in a substituted alkylene chain Z. Compounds of formula I which contain a an asymmetric center can exist in several optically active enantiomeric forms or as a racemate. The present invention includes both the racemic mixtures and the pure optical isomers of the compounds of the formula I.

If racemates of the starting compounds of formulas II, IV or V are employed in the synthesis, the compounds of formula I are obtained in the form of racemates. Starting from optically active forms of the starting compounds, optically active compounds of formula I can be obtained. The optically active compounds of formula I can be obtained from the racemic mixtures in a known manner, for example by chromatographic separation on chiral separating materials or by reaction with suitable optically active acids, for example tartaric acid or 10-camphorsulfonic acid, and subsequent resolution into their optically active antipodes by fractional crystallization of the resulting salts.

The starting compounds of formula II are novel compounds which are useful intermediates for preparing pharmacologically active compounds, for example the compounds of the formula I.

Compounds of the general formula IIa

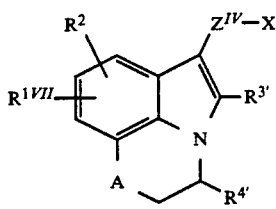

in which $R^2$, $R^3$, $R^4$, A and X have the above meanings and $R^{1VII}$ has the meaning given for $R^1$ with the exception of hydroxyl, amino, nitro or CO-containing radicals, and $Z^{IV}$ has the meaning given for Z with the exception of hydroxyl-substituted chains, can be obtained in a known manner from the corresponding alcohols of the general formula VIII.

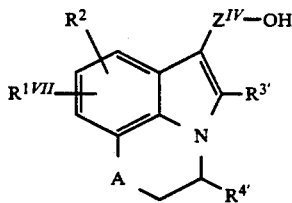

VIII in which $R^{1VII}$, $R^2$, $R^3$, $R^4$ A and $Z^{IV}$ have the above meanings, by converting the hydroxyl group into a leaving group X in a known manner. Thus, for example, in order to introduce a halogen radical X, the compounds of the formula VIII can be reacted with thionyl chloride or with phosphorus halides, for example phosphorus tribromide, in a known manner in a solvent which is inert under the reaction conditions, for example a halogenated hydrocarbon such as chloroform. Sulfonic acid radicals X can be introduced in a known manner by acylating compounds of the formula VIII with a corresponding sulfonyl chloride.

Compounds of the general formula IIb

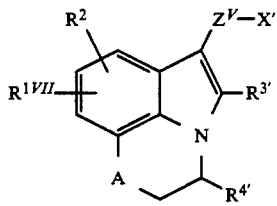

IIb in which $R^{1VII}$, $R^2$, $R^3$, $R^4$, A and X' have the above meanings and $Z^V$ denotes an alkylene chain having 2–4 carbon atoms, which is substituted by hydroxyl in the position adjacent to the indole structure and optionally substituted by lower alkyl, can be obtained in a known manner starting from compounds of the general formula IXa

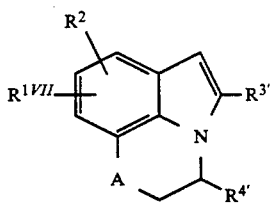

IXa in which $R^{1VII}$, $R^2$, $R^3$, $R^4$ and A have the above meanings, by reacting compounds of the formula IXa with a halocarboxylic acid derivative of the general formula XXVI

X'—Q''—Y'   XXVI in which X' has the above meaning, Q'' denotes an alkylene chain having 1-3 carbon atoms which is substituted by oxo in the position adjacent to the radical Y' and which can optionally be substituted by lower alkyl, and Y' represents halogen or the radical X'—Q''—O, in which X' and Q'' have the above meanings, in a solvent which is inert under the reaction conditions in the presence of a Friedel-crafts catalyst such as aluminum trichloride in a known manner to give compounds of the general formula XXVIIa

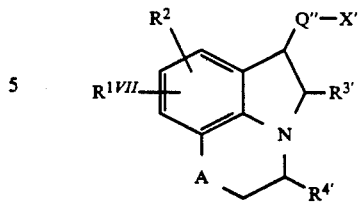

XXVIIa in which $R^{1VII}$, $R^2$, $R^3$, $R^4$, A and X' have the above meanings and Q'' denotes an alkylene chain having 1-3 carbon atoms, which is substituted by oxo in the position adjacent to the indole structure and which can optionally be substituted by lower alkyl, and this is subsequently reduced in a known manner with a reducing agent which does not attack the halogen substituent X', for example sodium borohydride.

The reaction of compounds of the formula IXa with compounds of the formula XXVI can be carried out under customary conditions for acylating aromatic compounds by the Friedel Crafts method.

If compounds are prepared in which Q'' represents the —CO—CH$_2$ group, the compounds of the formula IXa can also initially be acylated with acetic anhydride in a Friedel-Crafts reaction, and the resulting acetyl derivatives can be halogenated, for example brominated, in a known manner to give corresponding compounds of the formula XXVIIa.

In compounds of the formulas IIa and IIb, in which $R^{1VII}$ denotes methoxy or contains a methoxyphenyl group and/or $R^3$ and/or $R^4$ represent or contain a methoxyphenyl group, the methoxy group can be cleaved, if desired, to give the hydroxyl group in a known manner. The cleavage can be carried out under customary conditions for cleaving phenol ethers, for example under the conditions given above for the liberation of a hydroxyl group from a methoxy group $R^1$ in the compounds of the formula I.

If desired, a chlorine or bromine substituent $R^1$ or $R^2$ can be introduced into the compounds of the formula II in a known manner, for example by treating the compounds with elemental chlorine or bromine in glacial acetic acid. If desired, a nitro substituent $R^1$ or $R^2$ can also be introduced in a known manner, for example by treating with a nitric acid/sulfuric acid mixture.

In compounds of the formula II in which R' denotes nitro and X denotes a non-reducible radical, preferably tosyloxy, the nitro group can be reduced to the amino group in a known manner. The reduction can be carried out with customary reducing agents for reducing nitro groups to amino groups, for example by catalytic hydrogenation in the presence of a palladium/carbon catalyst in a lower alcohol or by reduction by means of sodium borohydride in the presence of a palladium/carbon catalyst in an ether such as tetrahydrofuran.

Compounds of the formula II in which $R^1$ denotes hydrogen, hydroxyl or amino can be converted in a known manner by acylation with compounds of the formula VII into those compounds of formula II in which $R^1$ has the meaning given for $R^4$ in the compounds of formula Id. The acylation can be carried out by known methods and can be carried out, for example, under the conditions given for the acylation of compounds of formula Ie according to process variant d).

Alcohols of the formula VIII are novel compounds which are useful intermediates for preparing pharmacologically active compounds, for example the compounds of formula I. They can be obtained in a known manner by reducing esters of the general formula Xb

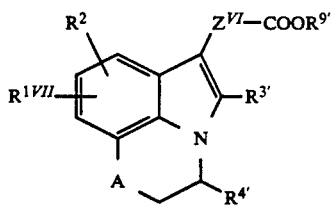

in which $R^{1VII}$, $R^2$, $R^3$, $R^4$ and A have the above meanings, $Z^{VI}$ represents an alkylene chain having 1-3 carbon atoms which is optionally substituted by lower alkyl, and $R^9$ denotes lower alkyl. Suitable reducing agents include, for example, hydride reducing agents capable of reducing esters, for example the reducing agents given above for the reduction of compounds of formula IV under process variant b), in particular lithium aluminum hydride or diborane. The reduction can be carried out by customary methods, for example under the reaction conditions given for the reduction of compounds of formula IV according to process variant b). Reduction with lithium aluminum hydride in tetrahydrofuran is particularly advantageous.

Compounds of the general formula X

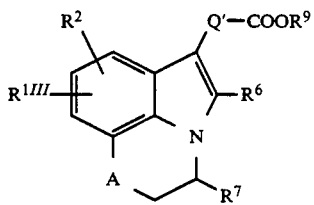

in which $R^{1III}$, $R^2$, $R^6$, $R^7$, A and Q' have the above meanings, and $R^9$ denotes hydrogen or lower alkyl, can be obtained in a known manner. Thus, compounds of the general formula Xa

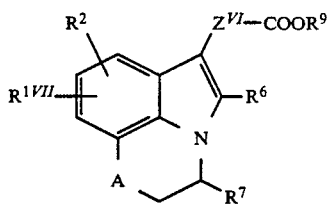

in which $R^{1VII}$, $R^2$, $R^6$, $R^7$, A, $Z^{VI}$ and $R^9$ have the above meanings, are obtained by reacting hydrazine compounds of the general formula XIa

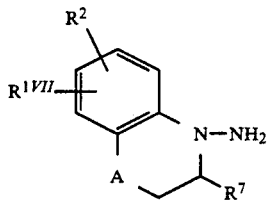

in which $R^{1VII}$, $R^2$, $R^7$ and A have the above meanings, with compounds of the general formula XII $$R^9O-CO-Z^{VI}-CH_2-CO-R^{10} \quad \text{XII}$$

in which $R^9$ and $Z^{VI}$ have the above meanings and $R^{10}$ has the meaning given for $R^6$ with the exception of hydrogen or represents a carboxyl group, in a known manner, for example under the conditions of the Fischer indole synthesis in which intermediate hydrazone compounds of the general formula XIII

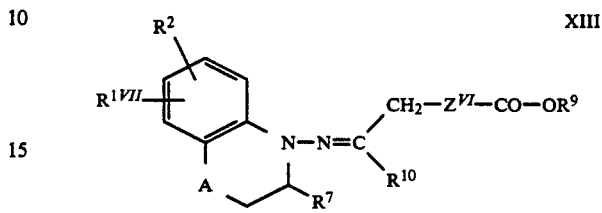

in which $R^{1VII}$, $R^2$, $R^7$, A, $Z^{VI}$, $R^9$ and $R^{10}$ have the above meanings, are formed, which further condense to give the compounds of the formula Xa. In this reaction, a possible carboxyl group $R^{10}$ is eliminated, so that when using compounds of the formula XII in which $R^{10}$ represents a carboxyl group, compounds of the formula Xa are obtained in which $R^6$ denotes hydrogen. The reaction can be carried out by heating to temperatures between 50° and 100° C. in acidic medium, for example in a water-miscible organic solvent, such as a lower alcohol or acetic acid, which contains an acid, such as aqueous hydrochloric, sulfuric or phosphoric acid, or it can be carried out in neutral medium in the presence of zeolite. If esters of the formula XII are employed in the reaction, mixtures of esters and acids of the formula Xa can be obtained in which the ratio of ester to acid can vary, depending on the reaction conditions, and from which the esters and/or the acids can be isolated by chromatographic purification.

If desired, esters of the formula Xa can be hydrolyzed to the corresponding acids of the formula Xa, and the acids or mixtures containing acids and esters can be converted into the corresponding esters in a known manner by reaction with lower alcohols. In an ester hydrolysis, the $Z^{VI}$—COO—$R^9$ ester group reacts preferentially before any alkoxycarbonyl group $R^6$ which may be bonded directly to the ring structure.

If desired, further substituents $R^{1III}$ can be introduced into compounds of the formula X. For example, the nitro group, halogen or an acyl radical $R^{1III}$ can be introduced in a known manner, for example as described above for the compounds of the formula II, or a methoxy group $R^{1III}$ can be cleaved to give the hydroxyl group. If desired, an acyl radical $R^{1III}$ can be reduced to the corresponding alkyl radical in a known manner. This can suitably be achieved, for example, by reduction with hydrazine in the presence of an inorganic base, such as an alkali metal hydroxide, in a high-boiling ether. If desired, a possible nitro group $R^{1III}$ can be reduced to the amino group. The reduction can be carried out in a known manner using a reducing agent which is capable of selectively reducing the nitro group to the amino group without reductively attacking the alkoxycarbonyl function, for example by catalytic hydrogenation. If desired, an amino group $R^{1III}$ can be acylated in a known manner. If desired, in esters of the formula Xa an amino group $R^{1III}$ can by alkylated to the di-lower alkylamino group. The alkylation can be carried out in a known manner, for example as described above for the compounds of the formula I.

Compounds of the general formula XI

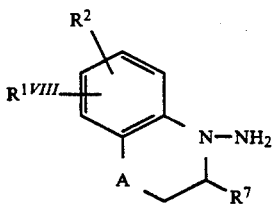

in which $R^2$, A and $R^7$ have the above meanings and $R^{1VIII}$ has the meaning given for $R^1$ with the exception of amino, nitro and of radicals containing the —COO group or the —CONH group, can be obtained in a known manner starting from compounds of the general formula XIV

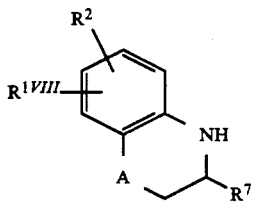

in which $R^{1VIII}$, $R^2$, $R^7$ and A have the above meanings. For this purpose, compounds of formula XIV are converted by treatment with sodium nitrite in a known manner into the corresponding N-nitroso compounds of formula XV

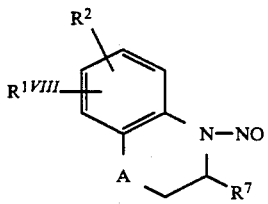

in which $R^{1VIII}$, $R^2$, $R^7$ and A have the above meanings, and these are then reduced to the hydrazine compounds of formula XI. All known reduction methods for reducing nitroso compounds to corresponding hydrazine compounds may be used for reducing the nitroso compounds of formula XV. Suitable reducing agents include, for example, lithium aluminum hydride in tetrahydrofuran or metallic zinc powder in the presence of acid or sodium dithionite. It is also possible to catalytically hydrolyze the nitroso compounds to the hydrazines of formula XI. If the substituent $R^7$ contains a lower alkoxycarbonyl function, this can optionally also be reduced during the reduction, for example when using lithium aluminum hydride as the reducing agent, to the corresponding hydroxymethyl function. If $R^{1VIII}$ contains a carbonyl group, reducing agents must be chosen which do not attack this carbonyl group.

Advantageously, the preparation of esters of the formula Xa starting from the compounds of the formula XIV can be carried out in a one-pot process without isolating the individual intermediate. In this reaction, metallic zinc powder in the presence of acid is employed to reduce the N-nitroso compound, and the reaction mixture obtained after the reduction containing zinc salt and the hydrazine compound of the formula XI is acidified by addition o hydrochloric acid, and an ester of the formula XII is then added to the reaction mixture. When the ester of formula XII is added to the reaction mixture, the hydrazone compound of formula XIII is formed as an intermediate which condenses further under the reaction conditions to the ester of the formula Xa.

Compounds of the general formula Xc

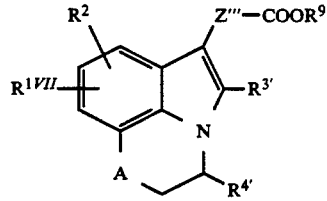

in which $R^{1VII}$, $R^2$, $R^3$, $R^4$, $R^9$, A and $Z'''$ have the above meanings, can be obtained starting from compounds of the general formula IIc

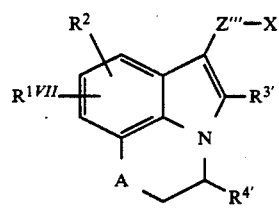

in which $R^{1VII}$, $R^2$, $R^3$, $R^4$, A, $Z'''$ and X have the above meanings, by initially converting a compound of the formula IIc into a corresponding nitrile by reaction with sodium cyanide in a known manner and then hydrolyzing this nitrile to the acid of the formula Xc or converting it into an ester of the formula Xc by solvolysis in a lower alcohol and subsequent hydrolysis of the iminoether formed as an intermediate. The reaction of a compound of formula IIc with sodium cyanide can be carried out by treating a solution o a compound of formula IIc with aqueous sodium cyanide solution in an organic solvent. The hydrolysis or solvolysis of the resulting nitrile is advantageously carried out i acidic medium.

The acids of the formula Xd

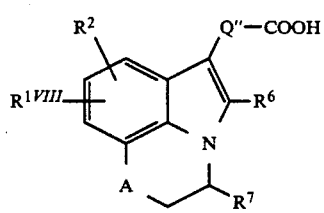

in which $R^{1VIII}$, $R^2$, $R^6$, $R^7$, $Q''$ and A have the above meanings, or corresponding acid halides or salts, can be obtained starting from compounds of the general formula IX

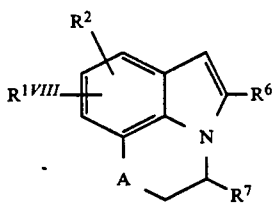

IX in which $R^{1VIII}$, $R^2$, $R^6$, $R^7$ and A have the above meanings, by reacting compounds of the formula IX in a known manner with dicarboxylic acid halides of the general formula XXIX

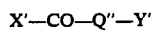

XXIX in which X', Q" and Y' have the above meanings, under the conditions of a Friedel-Crafts acylation. The resulting halides of the acids of formula Xd can immediately be processed further in situ or converted to salts of the acids Xd in a known manner.

Compounds of formula IX can be prepared in a known manner. Thus, the hydrazine compounds of formula XI can e reacted with compounds of the general formula XVI

XVI in which $R^6$ has the abovementioned meaning, in a known manner, for example under the conditions of the Fischer indole synthesis, to form a hydrazone intermediate which condenses further to give the compounds of the formula IX. The reaction can be carried out, for example, under the reaction conditions given for the reaction of compounds of formula XI with compounds of formula XII. If desired, halogen substituents $R^{1VIII}$ can subsequently be introduced into compounds of the formula IX, for example in the manner described above for compounds of the formula II. Possible acyl radicals $R^6$ can be reduced to corresponding alkyl radicals in a known manner, for example by means of hydrazine under the conditions given above for compounds of the formula Xa.

Compounds of the formula XIV are known or can be prepared by, or analogously to, known methods. For example, compounds of the general formula XIVa

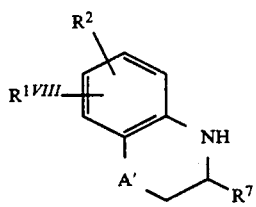

XIVa in which $R^{1VIII}$, $R^2$ and $R^7$ have the above meanings, and A' denotes a methylene group which is optionally substituted by lower alkyl, can be obtained in a known manner by reducing compounds of the general formula XVII or compounds of the general formula XVIII

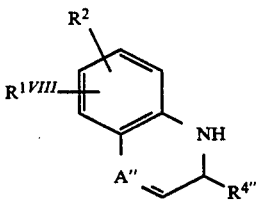

XVII

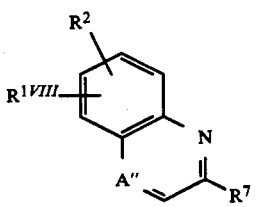

XVIII in which $R^{1VIII}$, $R^2$ and $R^7$ have the above meanings, A" denotes a CH group which is optionally substituted by lower alkyl, and $R^{4''}$ has the meaning given for $R^4$ with the exception of radicals containing free hydroxyl groups. Thus, the tetrahydroquinoline derivatives of the formula XVII can be reduced, for example, by treatment with metallic sodium in a lower alcohol, preferably at the boiling temperature of the reaction mixture. The reduction of the quinoline derivatives of the formula XVIII can be carried out, for example, by reduction with sodium cyanoborohydride in acidic medium, for example in acetic acid or an alcohol/hydrochloric acid mixture, or with a diborane/pyridine complex in acetic acid.

Tetrahydroquinoline derivatives of the formula XVII can be obtained, for example, by reacting quinoline derivatives of the formula XVIII, in which $R^7$ denotes hydrogen, in a known manner with an organolithium compound of the general formula XIX

XIX in which $R^{4''}$ has the above meaning. The reaction can be carried out, for example, in an ether such as tetrahydrofuran at temperatures from 0° C. to room temperature.

The quinoline derivatives of formula XVIII are known or can be prepared by, or analogously to, known methods. For example, in compounds of the formula XVIII in which $R^7$ represents a methyl group, this methyl group can be converted into another radical $R^7$ in a known manner, for example by reaction with a compound of the general formula XX

XX in which X' has the above meaning and $R^{4''''}$ corresponds to a radical $R^4$ which is decreased by one $CH_2$ group and which contains no free hydroxyl groups. Such a reaction can be carried out, for example, in the presence of a strong base capable of deprotonating the methyl group, such as butyllithium, in a solvent which is inert under the reaction conditions, for example an ether, at temperatures between 0° C. and room temperature.

Compounds of the general formula XIVb

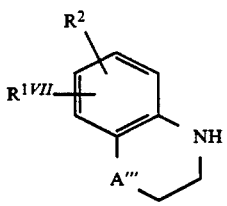

in which $R^{1VII}$ and $R^2$ have the above meanings and $A'''$ represents oxygen or sulfur, can be obtained by reduction of compounds of the general formula XXI

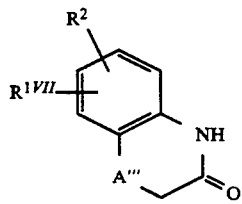
XXI in which $R^{1VII}$, $R^2$ and $A'''$ have the above meanings. The reduction can be carried out, for example, with lithium aluminum hydride in a cyclic ether such as tetrahydrofuran at elevated temperature, preferably the boiling temperature of the reaction mixture.

Compounds of the formula XXI can be obtained from corresponding aminophenols or aminothiophenols of the general formula XXII

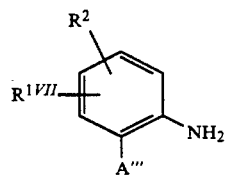
XXII in which $R^{1VII}$, $R^2$ and $A'''$ have the above meanings, in a known manner by reaction with chloroacetyl chloride.

Compounds of the general formula XIVc

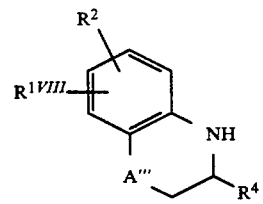
XIVc in which $A'''$, $R^{1VIII}$, $R^2$ and $R^4$ have the above meanings, can be obtained by reacting nitrophenols or nitrothiophenols of the general formula XXX

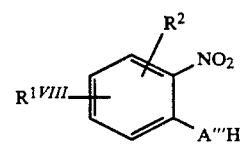
XXX in which $R^{1VIII}$, $R^2$ and $A'''$ have the above meanings, with compounds of the general formula XXXI

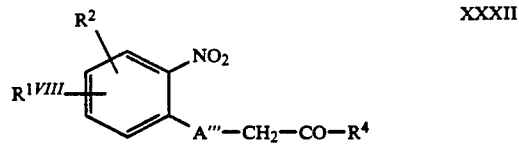
XXXI in which $R^4$ and $X'$ have the above meanings, to give compounds of the general formula XXXII

XXXII in which $R^{1VIII}$, $R^2 A'''$ and $R^4$ have the above meanings and then cyclizing these under reducing conditions. The reaction of compounds of the formula XXX with compounds of the formula XXXI can be carried out in a known manner under customary conditions for forming a phenol ether. The reductive cyclization of compounds of formula XXXII can be carried out in a known manner by treating the compounds of formula XXXII with a reducing agent in a solvent which is inert under the reaction conditions. Suitable reducing agents include, or example, hydrogen in the presence of a hydrogenation catalyst, in particular palladium/carbon, or alternatively hydrazine in the presence of Raney nickel. After reduction is complete, the cyclization is completed by heating the reduction product to temperatures from 20° to 100° C. If $R^1$ and/or $R^4$ are optionally substituted benzyl radicals, these can also be removed in a catalytic hydrogenation, and possible alkenyl radicals can also be hydrogenated.

Compounds of the general formula XIVd

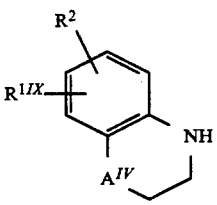
XIVd in which $R^{1IX}$ has the meaning given for $R^{1VII}$ with the exception of cyano, $R^2$ has the above meaning, and $A^{IV}$ denotes an ethylene group which is optionally substituted by lower alkyl, can be obtained in a known manner starting from compounds of the general formula XXVIII

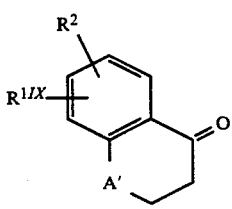
XXVIII in which $R^{1IX}$, $R^2$ and $A'$ have the above meanings, by initially reacting compounds of the formula XXVIII with hydroxylamine to give the corresponding oxime compounds of the general formula XXXV

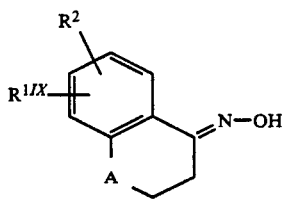

XXXV in which $R^{1IX}$, $R^2$ and $A'$ have the above meanings, and then subjecting these to a reductive rearrangement to give the compounds of the formula XIVd. The rearrangement can e carried out in a known manner using diisobutylaluminum hydride ("DIBAH") in a solvent which is inert under the reaction conditions.

In compounds of the general formula XIVe

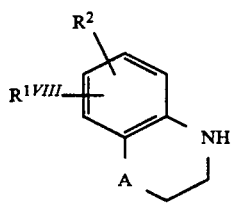

XIVe in which $R^{1VIII}$, $R^2$ and A have the above meanings, further radicals $R^7$ can be introduced in a known manner, for example by the method described by A. I. Meyers and S. Hellring in Tetrahedron Letters, 22 pages 5119 to 5122 (1981) and by A. I. Meyers in Lectures in Heterocyclic Chemistry, Volume VII, pages 75 to 81 (1984), by first converting the compounds of the formula XIVe into their formamidine derivatives of the general formula XXXIII

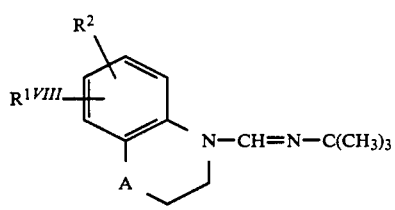

XXXIII in which $R^{1VIII}$, $R^2$ and A have the above meanings, and which are activated by the electron-withdrawing substituents toward deprotonation on the carbon atom adjacent to the nitrogen atom. The compounds of formula XXXIII can then be converted into the corresponding anion by reaction with a strong base such as tert-butyllithium and reacted with compounds of the general formula XXXIV $R^{7'}$—X'      XXXIV in which X' has the above meaning, and $R^{7'}$ has the meaning given for $R^7$ with the exception of hydrogen, and the formamidine group can then be removed from the reaction product again under alkaline or acidic conditions.

Compounds of the formula III are known or can be prepared by, or analogously to, known methods.

Compounds of the general formula IIIa

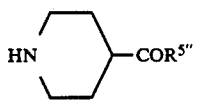

IIIa in which $R^{5''}$ denotes a phenyl radical which is optionally substituted by lower alkyl, lower alkoxy or halogen, can obtained, for example, starting from 4-piperidine carboxylic acid by converting the acid into an acid halide after introduction of an amino-protective group and reacting this acid halide in a known manner with a compound of the general formula XXIII

H—$R^{5''}$      XXIII in which $R^{5''}$ has the above meaning, and then removing the amino-protective group again. The reaction can be carried out under customary conditions for acylating aromatic compounds, for example the conditions of a Friedel-Crafts acylation in the presence of aluminum trichloride.

Compounds of the formula IV are novel compounds which are useful intermediates for preparing pharmacologically active compounds, for example the compounds of formula I. They can be prepared by known methods.

Compounds of the general formula IVa

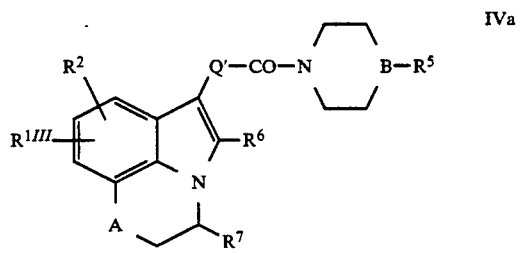

IVa in which $R^{1III}$, $R^2$, $R^6$, $R^7$A, Q', B and $R^5$ have the above meanings, can be obtained, for example, by reacting acids of the formula X or their reactive acid derivatives with an amine of the general formula IIIb

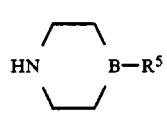

IIIb in which B and $R^5$ have the above meanings. The reaction can be carried out by customary methods for forming amide groups by aminoacylation. Thus, acids or reactive acid derivatives of the general formula X'

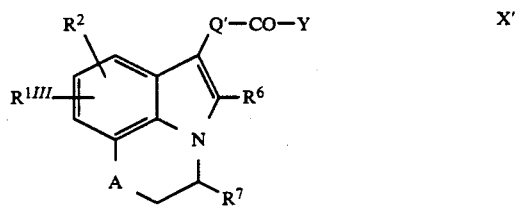

X' in which $R^{1III}$, $R^2$, $R^6$, $R^7$, A, Q' and Y have the above meanings are employed. The reaction can be carried out under customary conditions for aminoacylation, for example under the conditions given for the acylation of amino compounds of the formula Ie. Advantageously, for example, an acid is reacted with the piperazine derivative in a halogenated hydrocarbon, such as dichloromethane, in the presence of a coupling reagent, such as carbonyldiimidazole.

If desired, further substituents $R^{1III}$ can be introduced into compounds of formula IV. Thus, for example, the nitro group, halogen or an acyl radical $R^{1III}$ can be introduced in a known manner as described above for the compounds of formula II.

If desired, in compounds of the formula IV in which $R^{1III}$ represents nitro, the nitro group can be reduced to an amino group in a known manner. The reduction can be carried out, for example, in the manner given for the reduction of a nitro group in the compounds of the formulas IIa and IIb or X. If desired, an amino group $R^{1III}$ can be acylated or alkylated to the di-lower alkyl group in a known manner. The alkylation can be carried out in a known manner, for example as described above for the compounds of the formula I.

Compounds of the general formula IVb

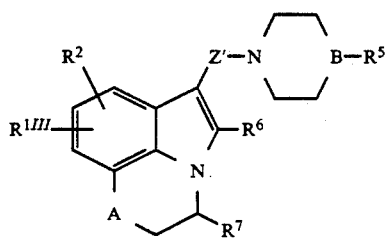

in which $R^{1III}$, $R^2$, $R^6$, $R^7$, A, Z', B and $R^5$ have the above meanings, include compounds of the formula I in which $R^1$ denotes a lower alkanoyl group, a lower alkanoylamino group or a benzoyl or cinnamoyl group whose phenyl ring can optionally be substituted by lower alkyl, lower alkoxy or halogen. Compounds of formula IVb in which $R^6$ and/or $R^7$ contain a lower alkoxy carbonyl group can be obtained by introducing a radical containing a lower alkoxycarbonyl group into the radicals $R^3$ and/or $R^4$ of corresponding compounds of the formula I. Thus, for example, compounds of the formula I in which $R^3$ and/or $R^4$ denote a phenyl or phenyl-lower alkyl group substituted in the phenyl ring by hydroxyl can be reacted with a lower alkyl ester of a lower halocarboxylic acid to convert the hydroxyl group into a lower alkoxycarbonylalkoxy group. The reaction can be carried out under customary conditions for forming a phenol ether, for example in the presence of a strong base such as sodium hydride in a solvent which is inert under the reaction conditions, for example dimethylformamide. Compounds of the formula IVb in which $R^{1III}$ denotes an N-formyl-substituted amino or lower alkylamino group can be obtained from corresponding compounds of the formula I in which $R^1$ denotes an amino or lower alkylamino group by formylating these in a known manner.

Compounds of the general formula IVc

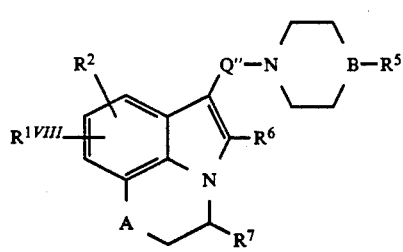

i which $R^{1VIII}$, $R^2$, $R^5$, $R^6$, $R^7$, A, B and Q" have the above meanings, can be obtained by reacting compounds of the general formula XXVII

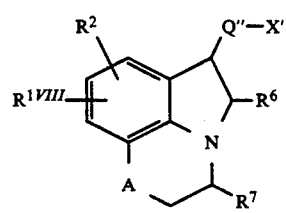

in which $R^{1VIII}$, $R^2$, $R^6$, $R^7$, A, Q" and X' have the above meanings, with compounds of formula IIIb.

Compounds of the formula XXVII can be obtained by acylating compounds of the formula IX with compounds of the formula XXVI in a Friedel-Crafts reaction Compounds of the general formula V are novel compounds which are useful intermediates for preparing pharmacologically active compounds, for example the compounds of he formula I. They can be obtained by removing the protective group in a known manner from compounds of the general formula XXIV

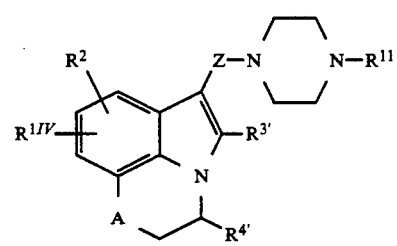

in which $R^{1IV}$, $R^2$, $R^3$, $R^4$, Z and A have the above meanings, and $R^{11}$ denotes an amino-protective group. Suitable amino-protective groups $R^{11}$ include known protective groups which can be removed by hydrolysis or hydrogenolysis such as, for example, lower alkanoyl, formyl or benzyl. Compounds of formula XXIV can be obtained analogously to the methods described for preparing compounds of the formula I according to process a) or b) by reacting compounds of the general formula XXV

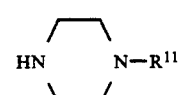

in which $R^{11}$ has the above meaning, with compounds of the formula II, or reacting with acids of the formula X or their reactive acid derivatives and reducing the reaction product. The reaction of compounds of formula II with compounds of formula XXV can be carried out by customary methods for aminoalkylation and, for example, under the reaction conditions given for the reaction of compounds of formula II with compounds of formula III. If $R^{1IV}$ represents an amino group which is to be provided with a protective group, the protective group $R^{11}$ chosen is a different protective group which can be removed using conditions under which the protective group of the radical $R^{1IV}$ is retained.

The compounds of the formula I and their pharmacologically acceptable acid addition salts are characterized by interesting pharmacological properties and have anti-inflammatory and anti-allergic effects. In particular, the compounds exhibit an advantageous activity profile for treating asthmatic disorders and also show low toxicity and good compatibility.

Asthma is a chronic inflammatory lung disease which is characterized by episodically occurring, reversible obstructions of the respiratory passages. It is generally assumed that the induction of asthmatic symptoms and attacks originates from a parenchymal and interstitial cell type known as a mast cell. These mast cells contain preformed inflammatory mediators and spasmogens, in particular histamine. They are also capable of de novo synthesis of a number of mediators derived from membrane lipids. Mast cells also act in combination with a multiplicity of associated cells which are all capable of synthesizing inflammatory and pro-inflammatory mediators.

As long as no allergy-inducing conditions are present, the mast cells are in a quasi non-involved waiting position. The key to the allergic reactions lies in the presence of high concentrations of circulating IgE antibodies. When these antibodies are bound to a corresponding antigen, they activate both the degranulation and release of preformed mediators and the de novo synthesis of other mediators.

Since asthma is an inflammatory obstructive lung disease, the therapy is based on essentially two approaches: alleviation of the symptomatic complaints by administration of bronchodilators such as β-sympathomimetic agents, xanthine derivatives and anticholinergic agents; administration of anti-inflammatory active substances such as disodium cromoglycinate and steroids; and target therapy directed at specific mediators such as, for example histamine. Treatment to alleviate the symptomatic complaints is adequate in about 50% of asthmatics, but does not contribute anything to alleviating the causes, that is the inflammation. Anti-inflammatory active substances may control the inflammation, but often have undesirable side effects and are frequently administered simultaneously with bronchodilators. Target therapy directed only at one specific mediator alone is completely inadequate, since there are a multiplicity of mediators.

The substances according to the invention are distinguished in that they have anti-inflammatory activity and are targeted against one or more of the three types of mediator, histamine, leukotrienes and platelet aggregation factor, which are involved not only in acute bronchospasms but also in maintaining the chronic inflammation or are also active against the respective target cells via mediator-specific receptors.

The anti-inflammatory and anti-allergic properties of the compounds can be demonstrated in vitro and in vivo in standard pharmacological test methods.

DESCRIPTION OF THE TEST METHODS

1. Determination of the inhibition of passive cutaneous anaphylaxis (P.C.A.) and of the anaphylactoid cutaneous reaction induced by histamine.

The P.C.A. reaction was carried out according to the methods described by Goose et al. (J.N. Immunology 16 (1969), 749) and by Martin et al (Arch. Pharmacol. 316 (1981), 186}.

The IgE-rich ovalbumin antiserum used in the test was obtained from immunized Brown-Norway rats. For immunization, the rats were given an i.p. injection of a mixture of 100 μg of ovalbumin with a Bordetella pertussis suspension (Vaxicoq ®, Manufacturer: Institut Merieux, containing $5 \times 10^9$ organisms and 1.25 mg of $Al(OH)_3$). After 20 days, the animals received a further i.p. injection of a solution of 10 μg of ovalbumin in 0.5 ml of physiological saline solution for reimmunisation. After a further four days, the animals were bled, and the blood was centrifuged The antiserum obtained in this way was stored at $-20°$ C. until use.

The determination of the inhibition of passive cutaneous anaphylaxis and the anaphylactoid cutaneous reaction induced by histamine was carried out as follows:

Sprague-Dawley rats having a body weight of 150–180 g were injected intradermally in one flank with 50 μl of a 1:75 dilution of the IgE-rich ovalbumin antiserum in physiological sodium chloride solution for passive sensitization to ovalbumin.

24 hours after sensitization a solution of 8.25 mg/kg of ovalbumin and 26.4 mg/kg of a blue dye (Evans' Blue) was administered i.v. to the rats according to Martin et al. to induce passive cutaneous anaphylaxis. The ovalbumin challenge caused a local anaphylactic reaction at the site at which the antiserum had been injected.

To determine the histamine-induced anaphylactoid skin reaction, the animals were injected intradermally in the flank opposite to the antiserum administration with 50 μl of a physiological saline solution containing 0.8 mg/ml of histamine directly before the i.v. injection of the solution containing the ovalbumin and the blue dye.

On the test days, the test substances were dissolved in distilled water which contained 1% by volume of dimethylformamide and 1% by volume of Tween ®20 (polyoxyethylene(20) sorbitan monolaurate). One hour before the challenging ovalbumin administration, each animal received $2 \times 10^{-5}$ mol/kg of test substance administered orally in 0.5 ml of solution. A control group received only the solvent for comparison.

The oedematous anaphylactic (P.C.A.) and anaphylactoid (histamine-induced) reactions caused by the challenging i.v. ovalbumin injection, which are manifested by oedema formation, swelling and exudation of blue dye, were evaluated 30 minutes after challenge by the i.v. ovalbumin injection. This was done by visual determination of the extent to which the blue dye emerges at the sites of oedema formation. The percentage inhibition of anaphylactic and anaphylactoid reactions caused by the test substances was determined in comparison with the reactions of the control animals not treated with test substance with the aid of comparison scales.

The results obtained by the above test methods using compounds of the formula I are shown in the following Table A. The example numbers given for the compounds of formula I relate to the following preparation examples.

TABLE A

| Test Substance Example Number | Inhibitory effect on cutaneous anaphylactic and anaphylactoid reactions in rats % inhibition at a dose of $2 \times 10^{-5}$ mol/kg p.o. | |
|---|---|---|
| | Passive cutaneous anaphylaxis (P.C.A.) | Histamine-induced anaphylactoid reactions |
| 1 | 98 | 85 |
| 3 | 100 | 93 |
| 4 | 55 | 55 |
| 7 | 75 | 35 |
| 9 | 90 | 80 |
| 10 | 83 | 75 |
| 11 | 100 | 93 |
| 12 | 25 | 25 |
| 13 | 83 | 68 |
| 14 | 65 | 25 |
| 15 | 85 | 65 |
| 16 | 85 | 73 |
| 17 | 45 | 25 |
| 18 | 90 | 80 |
| 19 | 95 | 95 |
| 20 | 100 | 95 |
| 21 | 95 | 90 |
| 23 | 100 | 95 |
| 24 | 55 | 60 |
| 25 | 100 | 100 |
| 26 | 95 | 90 |
| 27 | 100 | 95 |
| 28a | 100 | 90 |
| 28b | 100 | 85 |
| 73 | 100 | 95 |
| 76 | 100 | 100 |
| 33 | 100 | 93 |
| 35 | 75 | 58 |
| 37 | 60 | 58 |
| 38 | 63 | 60 |
| 39 | 85 | 65 |
| 40 | 70 | 43 |
| 42 | 50 | 45 |
| 46 | 35 | 25 |
| 47 | 50 | 20 |
| 48 | 25 | 35 |
| 50 | 60 | 50 |
| 54 | 93 | 73 |
| 55 | 80 | 50 |
| 56 | 80 | 50 |
| 57 | 100 | 95 |
| 59 | 95 | 95 |
| 60 | 100 | 95 |
| 61 | 100 | 100 |
| 62 | 100 | 95 |
| 63 | 100 | 95 |
| 65 | 100 | 95 |
| 66 | 80 | 70 |
| 67 | 100 | 95 |
| 77 | 60 | 30 |
| 81 | 86 | 82 |
| 90 | 81 | 77 |
| 91 | 86 | 87 |

2. Determination of the minimum toxic dose.

Maximum doses of 300 mg/kg of the test substance were administered orally to male mice weighing 20–25 g. The animals were observed carefully for 3 hours for toxicity symptoms. In addition, all symptoms and deaths over a period of 24 hours after administration were recorded. Associated symptoms were also observed and recorded. If death or severe toxic symptoms were observed, further mice were administered increasingly lower doses. The lowest dose which caused death or severe toxic symptoms is given as the minimum toxic dose in the following Table B.

TABLE B

| Test Substance Example Number | Minimum toxic dose mg/kg of mouse p.o. |
|---|---|
| 1 | 100 |
| 3 | 300 |
| 11 | 100 |
| 13 | 100 |
| 14 | 300 |
| 35 | 300 |
| 38 | 300 |
| 39 | 300 |
| 40 | 300 |
| 42 | 100 |
| 54 | 300 |
| 55 | 300 |
| 56 | 300 |
| 57 | 300 |

3. Investigation of the antihistamine ($H_1$) effect based on histamine ($H_1$) receptor antagonism in vitro.

To investigate the histamine ($H_1$) receptor antagonism of the substances, the inhibitory effect thereof on histamine-induced contractions of the smooth musculature of isolated organ was determined in vitro. Isolated strips of organ from the ileum were used. In an organ bath of physiological saline solution, they react to addition of histamine by contracting. Addition of the compounds of the invention decreases this histamine-induced contraction of the smooth musculature of the ileum strips. The extent of decrease of the contraction is an indication of the antihistamine ($H_1$) activity of the compounds. The investigation is carried out analogously to the method originally described by Magnus (Pflügers Arch. 102, 123 (1904)).

Experimental description of the determination of the inhibitory effect on the contraction induced by a $5 \times 10^{-6}$ molar histamine concentration on isolated smooth muscle of the guinea-pig ileum.

For the test, 1.5 cm long segments of the ileum from Dunkin Hartley guinea-pigs having a body weight of 300–500 g were employed. Each strip was placed in an organ bath of 10 ml of Krebs-Henseleit physiological saline solution and attached to a customary apparatus for isotonically measuring changes in length of the ileum strip (automated Celaster measuring apparatus) so that the tissue is under a tension of 1 g. The bath was kept at a pH of 7.4 and aerated with a mixture of 5% $CO_2$ and 95% $O_2$. After an equilibration phase, an isotonic contraction of the tissue was produced by adding histamine in a final concentration of $5 \times 10^{-6}$ mol/l and was washed out again after a contact time of 30 seconds. Only those tissues in which three reproducible contractions were obtained at 10 minute intervals were used in the subsequent test. The test substances were then added in a final concentration of $10^{-6}$ mol/l, and after a contact time of 30 seconds histamine was again added up to a concentration of $5 \times 10^{-6}$ mol/l. The contractions which occurred were measured over the course of 30 seconds. The tissue was then washed several times over a period of 10 minutes. A contraction challenge was then induced again by addition of histamine. The contractions which occurred were again measured over 30 seconds. The difference between the amplitude of the contraction obtained by histamine addition alone and the amplitude of the contraction obtained in the presence of the test substance was determined and calculated as % inhibition.

The following Table C shows the results obtained with the test substances according to the method described above. The inhibitory effects on the contractions induced by histamine 30 seconds after administration of the test substance and on the contractions induced by addition of histamine 10 minutes afterward are given in the table.

TABLE C

| Test Substance Example Number | in vitro ($H_1$) receptor antagonism % inhibitory effect on histamine-induced contractions of the Ileum at a histamine concentration of $5 \times 10^{-6}$ mol/l and a test substance concentration of $10^{-6}$ mol/l | |
|---|---|---|
| | after 30 sec. | after 10 min. |
| 1 | 42 | 88 |
| 3 | 15 | 57 |
| 9 | 10 | 78 |
| 10 | 47 | 92 |
| 11 | 21 | 84 |
| 13 | 33 | 63 |
| 15 | 29 | 78 |
| 16 | 42 | 55 |
| 18 | 29 | 72 |
| 19 | 26 | 83 |
| 20 | 27 | 77 |
| 21 | 9 | 56 |
| 23 | 7 | 38 |
| 24 | 81 | 94 |
| 25 | 10 | 77 |
| 26 | 15 | 42 |
| 27 | 33 | 92 |
| 28a | 25 | 24 |
| 28b | 6 | 14 |
| 29 | 7 | 30 |
| 76 | 3 | 67 |
| 33 | 45 | 96 |
| 35 | 25 | 78 |
| 37 | 24 | 61 |
| 42 | 52 | 54 |
| 43 | 11 | 23 |
| 48 | 35 | 48 |
| 50 | 24 | 50 |
| 54 | 8 | 94 |
| 57 | 20 | 80 |
| 60 | 9 | 37 |
| 62 | 13 | 72 |
| 63 | 17 | 67 |
| 65 | 21 | 48 |
| 66 | 10 | 71 |
| 67 | 59 | 93 |
| 80 | 15 | 63 |
| 90 | 19 | 88 |
| 91 | 16 | 83 |
| 78 | 12 | 92 |
| 31 | 31 | 89 |
| 83 | 12 | 52 |
| 95 | 10 | 71 |

4. Determination of anti-P.A.F. effect in vitro.

Platelet-activating factor (P.A.F.) is a phospholipid mediator which has several effects. The activation of platelet aggregation leads to the induction of protracted broncho contractions and hyperreactivity of the airways.

The effects of the test substances on platelet aggregation induced by adding P.A.F. to a platelet suspension obtained from rabbit blood was investigated by the method described by Mikashima et al. (Jap. J. Pharmacol. 44 (1987) 387-391).

A suspension of platelets originating from rabbit blood was used which contained $4 \times 10^9$ platelets/ml in a modified Tyrode buffer solution adjusted to pH 7.4. Tyrode solution is an aqueous solution containing 136.9 mmol of NaCl, 2.68 mmol of KCl, 2.31 mmol of $CaCl_2$, 1.0 mmol of $MgCl_2$, 11.9 mmol of $NaHCO_3$, 1.45 mmol of $NaH_2PO_4$ and 5.55 mmol of glucose per liter. This solution was modified by adding 1.3 mM/l of $CaCl_2$ and 2.5 g/l of gelatin. The platelets were obtained from 10 ml blood samples from each of three rabbits (New Zealand hybrids, body weight 3-4 kg). For this, the blood samples were treated with ethylenediaminetetraacetic acid and washed by the method of Artley et al. (Brit. J. Hämatol. 19 (1970), 7-17). A platelet-rich plasma was then initially separated by centrifugation (20 minutes at $400 \times g$). The platelets were separated from the plasma by centrifuging again for 15 minutes at $1400 \times g$. After centrifuging, the platelets remaining as a sediment were resuspended in a calcium-free Tyrode buffer solution. 0.4 mmol of lysine acetylsalicylate were then added and after 15 minutes the blood platelets were sedimented again. The sediment was resuspended in the abovementioned modified Tyrode buffer solution, and the number of platelets in the resulting suspension was adjusted to the desired content.

A $40 \times 10^{-9}$ molar P.A.F. solution was used as the reagent. This solution was prepared from a $1.8 \times 10^{-3}$ molar stock solution in chloroform. For this, a 10μl sample of the stock solution was evaporated to dryness and redissolved in 180 μl of the modified Tyrode solution, to which 0.25% of dilapidated bovine serum albumin had been added. $10^{-5}$ molar working solutions were then prepared from this and stored frozen. Samples of these solutions were appropriately diluted for the tests.

To carry out the tests, 50 μl of the platelet solution and 10 μl of a $40 \times 10^{-5}$ molar solution of the compound to be investigated were added to 330 μl of the modified Tyrode buffer solution with stirring (1000 rpm) in an aggregation tube provided with a small magnetic stirrer. This corresponds to a final test substance concentration of $10^{-5}$ mol/l. After a preincubation time of 90 seconds, 10 μl of the P.A.F. preparation were added. The aggregation occurring in the aggregation tubes was measured for 4-5 minutes using a computerized aggregometer.

The aggregation occurring in the test tubes containing only platelet suspension was rated as 0%. The aggregation occurring in test tubes containing platelet suspension and P.A.F. preparation was rated as 100%. The aggregation which still occurred in the presence of the test substances (i.e. during inhibition of the P.A.F.-induced platelet aggregation increase) was measured, and the resulting aggregation inhibition is calculated from this in %.

The results obtained by the foregoing method with the compounds of the formula I are shown in the following Table D.

TABLE D

| Test Substance Example Number | Anti-P.A.F. effect in vitro. % inhibition of the P.A.F.-induced aggregation of platelets from rabbit blood at a test substance concentration of $10^{-5}$ mol/l |
|---|---|
| 1 | 97 |
| 3 | 100 |
| 4 | 58 |
| 7 | 100 |
| 8 | 100 |
| 9 | 73 |
| 10 | 94 |
| 11 | 89 |
| 12 | 100 |
| 13 | 93 |
| 14 | 86 |
| 15 | 85 |
| 16 | 73 |
| 19 | 83 |
| 20 | 17 |
| 21 | 91 |
| 23 | 100 |
| 24 | 80 |
| 25 | 43 |
| 26 | 89 |

TABLE D-continued

| Test Substance Example Number | Anti-P.A.F. effect in vitro. % inhibition of the P.A.F.-induced aggregation of platelets from rabbit blood at a test substance concentration of $10^{-5}$ mol/l |
|---|---|
| 27 | 83 |
| 73 | 99 |
| 76 | 99 |
| 33 | 71 |
| 35 | 56 |
| 37 | 28 |
| 40 | 100 |
| 46 | 91 |
| 47 | 95 |
| 54 | 75 |
| 55 | 40 |
| 56 | 42 |
| 57 | 86 |
| 59 | 89 |
| 60 | 44 |
| 61 | 83 |
| 62 | 70 |
| 63 | 98 |
| 65 | 100 |
| 66 | 100 |
| 67 | 76 |
| 77 | 100 |
| 80 | 72 |
| 85 | 100 |
| 86 | 100 |
| 89 | 100 |
| 90 | 64 |
| 91 | 58 |
| 79 | 71 |
| 78 | 98 |
| 31 | 95 |
| 32 | 100 |
| 83 | 100 |
| 87 | 100 |
| 93 | 100 |
| 96 | 98 |
| 97 | 99 |

5. In vitro determination of cyclooxygenase inhibition and 5-lipoxygenase inhibition.

After activation of the cell, arachidonic acid contained in cell membranes is metabolized in two ways. Leukotrienes, inter alia leukotriene $C_4$, are formed under the action of the enzyme 5-lipoxygenase (5-LO), and prostanoids are formed under the action of the enzyme cyclooxygenase (CO). In in vitro systems, the metabolites are secreted from the cell.

To investigate the cyclooxygenase-inhibiting and the 5-lipoxygenase-inhibiting properties, the inhibitory effect of the test substances on the biosynthesis of the arachidonic acid derivatives leukotriene $C_4$ ($LTC_4$) and 6-ketoprostaglandin $F_1\alpha$ (6-keto-$PGF_1\alpha$) is determined in vitro on mouse peritoneal macrophage cells. This was accomplished by determining the $LTC_4$ and 6-keto-$PGF_1\alpha$ contents in a culture medium of mouse peritoneal macrophage cells by zymosan stimulation as described by Scott et al. (J. Exp. Med. 152 (1980), 324–335) and by Fradin et al. (Prostaglandins, 33 (1987), 579–589).

A cell suspension containing peritoneal cells of male mice 8–10 weeks old was obtained in a known manner. A commercially available cell culture solution (RPMI 1640 from Messrs. Gibco) was used to which heparin (10 international units/ml) and antibiotics were added according to the recipe of Bonney et al. (Biochem. J. 176 (1978) 422–433). The cell suspension was adjusted to a cell concentration of $10^6$ cells per ml and distributed uniformly on titer plates containing 241 ml titer cells (wells). These were kept for two hours in a humidified incubator filled with air enriched with 7% $CO_2$. Cells not adhering to the titer cell walls were then removed by washing. The remaining macrophage cells adhering to the walls were incubated for about 12 hours in a suspension medium to which 0.1% bovine serum albumin (BSA) were added. The suspension medium was then replaced by a Hanks balanced salt solution (HBSS) containing 10 mM Hepes (hydroxyethyl-piperazinoethanesulfonic acid), to which a 0.1% strength solution of the test substances in aqueous, 1% strength dimethylformamide or only the solvent had been added. After 15 minutes the arachidonic acid metabolism was stimulated by adding 10 particles of zymosan (= glycoprotein mixture, isolated from cell walls of beer yeast, *Saccharomyces cerevisiae*, manufactured by Sigma Chemical Co., Munich) per titer cell. After 2 hours, samples of each of the supernatant liquids were investigated for their 6-keto-$PGF_1\alpha$ and $LTC_4$ contents by means of an enzyme immunoassay (EIA) carried out by the method of Pradelles et al. (Analytical Chem. 57 (1985), 1170–1173). The determination of $LTC_4$ and the determination of 6-keto-$PGF_1\alpha$ were each carried out in comparison with a comparative scale on suitable dilutions of the samples (1:50 to 1:250 for the $LTC_4$ determination and 1:250 to 1:1250 for the 6-keto-$PGF_1\alpha$ determination). To determine the inhibitory effect of a $10^{-5}$ molar concentration of the compounds, the amount of reference eicosanoids was determined and the inhibitory effect was calculated from this in % inhibition compared to the measurements of the zymosan controls. The results obtained using this test are shown in the following Table E.

TABLE E

| Test Substance Example Number | In vitro % inhibition effect in zymosan-stimulated mouse peritoneal macrophage cells at a concentration of $10^{-5}$ mol/l on the release of | |
|---|---|---|
| | 6-keto-$PGF_1\alpha$ | $LTC_4$ |
| 1 | 23 | 24 |
| 3 | 20 | 37 |
| 4 | 20 | 44 |
| 7 | 49 | 56 |
| 8 | 74 | 99 |
| 9 | 19 | 62 |
| 12 | 53 | 97 |
| 14 | 25 | 55 |
| 16 | 18 | 17 |
| 19 | 5 | 55 |
| 20 | 42 | 0 |
| 21 | 64 | 95 |
| 23 | 43 | 94 |
| 25 | 24 | 69 |
| 26 | 68 | 89 |
| 27 | 10 | 61 |
| 73 | 29 | 90 |
| 76 | 67 | 75 |
| 33 | 21 | 4 |
| 35 | 51 | 75 |
| 37 | 32 | 13 |
| 39 | 8 | 60 |
| 42 | 76 | 15 |
| 43 | 57 | 24 |
| 47 | 69 | |
| 55 | 41 | 45 |
| 59 | 43 | 80 |
| 61 | 65 | 98 |
| 62 | 64 | 94 |
| 63 | 38 | 98 |
| 65 | 52 | 89 |
| 66 | 72 | 33 |
| 67 | 36 | 66 |
| 77 | 42 | 74 |
| 82 | 58 | 9 |
| 85 | 52 | 62 |
| 81 | 16 | 29 |
| 84 | 46 | 20 |

TABLE E-continued

| Test Substance Example Number | In vitro % inhibition effect in zymosan-stimulated mouse peritoneal macrophage cells at a concentration of $10^{-5}$ mol/l on the release of | |
|---|---|---|
| | 6-keto-PGF$_1\alpha$ | LTC4 |
| 89 | 32 | 51 |
| 90 | 56 | 66 |
| 91 | 54 | 81 |
| 79 | 52 | 71 |
| 83 | 29 | 34 |
| 80 | 12 | 39 |
| 87 | 20 | 23 |

By virtue of their effects described above, the compounds of the formula I are suitable as anti-inflammatory and anti-allergic medicaments for larger mammals, in particular humans, for treating inflammatory and allergic diseases. The orally active compounds of the invention can act in several ways, since they are active against several of the main mediators involved in inflammatory processes and asthmatic complaints.

Due to this activity profile, it can be assumed that in the treatment of allergic-related and non-allergic-related asthma symptoms, the compounds of the invention alleviate not only the symptomatic complaints associated with asthmatic diseases, but may also reduce the associated inflammation. The doses to be used may vary between individuals and vary naturally depending on the type of condition to be treated, the substance used and the form of administration. For example, parenteral formulations generally will contain less active substance than oral preparations. In general, however, pharmaceutical forms containing 10 to 250 mg of active substance per individual dose are suitable for administration to larger mammals, in particular humans.

As medicaments, the compounds of formula I may be formulated with customary pharmaceutical auxiliaries in pharmaceutical preparations, such as, for example, tablets, capsules, suppositories or solutions. These pharmaceutical preparations can be produced by known methods using customary solid excipients such as, for example, lactose, starch or talc or liquid paraffins and using customary pharmaceutical auxiliaries, for example tablet disintegrating agents, solubilizers and/or preservatives.

The following examples are intended to illustrate the invention in greater detail without restricting its scope.

The structure of each novel substance was confirmed by spectroscopic investigation, in particular by an analysis of the IR and NMR spectra, and also by elemental analysis. The purity of the intermediates was monitored by thin layer chromatography.

EXAMPLE 1

5,6-Dihydro-2-methyl-1-{2-[4-(4-methylpyridin-2-yl)piperazin-1-yl]ethyl}-4H-pyrrolo[3,2,1-ij]quinoline A) 266.4 g of 1,2,3,4-tetrahydroquinoline were added to a mixture of 330 ml of 12 N hydrochloric acid and 800 g of ice. A solution of 165 g of sodium nitrite in 500 ml of water was added slowly to the mixture over the course of 2 hours while the temperature was kept below 5° C. The reaction mixture was then allowed to warm to room temperature in the course of hour and was extracted twice with 500 ml portions of toluene. The organic phase was separated, washed four times with 300 ml portions of water, dried and evaporated. As a residue, 269 g of crude 1,2,3,4-tetrahydro-1-nitrosoquinoline were obtained as a brownish oil.

B) 50.5 g of lithium aluminum hydride were slowly added to one liter of tetrahydrofuran cooled to about 5° C., and the temperature was maintained between 5° and 10° C. during the addition. The mixture was then allowed to warm to a temperature of approximately 15° C. Over a period of 4 hours, a solution of 108 g of the 1,2,3,4-tetrahydro-1-nitroso-quinoline obtained above in 500 ml of tetrahydrofuran was added to the reaction mixture while maintaining the temperature between 15° and 20° C. The reaction mixture was then kept at room temperature for a further 1½ hours. To work up the reaction mixture it was then cooled to 5° C. and hydrolyzed by adding first a mixture of 50 ml of water and 50 ml of tetrahydrofuran, then 50 ml of 15% strength aqueous sodium hydroxide solution and a further 50 ml of water. The resulting precipitate was then filtered out and washed with dichloromethane. The combined filtrates were concentrated and the residue which remained was dissolved in dichloromethane. The resulting solution was washed with water, dried and evaporated. 85.1 g of crude 1-amino-1,2,3,4-tetrahydroquinoline were obtained as a brownish oil.

C) 85 g of the product obtained above were heated under reflux for 1 hour at a temperature of 80° C. in a mixture of 99.2 g of ethyl levulinate (ethyl 3-acetylpropionate), 852 ml of acetic acid and 52.5 ml of 12N hydrochloric acid. The reaction mixture was then cooled to 50° C., organic solvent was largely evaporated, and 200 ml of water were added. The aqueous reaction mixture was neutralized with saturated sodium bicarbonate solution and extracted with dichloromethane. The dichloromethane phase was separated, washed with water, dried over sodium sulfate, filtered and evaporated. As a residue, 159.9 g of a tarry brownish crude product were obtained. This was dissolved in ethanol containing 2% toluene and purified by chromatography on a small silica gel column using toluene/ethanol 98:2 as the eluent. The eluate running out of the column was evaporated, and the residue which remained, which besides ethyl 5,6-dihydro-2-methyl-4H-pyrrolo[3,2,1-ij]quinoline-1-acetate also contained admixtures of the corresponding acid, was dissolved in 200 ml of dichloromethane. The solution was washed with 10% strength aqueous sodium hydroxide solution to remove acidic contents. It was then washed with water until neutral, and the organic phase was separated, dried over sodium sulfate and evaporated. 118.8 g of crude ethyl 5,6-dihydro-2-methyl-4-pyrrolo[3,2,1-ij]quinoline-1-acetate were obtained as a brownish oil.

D) 17.4 g of lithium aluminum hydride were added to 500 ml of tetrahydrofuran cooled to about 5° C. The temperature was then allowed to rise to about 15° C., and a solution of 59 g of the ester obtained above in 500 ml of tetrahydrofuran was slowly added, divided over a period of 3 hours while keeping the temperature below 22° C. The reaction mixture was then allowed to react at room temperature for a further hour. To work up the reaction mixture it was cooled to about 5° C. and first a mixture of 17 ml water and 17 ml of tetrahydrofuran, then 17 ml of 15% strength aqueous sodium hydroxide solution and a further 17 ml of water were added for hydrolysis. The precipitate which formed was then filtered out and washed with dichloromethane. The organic filtrates were concentrated, the residue was taken up in dichloromethane, and the dichloromethane phase was washed with water, dried and evaporated. 44.3 g of 5,6-dihydro-1-(2-hydroxyethyl)-2-methyl-4H- pyrrolo[3,2,1-ij]quinoline were obtained as a yellowish powder.

E) A solution of 44 g of the product obtained above in 250 ml of chloroform was cooled to a temperature of 10° to 15° C. A solution of 41.5 g of phosphorus tribromide in 85 ml of chloroform was slowly added, and the reaction mixture was heated under reflux for 1 hour. To work up the reaction mixture it was hydrolyzed by introducing it into an ice/water mixture and then it was extracted with chloroform. The organic phase was separated, washed with 100 ml of 10% strength aqueous sodium bicarbonate solution and then with water, dried and concentrated. As a residue, 62.8 g of a brownish oil were obtained. This was recrystallized from absolute alcohol to obtain 33.7 g of 1-(2-bromoethyl)-5,6-dihydro-2-methyl-4H-pyrrolo[3,2,1,-ij]quinoline as a creamy white powder.

F) 10 g of the product obtained above, 7.64 g of 1-(4-methylpyridin-2-yl)piperazine, 0.6 g of potassium iodide and 10.1 ml of triethylamine were heated under reflux at 90° C. in 100 ml of dimethylformamide for 1½ hours. To work up the reaction mixture it was evaporated, the residue which remained was taken up in water, and the mixture was extracted with dichloromethane. The dichloromethane phase was separated, washed with 10% strength aqueous sodium hydroxide solution, then washed with water until neutral and concentrated. As a residue, 14.6 g of the crude title compound remained as a brownish oil. This was purified by chromatography on a small silica gel column using initially toluene and later toluene/ethanol 95:5 as the eluent. 9.7 g of solid 5,6-dihydro-2-methyl-1-{2-[4-methylpyridin-2-yl]piperazin-1-yl]ethyl}-4H-pyrrolo[3,2,1-ij]quinoline were obtained.

For conversion to the corresponding trihydrochloride, the title base obtained above was dissolved in isopropanol. Isopropanolic 2.3N hydrochloric acid was added to the isopropanolic solution of the title compound, whereupon the trihydrochloride of the title compound crystallized out. The resulting 5,6-dihydro-2-methyl-1-{2-[4-(4-methylpyridin-2-yl)piperazin-1-yl]ethyl)}-4H-pyrrolo[3,2,1-ij]quinoline trihydrochloride had a melting point of 254° C.

EXAMPLE 2

5,6-Dihydro-2-methyl-1-{2-[4-(4-fluorobenzoyl)piperidin-1-yl]-ethyl}-4H-pyrrolo[3,2,1-ij]quinoline A) 100 g of piperidine-4-carboxylic acid were heated under reflux and with stirring at a temperature of 135° C. for 4 hours in 400 ml of acetic anhydride. The mixture was then allowed to cool to room temperature. To work up the reaction mixture it was evaporated to remove acetic anhydride, toluene being added several times towards the end of the evaporation. After the evaporation a beige-colored solid crude product remained as a residue. This was suspended in 300 ml of a mixture of diisopropyl ether and dichloromethane, cooled to a temperature of 0° C. and filtered. 65 g of crude acetylpiperidine-4-carboxylic acid having a melting point of 180° to 182° C. were obtained. The filtrate was diluted while hot with 200 ml of water, and further 1-acetylpiperidine-4-carboxylic acid deposited as a precipitate and was filtered out. 42.91 g of the acid were obtained, so that the total yield of 1-acetylpiperidine-4-carboxylic acid was 107.9 g.

B) 40 g of the acid obtained above were heated under reflux in 200 ml of sulfonyl chloride. After 15 minutes, a brown coloration occurred, and the solution was cooled and allowed to react at room temperature for a further 2 hours. The sulfonyl chloride was then removed by evaporation, and the brownish-red solid which remained was washed first with toluene and then with petroleum ether and dried under reduced pressure. 49 g of crude 1-acetylpiperdine-4-carbonyl chloride were obtained.

C) 26 g of aluminum chloride were added to 50 ml of fluorobenzene. 19 g of the acid chloride obtained above were added to the mixture in small portions. The reaction mixture was then heated to the reflux temperature of fluorobenzene for 3 hours. The reaction was then stopped by addition of ice. The reaction mixture was extracted with chloroform, and the chloroform phase was separated, washed with water and concentrated. 18.33 g of crude 1-acetyl-4-(4-fluorobenzoyl)-piperidine were obtained.

D) 18 g of the product obtained above were heated under reflux for 3 hours in a mixture of 120 ml of 12N hydrochloric acid and 80 ml of water. Some dichloromethane was then added, and the reaction mixture was rendered alkaline by addition of sodium hydroxide solution while cooling in an ice-bath. It was then extracted with dichloromethane, and the dichloromethane phase was washed with water, dried and concentrated. 15.68 g of crude product were obtained. This was dissolved in toluene, then 25 ml of isopropanol saturated with hydrogen chloride were added. The resulting beige-colored precipitate was filtered out and dried. 11.31 g of 4-(4-fluorobenzoyl)piperidine hydrochloride were obtained as a grey-colored powder.

E) 5.78 g of the above product, 6 g of 1-(2-bromoethyl)5,6-dihydro-2-methyl-4H-pyrrolo[3,2,1-ij]quinoline and 9.0 ml of triethylamine were heated under reflux in 50 ml of toluene, a creamy white precipitate gradually being formed. After 8 hours, a further 2 ml of triethylamine were added and later also a few crystals of finely powdered potassium iodide. Altogether, the reaction mixture was heated for 32 hours. To work up the reaction mixture it was diluted with 500 ml of dichloromethane, washed with water, dried and evaporated to dryness. 9.83 g of crude product were obtained. From this, 4.64 g of crude title compound were obtained after chromatographic purification on silica gel. After recrystallization from isopropanol, 3.96 g of 5,6-dihydro-2-methyl-1-{2-[4-(4-fluorobenzoyl)piperidin-1-yl]-ethyl}-4-H-pyrrolo[3,2,1-ij]quinoline having a melting point of 124°–125° C. were obtained.

EXAMPLE 3

5,6-Dihydro-2-methyl-4-phenyl-{2-[4-(4-methylpyridin-2-yl)piperazin-1-yl]ethyl}-4H-pyrrolo[3,2,1-ij]quinoline A) 30 g of quinoline were dissolved in 100 ml tetrahydrofuran. The solution was cooled to 2° C., then 19.6 g of phenyllithium in the form of a 2M solution in a 70:30 mixture of cyclohexane and diethyl ether were added over the course of 2 hours while the temperature was maintained between 0° and 2° C. The reaction mixture was then allowed to warm to room temperature. To work up the reaction mixture it was added to water and then extracted with diethyl ether. The ether phase was washed with water until neutral, dried and concentrated. 50 g of crude product were obtained, which was purified by chromatography on a silica gel column using toluene as the eluent. 20.3 g of 1,2-dihydro-2- phenylquinoline having a melting point of 75° C. were obtained.

B) 2 g of the product obtained above were heated under reflux with stirring in 40 ml of ethanol. In the course of this, a total of 4 g of metallic sodium were added in portions to the reaction mixture over the course of 2 hours. To work up the reaction mixture it was added to 200 ml of ice-water, then extracted with ether, and the ether phase was washed with water until neutral, dried and concentrated. As a residue, 1.6 g of crude oily 1,2,3,4-tetrahydro-2-phenyl-quinoline remained.

C) 30 g of the product obtained above were reacted with 11.38 g of sodium nitrite analogously to Example 1A). The reaction mixture was worked up as described in Example 1A). 32.5 g of oily crude 1,2,3,4-tetrahydro-1-nitroso-2-phenylquinoline were obtained.

D) 32 g of the product obtained above were reduced by the method described in Example 1B) using 15.25 g of lithium aluminum hydride in tetrahydrofuran. The reaction mixture was worked up as described in Example 1B). 28.2 g of crude 1-amino-1,2,3,4-tetrahydro-2-phenylquinoline were obtained as an orange-colored oil.

E) 28 g of the product obtained above were heated under reflux at a temperature of 80° C. for 2 hours with 21.6 g of ethyl levulinate in a mixture of 187.5 ml of acetic acid and 12.5 ml of 12N hydrochloric acid. The reaction mixture was worked up by cooling it, removing organic solvent by evaporation, taking up the residue in 100 ml of water, neutralizing the aqueous phase by adding sodium bicarbonate and then extracting twice with 100 ml portions of toluene. The toluene phase was washed with water, dried and concentrated. 36.6 g of oily crude product remained. For further purification, this was chromatographed on a silica gel column using toluene/ethanol 9:1 as the eluent. In this way, 26.6 g of a brownish oil were obtained which was further separated by repeated chromatography on a silica gel column using toluene/ethanol 9.8:0.2 as the eluent. 10 g of pure ethyl 5,6-dihydro-2-methyl-4-phenyl-4H-pyrrolo[3,2,1-ij]quinoline acetate were obtained. In addition, a further 12.8 g of a mixture of this ester with the corresponding acid were obtained. To complete esterification, this mixture was heated under reflux for 2½ hours in ethanol with the addition of sulfuric acid. The reaction mixture was worked up by removing the ethanol by evaporation, then adding water and extracting the mixture with ethyl acetate. The organic phase was washed with water, dried and concentrated. The residue which remained consisted of pure ethyl 5,6-dihydro-2-methyl-4-phenyl-4H-pyrrolo[3,2,1-ij]-quinoline-1-acetate.

F) 19.2 g of the product obtained above were reduced in tetrahydrofuran with a total of 9.5 g of lithium aluminum hydride using the method described in Example 1D) except the reaction mixture was heated under reflux for 3 hours. To work up the reaction mixture it was cooled and, for hydrolysis, first 9.5 ml of water, then 9.5 ml of 15% strength aqueous sodium hydroxide solution and a further 9.5 ml of water were added. The resulting precipitate was then filtered out, and the filter residue was washed again with ether. The filtrates were concentrated. The residue which remained was taken up in ether, and the organic phase was washed with water, dried and concentrated. 13.7 g of crude 5,6-dihydro-1-(2-hydroxyethyl)-2-methyl-4-phenyl-4H-pyrrolo[3,2,1-ij]quinoline were obtained as a yellow oil.

G) 13.6 g of the alcohol obtained above were reacted with 9.37 g of phosphorus tribromide in 80 ml of chloroform by the method described in Example 1E), and the reaction mixture was worked up as described in Example 1E). 16.4 g of 1-(2-bromoethyl)-5,6-dihydro-2-methyl-4-phenyl-4H-pyrrolo[3,2,1-ij]quinoline were obtained as an oil, which then crystallized.

H) 8 g of the product obtained above, 4.8 g of 1-(4-methylpyridin-2-yl)piperazine and 6.3 ml of triethylamine were heated under reflux for 12 hours in 60 ml of dimethylformamide. The reaction mixture was worked up by adding 100 ml of 20% strength aqueous hydrochloric acid. The reaction mixture was then neutralized by addition of sodium bicarbonate and extracted with dichloromethane. The organic phase was washed with water until neutral, dried and evaporated. 9 g of crude oily title compound were obtained. For conversion to the corresponding hydrochloride, the title compound was dissolved in 20 ml of isopropyl alcohol and 19 ml of 2.1 molar isopropanolic hydrochloric acid solution were added to the solution. The resulting precipitate was filtered out and recrystallized from absolute alcohol and a little water. 5.4 g of 5,6-dihydro-2-methyl-4-phenyl-1-{2-[4-(4-methylpyridine-2-yl)piperazin-1-yl]-ethyl}-4H-pyrrolo[3,2,1-ij]quinoline 2.2 HCl 0.3 H₂O having a melting point of 216° C. were obtained.

EXAMPLE 4

5,6-Dihydro-4-n-heptyl-2-methyl-1-{2-[4-(4-methyl-pyridin-2yl)piperazin-1-yl]ethyl}-4H-pyrrolo[]3,2,1-ij]quinoline A) A solution of 25 g of 2-methylquinoline in 40 ml of ether was added slowly to a mixture of 70 ml of a 1.6M solution of n-butyllithium in hexane and 40 ml of diethyl ether. The reaction mixture was stirred at room temperature, then it was cooled to about 5° C. and a solution of 28.9 g of n-hexyl bromide in 10 ml of ether was slowly added. The reaction mixture was then warmed to room temperature and stirred at room temperature for 2 hours. For working-up, the reaction mixture was added to 500 ml of water and extracted with ether. The organic phase was washed with slightly acidified water, dried and evaporated. The crude product obtained was purified by chromatography on a silica gel column using dichloromethane as the eluent. 31 g of oily crude 2-n-heptylquinoline were obtained.

B) 31 g of the product obtained above were dissolved in 300 ml of acetic acid. 18 g of sodium cyanoborohydride were gradually added to the solution over the course of 20 minutes. The temperature in this case rose to about 28° C. The reaction mixture was stirred at this temperature for a further 12 hours. To work up the reaction mixture 800 ml of 10 N aqueous sodium hydroxide solution were added with cooling by addition of ice. The reaction mixture was then extracted with ethyl acetate. The organic phase was washed with water until neutral, dried and evaporated. As a residue, 25.5 g of crude oily 2-n-heptyl-1,2,3,4-tetrahydroquinoline remained.

C) 25.5 g of the product obtained above were reacted with 9.2 g of sodium nitrite in aqueous hydrochloric acid medium analogously to Example 1A). The reaction mixture was worked up as described in Example 1A). 25.1 g of crude, oily 2-n-heptyl-1-nitroso-1,2,3,4-tetrahydroquinoline were obtained.

D) 25 g of the product obtained above were reduced in tetrahydrofuran using 7.3 g of lithium aluminum hydride as described in Example 1B). The reaction mixture was worked up as described in Example 1B). 18.5 g of crude, oily 1-amino-2-n-heptyl-1,2,3,4-tetrahydroquinoline were obtained.

E) 18.5 g of the above product were heated under reflux at 80° C. for 3 hours with 13 g of ethyl levulinate in a mixture of 120 ml of glacial acetic acid and 7.2 ml of 12N hydrochloric acid. To work up the reaction mixture it was cooled, then organic solvents were removed by evaporation. Aqueous sodium hydroxide solution and ethyl acetate were then added to the reaction mixture The organic phase was separated, washed with water until neutral, dried and concentrated. As a residue, 20 g of oily crude product were obtained. This crude ester was dissolved in 100 ml of ethanol. A solution of 8 g of potassium hydroxide in 100 ml of ethanol was added to the solution and the reaction mixture was heated under reflux for 2 hours to hydrolyze the ester. The ethanol was then evaporated, the residue was dissolved in water and the aqueous phase was washed with diethyl ether, acidified and extracted with ethyl acetate. The ethyl acetate phase was washed with water, dried and evaporated. The crude acid which remained as an oily residue was heated under reflux for 2 hours in 100 ml of ethanol with the addition of a few drops of sulfuric acid for reesterification. The excess alcohol was then removed by evaporation, and the residue was taken up in water and extracted with ethyl acetate. The organic phase was washed, dried and concentrated. 3.2 g of ethyl 4-n-heptyl-5,6-dihydro-2-methyl-4H-pyrrolo[3,2,1-ij]quinoline-1-acetate were obtained.

F) 3.2 g of the ester obtained above were reduced by the method described in Example 1D) using 1 g of lithium aluminum hydride in tetrahydrofuran. The reaction mixture was then worked up as described in Example 1D). 2.6 g of crude 4-n-heptyl-5,6-dihydro-1-(2-hydroxyethyl)-2-methyl-4H-pyrrolo-[3,2,1-ij]-quinoline were obtained as an oil, which slowly crystallized G) 2.6 g of the product obtained above were reacted with 1.68 g of phosphorus tribromide in chloroform by the method described in Example 1E). The reaction mixture was worked up as described in Example 1E). 2.7 g of crude product were obtained. This was purified by chromatography on a silica gel acid using dichloromethane as the eluent. In this way, 2 g of 1-(2-bromoethyl)-4-n-heptyl-5,6-dihydro-2-methyl-4H-pyrrolo[3,2,1-ij]quinoline were obtained.

H) 2 g of the product obtained above were heated under reflux for 6 hours with 1.2 g of 1-(4-methylpyridin-2-yl)piperazine and 1.07 g of triethylamine in 25 ml of dimethylformamide. The reaction mixture was then worked up as described in Example 1F). 2 g of crude product were obtained. This was purified by chromatography on a silica gel column using dichloromethane as the eluent. 0.6 g of 4-n-heptyl-5,6-dihydro-2-methyl-1-{2-[4-(4-methylpyridin-2-yl)piperazin-1-yl]ethyl}-4H-pyrrolo[3,2,1-ij]-quinoline were obtained. This was converted into the dihydrochloride by the method described in Example 1F). After concentration of the isopropanolic solution, 0.45 g of meringue-colored 4-n-heptyl-5,6-dihydro-2-methyl-1-{2-[4-(4-methylpyridin-2-yl)piperazin-1-yl]ethyl}-4H-pyrrolo[3,2,1-ij]quinoline dihydrochloride having a melting point of 150° C. was obtained.

EXAMPLE 5

5,6-Dihydro-8-methoxy-2-methyl-1-{2-[4-(4-methylpyridin-2-yl)piperazin-1-yl]ethyl}-4H-pyrrolo[3,2,1-ij]quinoline A) 51 g of 6-methoxyquinoline were dissolved in 500 ml of acetic acid. 63.4 ml (58.37 g) of diborane/pyridine complex were added dropwise to the solution without any rise in temperature. The reaction mixture was stirred at room temperature for a total of about 30 hours. Additional 32 ml portions of diborane/pyridine complex were added after 7 hours and after 27 hours. The reaction mixture was worked up by adding 750 ml of aqueous sodium hydroxide solution and 500 ml of water with cooling, and the mixture was then extracted twice with 500 ml portions of toluene. The organic phase was concentrated. To destroy residual borane complex, the residue was taken up in 250 ml of aqueous 6N hydrochloric acid and left in the hydrochloric acid solution for 12 hours. 250 ml of 10% strength aqueous sodium hydroxide solution were then added with cooling in order to render the reaction mixture alkaline. It was then extracted with toluene, and the organic phase was separated, washed with water and sodium chloride solution until neutral, dried and evaporated. 36.6 g of crude 1,2,3,4-tetrahydro-6-methoxyquinoline remained as a yellowish oil.

B) 36 g of the compound obtained above were reacted with 18.2 g of sodium nitrite in aqueous hydrochloric acid solution by the method described in Example 1A), and the reaction mixture was worked up as described in Example 1A). 29.5 g of crude 6-methoxy-1,2,3,4-tetrahydro-1-nitrosoquinoline were obtained as a red oil.

C) 29.5 g of the product obtained above were reduced by the method described in Example 1B) using 11.65 g of lithium aluminum hydride in tetrahydrofuran. The reaction mixture was worked up as described in Example 1B). 26 g of crude 1-amino-1,2,3,4-tetrahydro-6-methoxyquinoline were obtained as a brownish-red oil.

D) 26 g of the product obtained above were heated under reflux at 80° C. for 1 hour with 25.75 g of ethyl levulinate in a mixture of 220 ml of acetic acid and 13.3 ml of 12N hydrochloric acid. To work up the reaction mixture it was concentrated to remove organic solvents and then treated with water and dichloromethane. The organic phase was separated and washed with water until neutral. The organic phase was then washed with a mixture of 10 ml of concentrated sodium hydroxide solution and 200 ml of water to remove acid. The organic phase was then washed with water until neutral, dried and concentrated. As a residue, 33.2 g of dark, oily, partly crystallized crude product remained. This was purified by chromatography on a small silica gel column using dichloromethane as the eluent. 22 g of a red-orange oil were obtained, which was recrystallized from hexane. In this way, 13.9 g of ethyl 5,6-dihydro-8-methoxy-2-methyl-4H-pyrrolo[3,2,1-ij]quinoline-1-acetate were obtained as a beige-colored powder.

E) 13.4 g of the product obtained above were reduced by the method described in Example 1D) using 3.4 g of lithium aluminum hydride in tetrahydrofuran. The reaction mixture was worked up as described in Example 1D). 10.7 g of 1-(2-hydroxyethyl)-8-methoxy-2-methyl-5,6-dihydro-4H-pyrrolo-[3,2,1-ij]quinoline were obtained as a pale yellow powder.

F) 10.5 g of the product obtained above were reacted with 11.6 g of phosphorus tribromide in chloroform by the process described in Example 1E). The reaction mixture was worked up as described in Example 1E). 13.1 g of 1-(2-bromoethyl)-8-methoxy-2-methyl-5,6-dihydro-4H-pyrrolo[3,2,1-ij]quinoline were obtained as a grey powder.

G) 13 g of the product obtained above were heated under reflux at a temperature of 80°-85° C. for 3 hours with 8.97 g of 1-(4-methylpyridin-2-yl)piperazine, 11.8 ml of triethylamine and 0.7 g of potassium iodide in 180 ml of dimethylformamide. The reaction mixture was worked up as described in Example 1F). 10.1 g of pale beige 8-methoxy-2-methyl-1-(2-[4-(4-methylpyridin-2-yl)piperazin-1-yl]ethyl}-5,6-dihydro-4H-pyrrolo[3,2,1-ij]quinoline having a melting point of 104° C. were obtained.

EXAMPLE 6

8-Hydroxy-2-methyl-1-{2-[4-(4-methylpyridin-2-yl)-piperazin-1-yl]ethyl}-5,6-dihydro-4H-pyrrolo[3,2,1-ij]quinoline 7.9 g of 8-hydroxy-2-methyl-1-{2-[4-(4-methylpyridin-2-yl)piperazin-1-yl]ethyl}-5,6-dihydro-4H-pyrrolo[3,2,1-ij]quinoline (preparation see Example 5) were dissolved in 110 ml of dichloromethane. The solution was cooled to −10° C. A solution of 24.42 g of boron tribromide in 35 ml of dichloromethane was then added while the temperature was kept between −10° and 0° C. The mixture was allowed to react at about 0° C. for 30 minutes. To work up the reaction mixture it was added to a mixture of ice and saturated aqueous sodium bicarbonate solution. The organic phase was separated from the alkaline aqueous phase, washed until neutral, dried and evaporated. As a residue, 9.3 g of a pale grey, solid crude product remained, which was purified by chromatography on a small silica gel column. 4.4 g of cream-colored 8-hydroxy-2-methyl-1-{2-[4-(4-methyl-pyridin-2-yl) piperazin-1-yl]ethyl}-5,6-dihydro-4H-pyrrolo[3,2,1-ij]quinoline having a melting point of 110° C. were obtained.

EXAMPLE 7

2-(4-Methoxyphenyl)-1-{2-[4-methylpyridin-2-yl)piperazin-1-yl]ethyl-5,6-dihydro-4H-pyrrolo[3,2,1-ij]quinoline A) 21 g of 3-(4-methoxybenzoyl)propionic acid were heated under reflux for 5¼ hours in 350 ml of ethanol after addition of 7.3 ml of concentrated sulfuric acid The reaction mixture was worked up by concentrating it, taking up the remaining residue in 100 ml of water and extracting the mixture with dichloromethane. The organic phase was separated, washed with 50 ml of saturated aqueous sodium bicarbonate solution, then washed with water until neutral, dried and concentrated. 23.3 g of crude ethyl 3-(4-methoxybenzoyl)-propionate were obtained as a yellowish, crystallizing oil.

B) 11 g of 1-amino-1,2,3,4-tetrahydroquinoline (preparation see Example 1B) and 21.04 q of the ester obtained above were heated under reflux for 3 hours in a mixture of 110 ml of acetic acid and 6.80 ml of 12N hydrochloric acid. To work up the reaction mixture it was concentrated, and 37.15 g of a red oil were obtained. This was taken up in water and the aqueous phase was extracted with dichloromethane. The organic phase was separated, washed with 20 ml of 10% strength aqueous sodium hydroxide solution, then washed with water, dried and evaporated. 25.5 g of a crude oily mixture of 2-(4-methoxyphenyl)-5,6-dihydro-4H-pyrrolo[3,2,1-ij]-quinoline-1-acetic acid and its ethyl ester were obtained. The mixture was added to isopropyl ether. 6.4 g of the acid crystallized as an ochre-colored powder and were filtered out. The filtrate was separated by column chromatography on silica gel using toluene, and 3,6 g of the ester and 1.3 g of the acid were obtained. The whole 7.7 g of the acid were esterified with ethanol to yield 8 g of the ester.

C) 11 g of the ester obtained above were reduced as described in Example 1D) using 2.39 of lithium aluminum hydride in tetrahydrofuran. The reaction mixture was worked up as described in Example 1D). 7.6 g of crude 1-(2-hydroxyethyl)-2-(4-methoxyphenyl)-5,6-dihydro-4H-pyrrolo[3,2,1-ij]quinoline were obtained as a brownish, crystallizing oil.

D) 7.5 g of the product obtained above were reacted with 4.95 g of phosphorus tribromide in chloroform by the method described in Example 1E). The reaction mixture was worked up as described in Example 1E). 8 g of 1-(2-bromoethyl)-2-(4-methoxyphenyl)-5,6-4H-pyrrolo[3,2,1-ij]quinoline were obtained as a brownish powder.

E) 7.5 g of the above product were heated under reflux at a temperature of 85°-90° C. for 5 hours with 4.3 g of 1-(4-methylpyridin-2-yl)piperazine, 4.10 g of triethylamine and 0.34 g of potassium iodide in 50 ml of dimethylformamide. The reaction mixture was worked up by concentrating it to dryness, dissolving the remaining residue in dichloromethane and washing the dichloromethane solution first with water, then with saturated, aqueous sodium bicarbonate solution and finally again with water until neutral, after which it was dried and concentrated. 10.07 g of crude product were obtained, which was purified by chromatography on a silica gel column using first toluene and then toluene/ethanol 98:2 as the eluent. A yellowish oil was obtained which was crystallized from isopropanol. After drying, 4.0 g of 2-(4-methoxy-phenyl)-1-{2-[4-(4-methylpyridin-2-yl)piperazin-1-yl]ethyl}-5,6-dihydro-4H-pyrrolo[3,2,1-ij]quinoline having a melting point of 120° C. were obtained.

EXAMPLE 8

2-(4-Hydroxyphenyl)-1-{2-[4-(4-methylpyridin-2-yl)-piperazin-1-yl)ethyl}-5,6-dihydro-4H-pyrrolo[3,2,1-ij]quinoline 7.5 g of 2-(4-methoxyphenyl)-1-{2-[4-(4-methylpyridin-2-yl)piperazin-1-yl]ethyl}-5,6-dihydro-4H-pyrrolo[3,2,1-ij]quinoline (preparation see Example 7) were dissolved in 110 ml of acetic acid. 110 ml of 41% strength aqueous hydrobromic acid were added to the solution, and the reaction mixture was heated under reflux for 16 hours. To work up the reaction mixture it was cooled to room temperature, then diluted with 100 ml of water and neutralized by addition of 10% strength aqueous sodium hydroxide solution (pH=6). It was then extracted with dichloromethane, and the organic phase was separated, dried and concentrated. The oily residue which remained was crystallized from ethanol/ether. 5.2 g of 2-(4-hydroxyphenyl)-1-{2-[4-(4-methylpyridin-2-yl)piperazin-1-yl]ethyl}-5,6-dihydro-4H-pyrrolo[3,2,1-ij]quinoline having a melting point of 220° C. were obtained.

EXAMPLE 9

8-Bromo-2-methyl-1-{2-[4-(4-methylpyridin-2-yl)piperazin-1-yl]ethyl}-5,6-dihydro-4H-pyrrolo[3,2,1-ij]quinoline A) 5 g of 1-(2-bromoethyl)-5,6-dihydro-2-methyl-4H-pyrrolo[3,2,1-ij]quinoline (preparation see Example 1E) were dissolved in 20 ml of acetic acid. A solution of 3.4 g of bromine in 10 ml of acetic acid was added to the solution and the reaction mixture was stirred at room temperature for 2 hours. The reaction mixture was worked up by adding it to ice, neutralizing it by adding 20% strength aqueous sodium hydroxide solution and extracting it with dichloromethane. The organic phase was washed with water until neutral, dried and concentrated. As a residue, 6 g of oily crude product were obtained, which was purified by chromatography on a silica gel column using dichloromethane as the eluent. 3.8 g of 8-bromo-1-(2-bromoethyl)-2-methyl-5,6-dihydro-4H-pyrrolo[3,2,1-ij]quinoline were obtained.

B) 3.8 g of the product obtained above were reacted with 1.85 g of 1-(4-methylpyridin-2yl)piperazine in dimethylformamide with the addition of 1.86 g of triethylamine by the method described in Example 7E). The reaction mixture was worked up as described in Example 7E). 1.0 g of oily, crude 8-bromo-2-methyl-1-{2-[4-(4-methylpyridin-2-yl)piperazin-1-yl]ethyl}-5,6-dihydro-4H-pyrrolo[3,2,1-ij]quinoline was obtained. This was converted into its trihydrochloride as described in Example 1F). 500 mg of the trihydrochloride of the title compound having a melting point of 200° C. (decomposition) were obtained

EXAMPLE 10

2-Methyl-8-nitro-1-{2-[4-(4-methylpyridin-2-yl)-piperazin-1-yl]ethyl}-5,6-dihydro-4H-pyrrolo[3,2,1-ij]quinoline A) 5 g 1-(2-bromoethyl)-2-methyl-5,6-dihydro-4H-pyrrolo[3,2,1-ij]quinoline were added to 10 ml of concentrated sulfuric acid cooled to 0° C. The reaction mixture was kept at a temperature of about 0° C., and a mixture of 1.15 ml of concentrated sulfuric acid and 0.84 ml of nitric acid was added dropwise as a nitrating agent. The reaction mixture was kept for a further hour at 0° C. and one more hour at room temperature. To work up the reaction mixture it was poured onto 30 g of ice and extracted with dichloromethane. The organic phase was dried and concentrated. The residue which remained was heated in 10 of ethanol, and the resulting yellowish precipitate was filtered out. 2.26 g of 1-(2-bromoethyl)-2-methyl-8-nitro-5,6-dihydro-4H-pyrrolo[3,2,1-ij]quinoline were obtained as an ochre-colored powder.

B) 3.1 g of the product obtained above were reacted with 2.04 g of 1-(4-methylpyridin-2-yl) piperazine in dimethylformamide with the addition of 2.69 ml of triethylamine and 0.16 g of potassium iodide by the method described in Example 7E). The reaction mixture was worked up as described in Example 7E). 1.5 g of crude 2-methyl-8-nitro-1-{2-[4-(4-methylpyridin-2-yl)piperazin-1-yl]ethyl}-4H-pyrrolo[3,2,1-ij]quinoline were obtained as a brownish oil. This was converted into the hydrochloride as described in Example 3H). 1.18 g of 2-methyl-8-nitro-1-{2-[4-(4-methylpyridin-2-yl)piperazin-1-yl]ethyl}-5,6-dihydro-4H-pyrrolo[3,2,1-ij]quinoline 1.6 HCl 1.5 H$_2$O having a melting point of 230° C. were obtained.

EXAMPLE 11

5-Methyl-6-{2-[4-(4-methylpyridin-2-yl)piperazin-1-yl]ethyl}-2,3-dihydro-pyrrolo[1,2,3-de]-1,4-benzo-thiazine A) 25.3 g of lithium aluminum hydride were suspended in 500 ml of tetrahydrofuran and the reaction mixture was cooled in an ice bath to a temperature of 15°-20° C. A solution of 33 g of 2H,4H-1,4-benzothiazin-2-one in 400 ml of tetrahydrofuran was then added, and the reaction mixture was heated under reflux for hour. The reaction mixture was then worked up by the method described in Example 1B). 26 g of 2H-3,4-dihydro-1,4-benzothiazine were obtained.

B) 26 g of the product obtained above were reacted with sodium nitrite in aqueous hydrochloric acid solution by the method described in Example 1A), and the reaction mixture was worked up as described in Example 1A). 31 g of 2H-3,4-dihydro-4-nitroso-1,4-benzothiazine were obtained.

C) 31 g of the nitroso product obtained above were reduced by the method described in Example IB) using 19.6 g of lithium aluminum hydride in tetrahydrofuran. The reaction mixture was worked up as described in Example 1B). 25.4 g of oily 4-amino-2H-3,4-dihydro-1,4-benzothiazine were obtained.

D) 25.4 g of the product obtained above were reacted with 26.3 g of ethyl levulinate by the method described in Example 1C). The reaction mixture was worked up as described in Example 1C). 9.7 g of ethyl 5-methyl-2,3-dihydro-pyrrolo[1,2,3-de]-1,4-benzothiazine-6-acetate were obtained.

E) 4 g of lithium aluminum hydride were suspended in 150 ml of tetrahydrofuran. A solution of 9.7 g of the ester obtained above in 200 ml of tetrahydrofuran was added to the suspension and the reaction mixture was heated under reflux for 1 hour. The reaction mixture was then worked up as described in Example 1D). 7.1 g of 6-(2-hydroxyethyl)-5-methyl-2,3-dihydropyrrolo[1,2,3-de]-1,4-benzothiazine were obtained.

F) 7 g of the product obtained above were reacted with 6.09 g of phosphorus tribromide in chloroform by the method described in Example 1E). The reaction mixture was worked up as described in Example 1E). 7.8 g of 6-(2-bromoethyl)-5-methyl-2,3-dihydropyrrolo[1,2,3-de]-1,4-benzothiazine having a melting point of 94° C. were obtained.

G) 3.5 g of the product obtained above were heated under reflux for 14 hours with 2.32 g of 1-(4-methylpyridin-2-yl)piperazine and 3.3 ml of tri-ethylamine in 100 ml of toluene, a further 1.5 ml of triethylamine being added after 10 hours. The reaction mixture was worked up by rendering it alkaline by adding 200 ml of aqueous sodium bicarbonate solution and extracting with dichloromethane. The dichloromethane extract was washed with water until neutral, dried and evaporated. 1.4 g of crude title compound were obtained as an oil. For conversion to the hydrochloride, the crude title base obtained was dissolved in 50 ml of acetone and the solution was treated with 6.3 ml of 2.2N isopropanolic hydrochloric acid solution. The precipitated hydrochloride of the title compound was filtered out and recrystallized from an isopropyl alcohol/ethanol mixture. 0.9 g of 5-methyl-6-{2-[4-(4-methylpyridin-2-yl)piperazin-1-yl]-ethyl}-2,3-dihydropyrrolo[1,2,3-de]-1,4-benzothiazine.2 HCl having a melting point of 240° C. was obtained.

EXAMPLE 12

2-[4-(4-Hydroxybutyloxy)-phenyl]-1-{2-[4-(4-methyl-pyridin-2-yl)piperazin-1-yl]ethyl}-5,6-dihydro-4H-pyrrolo[3,2,1-ij]quinoline A) Under a nitrogen atmosphere, 0.25 g of sodium hydride was added to 50 ml of dry dimethylformamide, and the solution was heated to a temperature of 80° C. A solution of 4 g of 2-(4-hydroxyphenyl)-1-{2-[4-(4-methylpyridin-2-yl)piperazin-1-yl]ethyl}-5,6-dihydro-4H-pyrrolo[3,2,1-ij]quinoline (preparation see Example 8) in 75 ml of dimethylformamide was then added. The reaction mixture was stirred for 10 minutes, whereupon it assumed a greenish coloration. A solution of 1.6 g of ethyl 4-bromobutyrate in 40 ml of dimethylformamide was then added, and the reaction mixture was heated at 80° C. for 30 minutes. The reaction mixture was worked up by adding water and then extracting with dichloromethane. The organic phase was separated, washed, dried and concentrated. The residue which remained was purified by chromatography on a silica gel column, toluene to which amounts of ethanol increasing to 2% had been added being used as the eluent. 1 g of oily ethyl 4-[4-[1-{2-[4-(4-methylpyridin-2-yl)piperazin-1-yl]ethyl}-5,6-dihydro-4H-pyrrolo[3,2,1-ij]quinoline-2-yl]-phenoxy]-butyrate was obtained.

B) 0.7 g of the ester obtained above was added dropwise to a solution of 0.1 g of lithium aluminum hydride in dry tetrahydrofuran using a pipette while cooling in an ice-bath, whereupon the reaction mixture immediately foamed up. To work up the reaction mixture, first a few drops of water, then a few drops of 10% strength sodium hydroxide solution and 15 ml of tetrahydrofuran were added to hydrolyze the product. The reaction mixture was then filtered through zeolite, and the filtrate was dried and concentrated. 0.6 g of crude product was obtained, which was purified by chromatography on a silica gel column using first toluene and then toluene/ethanol 99:1 as the eluent. 250 mg of 2-[4-(4-hydroxy-butoxy)-phenyl]-1-(2-[4-(4-methylpyridin-2-yl)-piperazin-1-yl]ethyl}-5,6-dihydro-4H-pyrrolo[3,2,1-ij]quinoline were obtained.

To convert the product to the corresponding dihydrochloride, the title base was dissolved in isopropanol. Isopropanolic hydrochloric acid and then ether were added to the solution. The resulting precipitate was filtered out. 250 mg of 2-[4-(4-hydroxybutoxy)phenyl]-1-{2-[4-(4-methylpyridin-2-yl)piperazin-1-yl)piperazin-1-yl)ethyl}-5,6-dihydro-4H-pyrrolo[3,2,1-ij]quinoline 2 HCl 2 H$_2$O having a melting point of 150° C. were obtained.

EXAMPLE 13

5,6-Dihydro-1-{2-[4-(4-methylpyridin-2-yl)piperazin-1-yl]ethyl}-4H-pyrrolo[3,2,1-ij]quinoline A) 17 g of 1-amino-1,2,3,4-tetrahydroquinoline (preparation see Example 1B) and 20 g of 2-ketoglutaric acid were heated under reflux at a temperature of 80° C. for 2 hours in a mixture of 160 ml of acetic acid and 11.4 ml of concentrated hydrochloric acid. To work up the reaction mixture the solid residue which remained was taken up in water and extracted with ethyl acetate. The organic phase was separated and extracted with 20% strength aqueous sodium hydroxide solution. The alkaline (pH=9) aqueous phase was separated and acidified to pH=4 by addition of aqueous 10% strength hydrochloric acid solution, and a precipitate formed. The solution was extracted with ethyl acetate. The organic phase was evaporated. 10.6 g of crude 5,6-dihydro-4H-pyrrolo-[3,2,1-ij]quinoline-1-acetic acid were obtained as a solid residue.

B) 2.7 g of the acid obtained above were dissolved in 150 ml of dichloromethane. 3.2 g of carbonyldiimidazole were added to the solution, and the reaction mixture was heated under reflux for 1 hour. 2.63 g of 1-(4-methylpyridin-2-yl)piperazine were then added, and the reaction mixture was heated under reflux for a further 3 hours. The reaction mixture was worked up by washing with 100 ml of 10% strength aqueous hydrochloric acid solution and twice with water, then with 50 ml of 10% strength aqueous sodium hydroxide solution and finally with water to neutrality. The organic phase was then concentrated. 3.7 g of crude 5,6-dihydro-1-{2-[4-(4-methylpyridin-2-yl)piperazin-1-yl]-2-oxoethyl}-4H-pyrrolo[3,2,1-ij]quinoline were obtained as an oily residue.

C) 0.8 g of lithium aluminum hydride was suspended in 30 ml of anhydrous tetrahydrofuran. A solution of 3.7 g of the amide compound obtained above in 50 ml of tetrahydrofuran was added to the suspension. The reaction mixture was heated under reflux for 1 hour. The reaction mixture was worked up by cooling and then hydrolyzing by adding 2 ml of a mixture of equal parts of water and tetrahydrofuran, then 1 ml of 15% strength aqueous sodium hydroxide solution and a further 1 ml of water. The resulting precipitate was then filtered out and was washed again with dichloromethane. The combined filtrates were concentrated and the residue which remained was dissolved in dichloromethane. The solution obtained was washed with water, dried and evaporated. 3 g of crude, oily 5,6-dihydro-1-{2-[4-(4-methylpyridin-2-yl)piperazin-1-yl]ethyl}-4H-pyrrolo[3,2,1-ij]-quinoline were obtained.

To convert it to the corresponding dihydrochloride, the title base obtained above was dissolved in isopropanol. Isopropanolic 2.3N hydrochloric acid was added to the solution, and the dihydrochloride of the title compound crystallized out. The 5,6-dihydro-1-{2-[4-(4-methylpyridin-2-yl)piperazin-1-yl]ethyl}-4H-pyrrolo[3,2,1-ij]quinoline dihydrochloride obtained had a melting point of 215° C. after recrystallization from ethanol.

EXAMPLE 14

2-Ethyl-5,6-dihydro-1-{2-[4-(4-methylpyridin-2-yl)piperazin-1-yl]-1-hydroxyethyl}-4H-pyrrolo[3,2,1-ij]quinoline A) 8.2 g of 1-amino-1,2,3,4-tetrahydroquinoline were dissolved in 20 ml of isopropanol. 5.6 g (5.7 ml) of butane-2,3-dione were added to the solution, and the reaction mixture was heated under reflux for 2 hours. 20 ml of 2.5 molar isopropanolic hydrochloric acid solution were then added, and the reaction mixture was heated under reflux for a further 5 hours. The reaction mixture was worked up by removing the isopropanol by evaporation and extracting the residue with dichloromethane. The dichloromethane phase was washed with water, dried and concentrated. 6 g of oily crude product were obtained, which was purified by chromatography on a small silica column using dichloromethane as the eluent. 2.4 g of solid 2-acetyl-5,6-dihydro-4H-pyrrolo-[3,2,1-ij]quinoline were obtained from the first eluate fraction.

B) 1 g of the product obtained above was heated under reflux at a temperature of 170° C. for 2 hours with 1.4 ml of hydrazine (98% strength) and 1 g of potassium hydroxide in 14 ml of diethylene glycol. Water and hydrazine were then removed by evaporation, the temperature rising to 190° C., and the reaction mixture was kept at this temperature for a further 2 hours. For working-up, the reaction mixture was cooled to 100° C., poured onto ice and extracted with ethyl acetate. The ethyl acetate extract was washed with water, dried and evaporated. 0.57 g of crude oily 2-ethyl-5,6-dihydro-4H-pyrrolo[3,2,1-ij]quinoline was obtained.

C) 1.63 g of oxalyl chloride were dissolved in 10 ml of diethyl ether A solution of 2 g of the product obtained above in 20 ml of diethyl ether was added to the solution at a temperature of 5° C. The reaction mixture was then heated under reflux for 3 hours After cooling to 5° C., a solution of 2.3 g of 1-(4-methylpyridin-2-yl)piperazine in 15 ml of tetrahydrofuran was added and the reaction mixture was heated under reflux for one hour. To work up the reaction mixture 100 ml of water were added and the mixture was extracted with dichloromethane. The dichloromethane extract was dried and concentrated. 3.3 g of oily crude product were obtained, which was purified by chromatography on a small silica gel column using dichloromethane/ethanol as the eluent. 3 g of 2-ethyl-5,6-dihydro-1-{2-[4-(4-methyl-yl-pyridin-2-yl)piperazin-1-yl]-1,2-dioxoethyl}-4H-pyrrolo-[3,2,1-ij]quinoline were obtained.

D) 0.3 g of lithium aluminum hydride were suspended in 20 ml of tetrahydrofuran. A solution of 1 g of the product obtained above in 20 ml of tetrahydrofuran was added to the suspension. The reaction mixture was then heated under reflux for 4 hours. To work up the reaction mixture it was hydrolyzed by successively adding 1 ml of a tetrahydrofuran/water mixture, 0.5 ml of a 15% strength aqueous sodium hydroxide solution and 0.5 ml of water. The mixture was then filtered, the filtrate was concentrated, and the residue was extracted with dichloromethane. The dichloromethane extract was washed with water, dried and concentrated. 800 mg of 2-ethyl-5,6-dihydro-1-{2-[4-(4-methylpyridin-2-yl)piperazin-1-yl]- 2-hydroxyethyl}-4H-pyrrolo[3,2,1-ij]quinoline having a melting point of 60° C. were obtained.

EXAMPLE 15

2-Ethyl-5,6-dihydro-1-{2-[4-(4-methylpyridin-2-yl)piperazin-1-yl]ethyl}-4H-pyrrolo[3,2,1-ij]quinoline 0.32 g of lithium aluminum hydride was suspended in 20 ml of tetrahydrofuran. A solution of 0.7 g of 2-ethyl-5,6-dihydro-1-(2-[4-(4-methylpyridin-2-yl)piperazin-1-yl]-1,2-dioxoethyl}-4H-pyrrolo-[3,2,1-ij]quinoline (preparation see Example 14C) in 20 ml of tetrahydrofuran was added to the suspension. The reaction mixture was heated under reflux for 9 hours and then worked up as described in Example 14D). 600 mg of oily crude product were obtained. This was purified by chromatography on a silica gel column using toluene/ethanol 95:5 as the eluent. 300 mg of 2-ethyl-5,6-dihydro-1-{2-[4-(4-methylpyridin-2-yl)piperazin-1-yl]ethyl}-4H-pyrrolo[3,2,1-ij]quinoline were obtained as an oil.

EXAMPLE 16

5,6-Dihydro-2-hydroxyethyl-1-{2-[4-(4-methylpyridin-2-yl)piperazin-1-yl]ethyl}-4H-pyrrolo[3,2,1-ij]quinoline A) 30 g of 2-ketoglutaric acid were boiled under reflux for 3 hours in 500 ml of ethanol with the addition of 3 ml of sulfuric acid. The ethanol was then removed by evaporation, the residue was extracted with dichloromethane, and the dichloromethane phase was washed with water, dried and concentrated. 37 g of oily diethyl 2-ketoglutarate were obtained.

B) 5.5 g of 1-amino-1,2,3,4-tetrahydroquinoline and 8.7 g of diethyl 2-ketoglutarate were heated under reflux for 1 hour in a mixture of 100 ml of acetic acid and 2 ml of 12N hydrochloric acid. The reaction mixture was worked up by removing the acetic acid by evaporation, then adding 10% strength aqueous sodium hydroxide solution until a pH of 10 was attained, adding the mixture to 100 ml of water and extracting with dichloromethane. The organic phase was washed with water, dried over sodium sulfate and concentrated. 12 g of oily crude product were obtained. This was purified by means of column chromatography on silica gel under slightly elevated pressure (flash chromatography) using toluene/ethanol 95:5 as the eluent. 9.7 g of ethyl 2-ethoxycarbonyl-5,6-dihydro-4H-pyrrolo[3,2,1-ij]quinoline-1-acetate were obtained.

C) To hydrolyze the acetic acid ethyl ester group, 9.5 g of the product obtained above were dissolved in 50 m of ethanol. 28 ml of an ethanol solution of potassium hydroxide (containing 3 g of potassium hydroxide in 50 ml of ethanol) were added to the solution, and the reaction mixture was heated at 60° C. for 2 hours. The reaction mixture was worked up by removing the ethanol by evaporation, dissolving the remaining residue in water and washing the mixture three times with diethyl ether. The aqueous phase was then acidified to pH 3 with hydrochloric acid and extracted with ethyl acetate. The ethyl acetate phase was separated, washed three times with water, dried and concentrated. 3 g of oily residue were obtained which were purified by chromatography on silica gel using dichloromethane/ethanol 9:1 as the eluent. 1.7 g of 2-ethoxycarbonyl-5,6-dihydro-4H-pyrrolo-[3,2,1-ij]quinoline-1-acetic acid were obtained as an oil which subsequently crystallized.

D) 1.7 g of the acid obtained above were reacted with 1.3 g of 1-(4-methylpyridin-2-yl)piperazine in dichloromethane in the presence of 1.54 g of carbonyldiimidazole as described in Example 13B). The reaction mixture was worked up as described in Example 13B). 1.3 g of oily 2-ethoxycarbonyl-5,6-dihydro-1-{2-[ 4-(4-methylpyridin-2-yl)piperazin-1-yl]-2-oxoethyl}-4H-pyrrolo[3,2,1-ij]quinoline were obtained.

E) 0 2 g of lithium aluminum hydride was suspended in 50 ml of tetrahydrofuran. A solution of 1.3 g of the product obtained above in 25 ml of tetrahydrofuran was added to the suspension. The reaction mixture was allowed to react at room temperature for 1 hour. It was then worked up as described in Example 13C) and the crude product obtained was purified by chromatography on silica gel. 0.8 g of 5,6-dihydro-2-hydroxymethyl-1-{2-[4-(4-methylpyridin-2-yl)piperazin-1-yl]ethyl}-4H-pyrrolo[3,2,1-ij]quinoline was obtained.

The title base obtained was dissolved in ethanol and a solution of 0.5 g of fumaric acid in ethanol was added to the solution. After concentrating the solution, 800 mg of 5,6-dihydro-2-hydroxymethyl-1-{2-[4-(4-methylpyridin-2-yl)piperazin-1-yl]ethyl}-4H-pyrrolo[3,2,1-ij]quinoline difumarate 1.5 H₂O having a melting point of 100° C.(decomposition) were obtained.

EXAMPLE 17

5,6-Dihydro-2-methyl-1-{3-[4-(4-methylpyridin-2-yl)piperazin-1-yl]propyl-4H-pyrrolo[3,2,1-ij]quinoline A) A solution of 2.96 g of sodium cyanide in 60 ml of water was added to a solution of 14 g of 1-(2-bromoethyl)-5,6-dihydro-2-methyl-4H-pyrrolo[3,2,1-ij]quinoline in 100 ml of toluene, and the reaction mixture was heated under reflux for 4 hours. To work up the reaction mixture it was concentrated to dryness, and the residue was washed with water and extracted with dichloromethane. The dichloromethane phase was separated, dried and evaporated. 10.5 g of crude 1-(3-cyanopropyl)-5,6-dihydro-2-methyl-4H-pyrrolo[3,2,1-ij]-quinoline were obtained as a brownish oil.

B) 10.5 g of the product obtained above were dissolved in 50 ml of acetic acid. 50 ml of water and 50 ml of sulfuric acid were then added, and the reaction mixture was heated under reflux for 45 minutes. To work up the reaction mixture, water and concentrated sodium hydroxide solution were added while cooling in an ice-bath. The reaction mixture was then extracted with dichloromethane, and the dichloromethane phase was separated, dried and concentrated. The residue was taken up in 200 ml of 10% strength sodium hydroxide solution and extracted again with dichloromethane. The aqueous phase was separated, acidified to pH 4-5 with dilute hydrochloric acid and extracted again with dichloromethane. The combined dichloromethane phases were washed, dried and concentrated, and the crude product which remained as a residue was purified by column chromatography on silica gel using toluene/ethanol 95:5 as the eluent. 3g of 3-(5,6-dihydro-2-methyl-4H-pyrrolo[3,2,1-ij]quinolin-1-yl)propionic acid were obtained as an oil which crystallized.

C) 2.8 g of the acid obtained above were heated under a nitrogen atmosphere for 2 hours at 40° C. with 2.98 g of carbonyldiimidazole in 50 ml of dimethylformamide. 2.45 g of 1-(4-methylpyridin-2-yl)piperazine were then added and the reaction mixture was heated at 40° C. for a further 7 hours. The reaction mixture was worked up by removing the dimethylformamide by evaporation and taking up the residue in 100 ml of dichloromethane. The dichloromethane solution was washed successively with 50 ml of 10% strength aqueous hydrochloric acid solution, 50 ml of water and 50 ml of 10% strength aqueous sodium hydroxide solution and then washed with water until neutral, dried and concentrated. 4.3 g of an orange-colored oil were obtained as a residue. This was dissolved hot in a little toluene and hexane was added dropwise to the solution until a precipitate deposited. The precipitate was filtered out and dried. 2.2 g of 5,6-dihydro-2-methyl-1-{3-[4-(4-methylpyridin-2-yl)piperazin-1-yl]-3-oxopropyl}-4H-pyrrolo[3,2,1-ij]quinoline were obtained as a dark pink powder.

D) 1.5 g of the product obtained above were reduced by the method described in Example 13C) using 0.83 g of lithium aluminum hydride in tetrahydrofuran. The reaction mixture was worked up as described in Example 13C). 1.35 g of crude 5,6-dihydro-2-methyl-1-{3-[4-(4-methylpyridin-2-yl)piperazin-1-yl]-propyl}-4H-pyrrolo[3,2,1-ij]quinoline were obtained as a yellow oil. For further purification, this crude title compound was taken up again in dichloromethane, and the dichloromethane solution was washed with aqueous sodium bicarbonate solution and then with water, dried and concentrated. 0.7 g of purified title compound was obtained.

The title base was converted to the corresponding hydrochloride as described in Example 3H) and crystallized as 5,6-dihydro-2-methyl-1-{3-[4-(4-methylpyridin-2-yl)-piperazin-1-yl]propyl}-4H-pyrrolo[3,2,1-ij]quinoline dihydrochloride 2.5 H$_2$O having a melting point of 175° C.

EXAMPLE 18

5,6-Dihydro-4-hydroxymethyl-2-methyl-1-{2-[4-(4-methylpyridin-2-yl)piperazin-1-yl]ethyl}-4H-pyrrolo[3,2,1-ij]-quinoline A) 29.89 g of quinoline-2-carboxylic acid were heated under reflux for 5½ hours in 450 ml of ethanol with the addition of 3.5 ml of sulfuric acid. The reaction mixture was worked up by evaporating it, taking up the residue in water and extracting the mixture with dichloromethane. The organic phase was washed with aqueous sodium bicarbonate solution and then with water until neutral, dried and evaporated. 32.23 g of crude ethyl quinoline-2-carboxylate were obtained as a green oil.

B) 32 g of the product obtained above were reduced as described in Example 4B) using 20 g of sodium cyanoborohydride in acetic acid. The reaction mixture was worked up as described in Example 4B). 22.56 g of crude ethyl 1,2,3,4-tetrahydro-quinoline-2-carboxylate were obtained as a yellow-orange oil.

C) 21 g of the product obtained above were added to a mixture of 17 ml of 12 N hydrochloric acid and 50 g of ice and reacted with a solution of 8.47 g of sodium nitrite in 20 ml of water analogously to Example ;A). The reaction mixture was worked up as described in Example 1A). 21.31 g of ethyl 1-nitroso-1,2,3,4-tetrahydroquinoline-2-carboxylate were obtained as a brownish oil.

D) 21 g of the product obtained above were reduced in tetrahydrofuran as described in Example 1B) using 10.21 g of lithium aluminum hydride. The reaction mixture was worked up as described in Example 1B). 12.76 g of 2-(1-amino-1,2,3,4-tetrahydroquinolin-2-yl)ethanol were obtained as a brownish-orange oil.

E) 22 g of the product prepared above were heated under reflux at 80° C. for 2 hours with 21.3 g of ethyl levulinate in a mixture of 183 ml of acetic acid and 11 ml of 12 N hydrochloric acid. To work up the reaction mixture it was evaporated, the residue was taken up in water and the mixture was extracted with dichloromethane. The organic phase was separated, washed with 10% strength aqueous sodium hydroxide solution and then washed with water until neutral, dried and concentrated. As a residue, 34.42 g of a brownish oil remained. This was purified by chromatography on a small silica gel column using pure toluene as the eluent. 28.51 g of crude ethyl 5,6-dihydro-4-hydroxymethyl-2-methyl-4H-pyrrolo[3,2,1-ij]quinoline-1-acetate were obtained.

F) 7.5 g of the product obtained above were heated under reflux for 4 hours with 3 g of sodium hydroxide in a mixture of 50 ml of water and 10 ml of ethyl alcohol. The reaction mixture was worked up by adding 30 ml of 20% strength aqueous hydrochloric acid and extracting twice with dichloromethane. The combined dichloromethane phases were washed with water, dried and concentrated. 4.5 g of crude 5,6-dihydro-4-hydroxymethyl-2-methyl-4H-pyrrolo[3,2,1-ij]quinoline-1-acetic acid were obtained.

G) 0.5 g of the acid obtained above was reacted with 0.4 g of 1-(4-methylpyridin-2-yl)piperazine in dichloromethane in the presence of 0.38 g of carbonyldiimidazole as described in Example 13B). The reaction mixture was worked up as described in Example 13B). 200 mg of oily 5,6-dihydro-4-hydroxymethyl-2-methyl-1-{2-[4-(4-methylpyridin-2-yl)-piperazin-1-yl]-2-oxoethyl}-4H-pyrrolo[3,2,1ij]quinoline were obtained.

H) 0.36 g of lithium aluminum hydride was suspended in 20 ml of anhydrous tetrahydrofuran. A solution of 2 g of the product prepared above in 20 ml of tetrahydrofuran was added dropwise to the suspension. The reaction mixture was then stirred at room temperature for 1 hour. The reaction mixture was worked up as described in Example 13 B). 1.8 g of crude, oily 5,6-dihydro-4-hydroxymethyl-2-methyl-1-{2-[4-(4-methylpyridin-2-yl)piperazin-1-yl]ethyl}-4H-pyrrolo[3,2,1-ij]quinoline were obtained.

For conversion to the corresponding fumarate, 1 g of the title base obtained above was dissolved in a little ethanol, and the solution was treated with a solution of 0.6 g of fumaric acid in ethanol. The reaction mixture was evaporated to dryness, the residue was taken up in dimethyl ether, and the resulting precipitate was filtered out and dried. 0.5 g of 5.6-dihydro-4-hydroxymethyl-2-methyl-1-{2-[4-(4-methylpyridin-2-yl)piperazine-1-yl]ethyl}-4H-pyrrolo[3,2,1-ij]quinoline-1,5-fumarate having a melting point of 110° C. was obtained.

EXAMPLE 19

5,6-Dihydro-8-(1-hydroxy-2-methylpropyl)-2-methyl-1-{2-[4-(4-methylpyridin-2-yl)piperazin-1-yl]ethyl}-4H-pyrrolo-[3,2,1-ij]quinoline A) 63 g of aluminum trichloride were suspended in 150 ml of chloroform at a temperature of 10° C. A mixture of ethyl 5,6-dihydro-2-methyl-4H-pyrrolo[3,2,1-ij]quinoline-1-acetate and 26.3 g of isobutyryl chloride in 150 ml of chloroform was added to the suspension while the temperature was maintained at 10° C. The reaction mixture was stirred at room temperature for hour, then heated under reflux for 4 hours and kept at room temperature for a further 12 hours. A further 10 g of aluminum chloride were then added, and the mixture was heated under reflux for a further hour. The reaction mixture was worked up by pouring it onto ice and then extracting with dichloromethane. The organic phase was washed with dilute aqueous sodium hydroxide solution, then washed with water until neutral, dried and concentrated. 80 g of crude product were obtained, which was purified by chromatography on a silica gel column using dichloromethane as the eluent. 42.5 g of ethyl 5,6-dihydro-8-(2-methyl-1-oxopropyl)-2-methyl-4H-pyrrolo[3,2,1-ij]quinoline-1-acetate were obtained.

B) 37.5 g of the ester obtained above were heated under reflux for 1 hour with 13.7 g of sodium hydroxide in a mixture of 300 ml of ethanol and 60 ml of water. The reaction mixture was worked up by removing the alcohol by evaporation, taking up the resulting precipitate in water and washing the aqueous phase three times with dichloromethane. The aqueous phase was then acidified to a pH of 2 by addition of dilute hydrochloric acid. The resulting precipitate was dissolved in dichloromethane, and the dichloromethane phase was washed, dried and concentrated. 40 g of solid crude product were obtained, which was crystallized from toluene. 22 g of 5,6-dihydro-8-(2-methyl-1-oxopropyl)-2-methyl-4H-pyrrolo[3,2,1-ij]quinoline-1-acetic acid having a melting point of 162° C. were obtained.

C) 22 g of the acid obtained above were reacted with 14.4 g of 1-(4-methylpyridin-2-yl)piperazine in dichloromethane in the presence of 17 g of carbonyldiimidazole as described in Example 13B). The reaction was worked up as described in Example 13B). 34 g of oily 5,6-dihydro-8-(2-methyl-1-oxopropyl)-2-methyl-1-{2-[4-(4-methylpyridin-2-yl)piperazin-1-yl]-2-oxoethyl}-4H-pyrrolo[3,2,1-ij]quinoline were obtained, which was crystallized from cyclohexane and had a melting point of 120° C.

7 g of lithium aluminum hydride were suspended in 200 ml of tetrahydrofuran. A solution of 34 g of the product obtained above in 100 ml of tetrahydrofuran were added to the suspension at a temperature of 15°-20° C. The reaction mixture was stirred at room temperature for 1 hour and then heated under reflux for hour. It was then worked up as described in Example 13C). 30.5 g of oily crude product were obtained, which was recrystallized from diisopropyl ether. 22 g of 5,6-dihydro-8-(2-methyl-1-hydroxypropyl)-2-methyl-1-{2-[4-(4-methylpyridin-2-yl)piperazin-1-yl]ethyl}-4H-pyrrolo-[3,2,1-ij]quinoline having a melting point of 140° C. were obtained.

0.6 g of the title base obtained above was converted as described in Example 18H) to the corresponding 1,2-fumarate having a melting point of 130° C.

EXAMPLE 20

8-Amino-5,6-dihydro-2-methyl-1-{2-[4-(4-methylpyridin-2-yl)piperazin-1-yl]ethyl}-4H-pyrrolo[3,2,1-ij]quinoline A) 20 g of 5,6-dihydro-2-methyl-4H-pyrrolo[3,2,1-ij]quinoline-1-acetic acid (prepared by hydrolysis of its ethyl ester obtained by Example 1C)) were cautiously added to 50 ml of sulfuric acid cooled to 0° C. The nitrating acid (=mixture of 5.56 ml of concentrated sulfuric acid and 4.04 ml of concentrated nitric acid) was then added cautiously. The reaction mixture was allowed to react at a temperature of 0° C. for 1 hour and at room temperature for 2 hours. To work up the reaction mixture, it was added to 200 g of ice, and a precipitate formed. The reaction mixture was extracted with dichloromethane, and a part of the precipitate which formed dissolved in the dichloromethane phase. The dichloromethane phase was separated, and the residual precipitate which remained in the aqueous phase was filtered out, washed with water and dried. 7.54 g of 5,6-dihydro-2-methyl-8-nitro-4H-pyrrolo-[3,2,1-ij]quinoline-1-acetic acid were obtained as a greenish-yellow powder. The dichloromethane phase was washed with water, dried and concentrated. The residue which remained, which further contained acid in addition to oily impurities, was treated with about 25 ml of ethanol to remove the oily impurities and filtered. A further 3.23 g of the acid were thus obtained, so that the total yield was 10.8 g.

B) 27.4 g of the acid prepared above were dissolved in 500 ml of dimethylformamide. 25 g of carbonyldiimidazole were added to the solution, and the reaction mixture was warmed to 50° C. for 2 hours. 21.3 g of 1-(4-methylpyridin-2-yl)piperazine were then added and the reaction mixture was heated at 50° C. for a further 4 hours. The reaction mixture was worked up by evaporating the dimethylformamide, dissolving the residue in 400 ml of dichloromethane, washing the solution first with 250 ml of 10% strength aqueous hydrochloric acid solution, then with 250 ml of water and then with 250 ml of 10% strength aqueous sodium hydroxide solution. After a final washing with water until neutral, the solution was dried and concentrated. The crude product which remained as a residue was crystallized from ethanol. 28 g of 5,6-dihydro-2-methyl-8-nitro-1-{2-[4-(4-methylpyridin-1-yl]-2-oxoethyl)-4H-pyrrolo[3,2,1-ij]quinoline were obtained as an ochre-colored powder.

C) 3 g of the product obtained above were added to a mixture of 200 ml of ethanol and 100 ml of methanol. 0.5 g of a palladium/carbon catalyst (10% palladium on carbon) was then added, and the reaction mixture was hydrogenated for 7 hours at a temperature of 50° C. using a hydrogen pressure of 3–4 bar. The catalyst was then filtered out, and the filtrate was evaporated to dryness. 3.3 g of crude 8-amino-5,6-dihydro-2-methyl-1-{2-[4-(4-methylpyridin-2-yl)piperazin-1-yl]-2-oxoethyl}-4H-pyrrolo[3,2,1-ij]quinoline were obtained as a dark brown powder.

Instead of using catalytic hydrogenation, the nitro compound can also be reduced by reaction with sodium borohydride in the presence of a palladium/carbon catalyst in tetrahydrofuran.

D) 0.47 g of lithium aluminum hydride were added to 80 ml of tetrahydrofuran cooled to a temperature of 0°–5° C. The reaction mixture was allowed to warm to room temperature. A solution of 2.5 q of the product obtained above in tetrahydrofuran was then added. The reaction mixture was allowed to react at room temperature for 1 hour. It was then worked up as described in Example 13C) and the crude product obtained was purified by chromatography on a silica gel column using toluene/ethanol 9:1 as the eluent. 0.8 g of 8-amino-5,6-dihydro-2-methyl-1-{2-[4-(4-methylpyridin-2-yl)piperazin-1-yl]ethyl}-4H-pyrrolo[3,2,1-ij]quinoline was obtained as a brownish red oil.

The title base obtained above was dissolved in isopropanol and the solution was treated with 3.5 molar isopropanolic hydrochloric acid solution. 0.8 g of 8-amino-5,6-dihydro-2-methyl-1-{2-[4-(4-methylpyridin-2-yl)piperazin-1-yl]ethyl}-4H-pyrrolo-[3,2,1-ij]quinoline 2.8 HCl 2 H$_2$O was obtained as a grey powder having a melting point of 250° C.(decomp.).

EXAMPLE 21

5,6-Dihydro-2-methyl-8-(2-methylpropyl)-1-{2-[4-(4-methylpyridin-2-yl)piperazin-1-yl]ethyl}-4H-pyrrolo[3,2,1-ij]quinoline A) 3.2 g of ethyl 5,6-dihydro-8-(2-methyl-1-oxypropyl)-2-methyl-4H-pyrrolo[3,2,1-ij]quinoline-1-acetate (preparation see Example 19A) were dissolved in 40 ml of diethylene qlycol. 2.6 g of potassium hydroxide were added to the solution, and the reaction mixture was heated at 80° C. for 1 hour to dissolve the potassium hydroxide. 3.2 ml of hydrazine (98% strength) were then added, and the reaction mixture was heated at a temperature of 140°–150° C. for 2 hours. Water and hydrazine were then removed by evaporation, the temperature rising to 210° C., and the reaction mixture was kept at this temperature for 3 more hours. The reaction mixture was worked up as described in Example 14B). 3 g of solid 5,6-dihydro-2-methyl-8-(2-methylpropyl)-4H-pyrrolo-[3,2,1-ij]quinoline-1-acetic acid were obtained.

B) 2.9 g of the acid obtained above were reacted in dichloro-methane with 1.98 g of 1-(4-methylpyridin-2-yl)piperazine in the presence of 2.4 g of carbonyldiimidazole as described in Example 13B). The reaction mixture was worked up as described in Example 13B). 3.2 g of 5,6-dihydro-2-methyl-8-(2-methylpropyl)-1-{2-[4-(4-methylpyridin-2-yl)piperazin-1-yl]-2-oxoethyl}-4H-pyrrolo[3,2,1-ij]quinoline were obtained.

C) 0.6 g of lithium aluminum hydride were suspended in 20 ml of tetrahydrofuran at a temperature of 0°–5° C. A solution of 3.2 g of the product obtained above in 10 ml of tetrahydrofuran was added to the suspension. The reaction mixture was stirred at room temperature for 1 hour and then heated under reflux for 2 hours. It was then worked up as described in Example 13C). 2.7 g of oily 5,6-dihydro-2-methyl-8-(2-methylpropyl)-1-{2-[4-(4-methylpyridin-2-yl)piperazin-1-yl]ethyl}-4H-pyrrolo[3,2,1-ij]quinoline were obtained.

The title base was converted to its dihydrochloride as described in Example 1H). This was recrystallized from isopropanol/ethanol. 1 g of the dihydrochloride of the title compound having a melting point of 228° C. was obtained.

EXAMPLE 22

5,6-Dihydro-2-methyl-1-{2-[4-(4-methylpyridin-2-yl)piperazin-1-yl]ethyl}-4H-pyrrolo[3,2,1-ij]quinoline A) 20 g of 1-(2-bromoethyl)-5,6-dihydro-2-methyl-4H-pyrrolo[3,2,1-ij]quinoline, 10.15 g of 1-acetylpiperazine, 1,2 g of potassium iodide and 20.2 ml of triethylamine were heated at a temperature of 80°–85° C. for 5 hours in 300 ml of dimethylformamide. To work up the reaction mixture it was concentrated, and the residue was taken up in dichloromethane. The dichloromethane phase was first washed with 10% strength aqueous sodium hydroxide solution, then with water until neutral, and then dried and concentrated. 22.3 g of brown oily crude product were obtained. This was purified by chromatography on a small silica gel column using dichloromethane/ethanol 95:5 as the eluent and crystalized from diisopropyl ether. 8.3 g of 5,6-dihydro- 2-methyl-1-[2-(4-acetylpiperazin-1-yl)ethyl]-4H-pyrrolo[3,2,1-ij]quinoline were obtained.

B) 8 g of the product obtained above were heated under reflux for 45 minutes in 20.5 ml of aqueous 6 N hydrochloric acid. To work up the reaction mixture it was cooled and neutralized by adding aqueous 10% strength sodium hydroxide solution. It was then extracted with dichloromethane, and the dichloromethane phase was separated, washed with water until neutral, dried and evaporated. 8.85 g of crude product were obtained as a brown oil. This was treated with diethyl ether. In this way, 2 g of pure and 4.5 g of oily, only slightly impure5,6-dihydro-2-methyl-1-[2-(piperazin-1-yl-ethyl]-4H-pyrrolo-[3,2,1-ij]quinoline were obtained. 115.5 g of 2-amino-4-methylpyridine were added over the course of 20 minutes to 553 ml of 48% strength aqueous hydrobromic acid solution cooled to 10°–15° C. The reaction mixture was cooled to a temperature of 0°–5° C. and 161 ml of bromine were then added over the course of 1½ hours. An orange-colored precipitate formed. A further 100 ml of 48% strength aqueous hydrobromic acid were added to the reaction mixture, and a solution of 189 g of sodium nitrite in 280 ml of Water Were then added over the course of 3 hours while maintaining a temperature of 0° C. In this way, the precipitate which had formed was completely dissolved. The reaction mixture was allowed to stand at room temperature for a further 12 hours. 500 g of sodium hydroxide in 700 ml of water were then added over the course of 3 hours without exceeding a temperature of 20° C. To work up the reaction mixture, it was extracted once with 400 ml and three times with 200 ml portions of diethyl ether. The combined ether phases were washed, dried and concentrated. 171.7 g of crude, oily 2-bromo-4-methylpyridine were obtained. For purification, the crude 2-bromo-4-methylpyridine was converted to its hydrochloride using isopropanolic 2.5N hydrochloric acid solution. This hydrochloride was filtered out and suspended in 600 ml of methanol. Ammonia was passed through the suspension. The reaction mixture was then filtered and concentrated, the residue was taken up in dichloromethane, and the dichloromethane phase was filtered and concentrated again. 153.4 g of 2-bromo-4-methylpyridine were obtained as a brownish oil.

D) g of 5,6-dihydro-2-methyl-1-[2-(piperazin-1-yl)-ethyl]-4H-pyrrolo[3,2,1-ij]quinoline, 1.45 g of 2-bromo-4-methylpyridine, 0.175 g of potassium iodide and 3 ml of triethylamine were heated at a temperature of 85° C. for 7 hours in 50 ml of dimethylformamide. The reaction mixture was worked up as described in Example 1H), and the crude title base obtained was converted into 5,6-dihydro-2-methyl-1-(2-[4-(4-methylpyridin-2-yl)piperazin-1-yl]ethyl}-4H-pyrrolo[3,2,1-ij]quinoline trihydrochloride having a melting point of 254° C.

EXAMPLE 23

4-n-Butyl-5,6-dihydro-8-(2-methyl-1-oxopropyl)-2-methyl-1-{2-[4-(4-methylpyridin-2-yl)piperazin-1-yl]ethyl}-4H-pyrrolo[3,2,1-ij]quinoline 0.76 g of aluminum chloride was suspended in 20 ml of chloroform. A solution of 1 g of 4-n-butyl-5,6-dihydro-2-methyl-1-{2-[4-(4-methylpyridin-2-yl)piperazin-1-yl]ethyl}-4H-pyrrolo[3,2,1-ij]quinoline (see Example No. 73) and 0.29 g isobuteryl chloride in 10 ml of chloroform was added to the suspension at a temperature of 5° C. The reaction mixture was stirred at room temperature for 1 hour. The reaction mixture was then worked up as described in Example 19A). The crude title compound was purified by chromatography on a silica gel column using dichloromethane/ethanol as the eluent. 0.65 g of the title compound was obtained.

The title base was dissolved in isopropanol for conversion to its hydrochloride, and the solution was treated with isopropanolic hydrochloric acid. The reaction mixture was concentrated, the residue was suspended in ether, and the mixture was filtered. 400 mg of 4-n-butyl-5,6-dihydro-8-(2-methyl-1-oxopropyl)-2-methyl-1-{2-[4-(4-methylpyridin-2-yl)piperazin-1-yl]ethyl}-4H-pyrrolo[3,2,1-ij]quinoline 1.9 HCl 1.2 H₂O having a melting point of 150° C. were obtained.

EXAMPLE 24

8-Acetoxy-5,6-dihydro-2-methyl-1-{2-[4-(4-methyl-pyridin-2-yl)piperazin-1-yl]ethyl}-4H-pyrrolo[3,2,1-ij]quinoline 2.2 g of 5,6-dihydro-2-methyl-8-hydroxy-1-{2-[4-(4-methylpyridin-2-yl)piperazin-1-yl]ethyl}-4H-pyrrolo[3,2,1-ij]quinoline (preparation see Example 6), 0.884 g of acetyl chloride and 0.78 ml of triethylamine were heated under reflux for 5 hours in 15 ml of toluene. To work up the reaction mixture it was added to 50 ml of 10% strength aqueous sodium hydroxide solution. The toluene phase was separated and washed with water until neutral and concentrated. 2 g of crude product were obtained, which was purified by chromatography on a small silica gel column using first dichloromethane and then dichloromethane/ethanol 98:2. 1.8 g of oily title compound were obtained. This was converted into its hydrochloride as described in Example 1H). 1.72 g of 8-acetoxy-5,6-dihydro-2-methyl-1-{2-[4-(4-methylpyridin-2-yl)piperazin-1-yl]ethyl}-4H-pyrrolo-[3,2,1-ij]quinoline 2 HCl 22.5 H₂O having a melting point of 220° C. were obtained.

EXAMPLE 25

8-Benzoylamino-5,6-dihydro-2-methyl-1-{2-[4-(4-methylpyridin-2-yl)piperazin-1-yl]-ethyl}-4H-pyrrolo[3,2,1-ij]quinoline 2 g of 8-amino-5,6-dihydro-2-methyl-1-{2-[4-(4-methylpyridin-2-yl)piperazin-1-yl]-ethyl}-4H-pyrrolo-[3,2,1-ij]quinoline (preparation see Example 20) were dissolved in 25 ml of chloroform. 1.45 ml of triethylamine and then, dropwise, 1.075 g of benzoyl chloride were added to the solution without exceeding a temperature of 20° C. in this process. The reaction mixture was allowed to react at room temperature for hour. To work up the reaction mixture, it was washed with 20 ml of 10% aqueous sodium hydroxide solution until neutral, dried and evaporated. The crude product obtained was purified by chromatography on a small silica gel column using toluene/ethanol 95:5 as the eluent. After recrystallization from ethanol, 0.6 g of 8-benzoylamino-5,6-dihydro-2-methyl-1-{2-[4-(4-methylpyridin-2-yl)-piperazin-1-yl]-ethyl}-4H-pyrrolo[3,2,1-ij]quinoline was obtained as a cream-colored powder. This was converted into the corresponding 0.5-hydrochloride having a melting point of 218° C. as described in Example 3H).

EXAMPLE 26

5,6-Dihydro-2-methyl-8-(2-methylprop-1-enyl)-1-{2-[4-(4-methylpyridin-2-yl)piperazin-1-yl]ethyl}-4H-pyrrolo[3,2,1-ij]quinoline 1 g of 5,6-dihydro-8-(2-methyl-1-hydroxypropyl)-2-methyl-1-{2-[4-(4-methylpyridin-2-yl)piperazin-1-yl]-ethyl}-4H-pyrrolo[3,2,1-ij]quinoline (preparation see Example 19) was dissolved in 40 ml of toluene. 0.042 g of p-toluenesulfonic acid was added to the solution. The reaction mixture was heated under reflux for 6 hours in an apparatus equipped with a water separator. To work up the reaction mixture it was washed with 50 ml of 10% strength aqueous sodium hydroxide solution. The organic phase was then separated, washed with water until neutral, dried and evaporated. 0.9 g of oily title base was obtained. This was converted into the corresponding hydrochloride as described in Example 1H). 790 mg of 5,6-dihydro-2-methyl-8-(2-methylprop-1-enyl)-1-{2-[4-(4-methylpyridin-2-yl)-piperazin-1-yl]-ethyl}-4H-pyrrolo-[3,2,1-ij]quinoline.1.9 HCl having a melting point of 190° C. were obtained.

EXAMPLE 27

5,6-Dihydro-2-methyl-8-(2-methyl-1-oxopropyl)-1-{2-[4-(4-methylpyridin-2-yl)piperazin-1-yl)ethyl}-4H-pyrrolo[3,2,1-ij]quinoline 1.9 HCl having a melting point of 190° C. were obtained.

EXAMPLE 27

5,6-Dihydro-2-methyl-8-(2-methyl-1-oxoproyl)-1-{2-[4-(4-methylpyridin-2-yl)piperazin-1-yl)ethyl}-4H-pyrrolo[3,2,1-ij]quinoline 3 g of pyridinium chlorochromate were dissolved under a nitrogen atmosphere in 20 ml of dichloromethane dried over calcium chloride. The solution was cooled to about 10° C., and 0.5 g of sodium acetate was then added. A solution of 2.5 g of 5,6-dihydro-2-methyl-8-(2-methyl-1-hydroxypropyl)-1-{2-[4-(4-methylpyridin-2-yl)piperazin-1-yl]ethyl}-4H-pyrrolo[3,2,1-ij]quinoline (preparation see Example 19) in 20 ml of dichloromethane dried over calcium chloride was then added. The reaction mixture was stirred for 3 hours, then a further 0.3 g of pyridinium chlorochromate was added and the mixture was stirred for a further 3 hours. To work up the reaction mixture 100 ml of dichloromethane were added and the mixture was filtered. 100 ml of water were added to the filtrate, and a precipitate formed. This was filtered out, and the organic phase was separated, washed with water, dried and concentrated. The oily crude product obtained was purified by chromatography on a silica gel column using toluene/ethanol 95:5 as the eluent. 1.4 g of oily title compound were obtained. This were converted into the corresponding hydrochloride as described in Example 1H), which was crystallized from isopropanol/ethanol. 940 mg of 5,6-dihydro-2-methyl-8-(2-methyl-1-oxopropyl)-1-{2-[4-(4-methylpyridin-2-yl)piperazin-1-yl]ethyl}-4H-pyrrolo-[3,2,1-ij]quinoline dihydrochloride having a melting point of 248° C. were obtained.

EXAMPLE 28

2,3-Dihydro-5-methyl-6-{2-[4-(4-methylpyridin-2-yl)-piperazin-1-yl]ethyl}-pyrrolo[1,2,3-de]-1,4-benzothiazine-1-oxide (=28a) and
2,3-dihydro-5-methyl-6-{2-[4-(4-methylpyridin-2-yl)-piperazin-1yl]ethyl}-pyrrolo[1,2,3-de]-1,4-benzothiazine-1,1-dioxide (=28b)

A solution of 0.84 g of 2,3-dihydro-5-methyl-6{2-[4-(4-methylpyridin-2-yl)piperazin-2-yl]ethyl}-pyrrolo[1,2,3-de]-1,4-benzothiazine (obtained from 1 g of the corresponding hydrochloride, preparation see Example 11) in 20 ml of dichloromethane was cooled to −10° C. 0.69 g of m-chloroperbenzoic acid was the added. The reaction mixture was kept at a temperature of −10° C. for 1 hour and allowed to react at room temperature for a further 45 minutes. To work up the reaction mixture it was extracted with 10 ml of saturated sodium bicarbonate solution, washed twice with 10 ml portions of water, dried and concentrated. The crude mixture containing the two abovementioned title compounds which remained as a residue was separated by chromatography on a small silica gel column. Using a toluene/ethanol 9:1 mixture, a fraction containing starting material was obtained. When the ethanol content of the eluent was increased to 100%, a fraction containing the monoxide was obtained, and by subsequent use of methanol as an eluent another fraction containing the dioxide was obtained. From the ethanolic fraction, 0.24 g of beige-colored monoxide having a melting point of 132° C. was obtained. From the methanolic fraction, 0.36 g of dioxide having a melting point of 126° C. was obtained.

EXAMPLE 29

5,6-Dihydro-2-methyl-8-methylamino-1-{2-[4-(4-methylpyridin-2-yl)piperazin-1-yl]ethyl}-4H-pyrrolo[3,2,1-ij]quinoline A) 44.5 g of 5,6-dihydro-2-methyl-8-nitro-4H-pyrrolo[3,2,1-ij]quinoline-1-acetic acid (preparation see Example 20 A) were heated under reflux for 1 hour in 450 ml of ethanol after addition of 8.63 ml of sulfuric acid. To work up the reaction mixture the ethanol was removed by evaporation, the residue was taken up in a mixture of water and dichloromethane, and the organic phase was separated, washed with water until neutral, dried and evaporated. Some diethyl ether was added to the oily crude product which remained as a residue, and the resulting precipitate was filtered out. 32.4 g of ethyl 5,6-dihydro-2-methyl-8-nitro-4H-pyrrolo[3,2,1-ij]quinoline-1-acetate were obtained as a greenish-ochre-colored powder.

B) 20 g of the product obtained above were dissolved in a mixture of 300 ml of ethanol and 100 ml of ethyl acetate. 3 g of a palladium/carbon catalyst (10% palladium on carbon) were then added and the reaction mixture was hydrogenated at a temperature of 50° C. using a hydrogen pressure of 4 bar. The catalyst was then filtered out, and the filtrate was evaporated to dryness. 20 g of crude product were obtained as a brownish oil. This was crystallized from diisopropyl ether and petroleum ether. 15.2 g of ethyl 5,6-dihydro-2-methyl-8-amino-4H-pyrrolo-[3,2,1-ij]quinoline-1-acetate were obtained as a dark brown powder.

C) 14 g of the product obtained above were heated under reflux for 2 hours with 2.84 g of formic acid in 150 ml of toluene. To work up the reaction mixture it was first washed with 75 ml of 10% strength aqueous sodium hydroxide solution, then with 100 ml of water, and then with 75 ml of 10% strength aqueous hydrochloric acid. After final washing with water to neutrality, it was dried and concentrated. A residue of 18 g of crude product remained, which was recrystallized from toluene. 11 g of ethyl 5,6-dihydro-2-methyl-8-formylamino-4H-pyrrolo[3,2,1-ij]quinoline-1-acetate obtained as a beige-colored powder.

D) 11 g of the product obtained above were added to 100 ml of ethanol, then a solution of 2.93 g of sodium hydroxide in 10 ml of water was added, and the reaction mixture was heated under reflux for 45 min. To work up the reaction mixture it was concentrated, the residue was taken up in water, and the mixture was acidified and extracted with dichloromethane. The dichloromethane extract was dried and concentrated. 1.73 g of 5,6-dihydro-2-methyl-8-formylamino-4H-pyrrolo[3,2,1-ij]quinoline acetic acid were obtained.

E) 1.7 g of the acid obtained above were heated under reflux for 2 hours with 1.61 g of carbonyldiimidazole in 20 ml of dichloromethane. 1.32 g of 1-(4-methylpyridin-2-yl)piper-azine were then added, and the reaction mixture was heated under reflux for a further 2 hours. To work up the reaction mixture it was washed with water, dried and concentrated. 3 g of crude 5,6-dihydro-2-methyl-8-formylamino-1-{2-[4-(4-methylpyridin-2-yl)piperazin-1-yl]-2-oxoethyl}-4H-pyrrolo-[3,2,1-ij]quinoline were obtained in the form of yellowish-brown platelets.

F) 0.79 g of lithium aluminum hydride were added to 30 ml of tetrahydrofuran cooled to 5°–10° C. The reaction mixture was allowed to warm to room temperature. A solution of 3 g of the product obtained above in 50 ml of tetrahydrofuran was then added. The reaction mixture was heated under reflux for 1 hour. It was then worked up as described in Example 13 C). 2.6 g of crude 5,6-dihydro-8-methylamino-2-methyl-1-{2-[4-(4-methylpyridin-2-yl) piperazin-1-yl]ethyl}-4H-pyrrolo[3,2,1-ij]quinoline were obtained as a brown oil.

For conversion to the corresponding tartrate, 1 g of the title base obtained above was dissolved in a little isopropanol. A solution of 0.375 g of tartaric acid in 1 ml of methanol was added to the solution. The resulting precipitate was filtered out. 0.85 g of 5,6-dihydro-8-methylamino-2-methyl-1-(2 -[4- (4-methylpyridin-2-yl) piperazin-1-yl]ethyl}-4H-pyrrolo[3,2,1-ij]quinoline tartrate 1 H$_2$O having a melting point of 140° C. was obtained.

EXAMPLE 30

5,6-Dihydro-2-methyl-8-dimethylamino-1-{2-[4-(4-methylpyridin-2-yl)piperazin-1-yl]ethyl}-4H-pyrrolo[3,2,1-ij]quinoline A) 0.5 g of 5,6-dihydro-2-methyl-8-methylamino-1-(2-[4-(4-methylpyridin-2-yl)piperazin-1-yl]ethyl}-4H-pyrrolo[3,2,1-ij]quinoline (preparation see Example 29) was heated under reflux for 3 hours with 0.07 g of formic acid in 5 ml of toluene. To work up the reaction mixture it was washed with water, dried and concentrated. 0.42 g of 5,6-dihydro-2-methyl-8-(N-formyl-N-methylamino)-1-{2-[4-(4-methylpyrrolo[3,2,1-ij]quinoline yl)piperazin-1-yl]ethyl}-4H-pyrrolo[3,2,1-ij]quinoline was obtained.

B) 0.08 g of lithium aluminum hydride was added to 10 ml of tetrahydrofuran cooled to a temperature of −5° to 0° C. The reaction mixture was allowed to warm to room temperature. A solution of 0.42 g of the product obtained above in tetrahydrofuran was then added. The reaction mixture was heated under reflux for 2 hours. It Was then worked up as described in Example 13 C). 0.37 g of crude 5,6-dihydro-2-methyl-8-dimethylamino-1-{2-[4-(4-methylpyridin-2-yl)-piperazin-1-yl]ethyl}-4H-pyrrolo[3,2,1-ij]quinoline was obtained as a brown oil. This title base was converted into the corresponding dihydrochloride as described in Example 13 C). 0.34 g of 5,6-dihydro-2-methyl-8-dimethylamino-1-{2-[4-(4-methylpyridin-2-yl)-piperazin-1-yl]ethyl}-4H-pyrrolo[3,2,1-ij]quinoline 2.1 HCl 0.1 H$_2$O was obtained as a brown powder having a melting point of 260° C.(decomposition).

EXAMPLE 31

4,5,6,7-Tetrahydro-2-methyl-1-{2-[4-(4-methylpyridin-2-y)piperazin-1-yl]ethyl}-pyrrolo[3,2,1-jk]benzazepine A) 43.86 g of α-tetralone were dissolved in 180 ml of ethanol. A solution of 104 g of hydroxylamine hydrochloride in 210 ml of water and then 168 ml of a 50% strength aqueous potassium hydroxide solution were added to the solution. The mixture was heated to boiling in a water bath for 15 minutes. The reaction mixture was then allowed to cool to room temperature. To work up the reaction mixture it was added to cold water and acidified with sulfuric acid. The resulting dark-yellow precipitate was filtered out and recrystallized from ethanol. 38.15 g of α-tetralone oxime was obtained as a white powder having a melting point of 101° C.

B) 30 ml of DIBAH (=1 molar solution of diisobutylaluminium hydride in hexane) were added dropwise under a nitrogen atmosphere to a solution of 1 g of tetralone oxime in 20 ml of dry dichloromethane cooled to 0° C. The reaction mixture was kept at 0° C. for 1 hour. The reaction mixture was then allowed to warm to room temperature, cooled to 0° C. again after 2 hours, diluted with 30 ml of dichloromethane to stop the reaction, and treated with vigorous stirring with 5.2 g of sodium fluoride and then 2 ml of water. The reaction mixture was vigorously stirred at 0° C. for a further 30 minutes. A whitish gelatinous material was formed. To work up the mixture it was filtered, the filter residue was washed again with dichloromethane, and the combined filtrates were evaporated. 0.80 g of crude 2,3,4,5-tetrahydrobenzo[b]-1H-azepine was obtained as a yellow oil.

C) A solution of 8.5 g of sodium nitrite in 20 ml of water was slowly added to a mixture of 17 ml of 12N hydrochloric acid, 50 g of ice and 15 g of the product obtained above, the temperature being kept below 5° C. The reaction mixture was kept at this temperature for 30 minutes. The reaction mixture was then allowed to warm to room temperature. After 1 hour, the reaction mixture was extracted with ethyl acetate. The organic phase was separated, washed with water, dried and evaporated. 17.88 g of crude 2,3,4,5-tetrahydro-1-nitrosobenz[b]-1H-azepine were obtained as a yellow-orange oil.

D) 17.5 g of the product obtained above were reduced as described in Example 1B) using 7.54 g of lithium aluminum hydride in tetrahydrofuran. The reaction mixture was worked up as described in Example IB). 14.6 g of 1-amino-2,3,4,5-tetrahydrobenz[b]-1H-azepine were obtained as an orange oil.

E) 4 g of the above product were heated under reflux at a temperature of 90° C. for 3 hours with 4.26 g of ethyl levulinate in a mixture of 36.66 ml of glacial acetic acid and 2.25 ml of 12 N hydrochloric acid. To work up the reaction mixture it was cooled, the organic solvent was removed by evaporation, the residue was taken up in water, and the mixture was extracted with dichloromethane. The dichloromethane phase was separated, washed with water, dried and evaporated. 2.67 g of crude ethyl 4,5,6,7-tetrahydro-2-methylpyrrolo[3,2,1-jk]benzazepine-1-acetate were obtained as a black oil.

F) 2.67 g of the above ester were dissolved in 40 ml of ethanol. A solution of 1.18 g of sodium hydroxide in 5 ml of water was added to the solution and the reaction mixture was heated under reflux (temperature about 78° C) for 1 hour. To work up the mixture the alcohol was evaporated, the residue was taken up in water, and the aqueous phase was washed with ethyl acetate and then adjusted to pH 1 by addition of hydrochloric acid. The acidified aqueous phase was again extracted with ethyl acetate, and the organic phase was separated, washed with water until neutral, dried and evaporated. 1.78 g of crude 4,5,6,7-tetrahydro-2-methyl-pyrrolo[3,2,1-jk]benzazepine-1-acetic acid were obtained as a brown oil.

G) 4.8 g of the above acid were reacted with 4.2 g of 1-(4-methylpyridin-2-yl)piperazine by the method described in Example 13B). The reaction mixture was tetrahydro-2-methyl-1-{2-[4-(4-methylpyridin-2-yl)piperazin-1-yl]-2-oxoethyl}-pyrrolo[3,2,1-jk)benzazepine were obtained as a green oil.

H) 6.5 g of the product obtained above were reduced in tetrahydrofuran as described in Example 13C) using 1.53 g of lithium aluminum hydride. The reaction mixture crude 4,5,6,7-tetrahydro-2-methyl-1-(2-[4-(4-methylpyridin-2-yl)piperazin-1-yl]ethyl}-pyrrolo-[3,2,1-jk]benzazepine were obtained.

The title base obtained above was converted into the corresponding hydrochloride by the method described in Example 13C). The resulting 4,5,6,7-tetrahydro-2-methyl-1-{2-[4-(4-methylpyridin-2-yl)piperazin-1-yl]ethyl}-pyrrolo[3,2,1-jk]benzazepine dihydrochloride 1 H₂O was obtained as a white powder (melting point >260° C).

EXAMPLE 32

2-Benzyl-5,6-dihydro-1-{2-[4-(4-methylpyridin-2-yl)-piperazin-1-yl]ethyl}-4H-pyrrolo[3,2,1-ij]quinoline A) 10 g of 1-amino-1,2,3,4-tetrahydroquinoline were dissolved in 100 ml of ethanol. 10.87 g of phenylacetone were added to the solution and the reaction mixture was heated under reflux for 5 hours and then kept at room temperature for 12 hours. To work up the reaction mixture it was concentrated to dryness, and the residue was purified by chromatography on a silica gel column using dichloromethane as the eluent. 14 g of crude 1-(1-benzylethylimino)-1,2,3,4-tetrahydroquinoline were obtained as an orange-colored oil.

B) A solution of 13 g of the product obtained above in 105.7 ml of dichloromethane was mixed with a solution of 2.1 g of phosphorus pentoxide in 70 g of methanesulfonic acid. The mixture was heated under reflux for 2 days and allowed to react at room temperature for a further 3 days. To work up the reaction mixture it was cooled and neutralized by addition of 280 ml of 2.5 N sodium hydroxide solution. The organic phase was separated, washed twice with 200 ml portions of water, dried and concentrated. The residue was purified by chromatography on a silica gel column using dichloromethane as the eluent. 4.5 g of crude 2-benzyl-5,6-dihydro-4H-pyrrolo[3,2,1-ij]quinoline were obtained as a yellow oil.

C) 2 g of the product obtained above were reacted in diethyl ether with 1.12 g of oxalyl chloride and then with 2.1 g of 1-(4-methylpyridin-2-yl)piperazine by the method described in Example 14C). The reaction mixture was worked up as described in Example 14C). 4.2 g of 2-benzyl-5,6-dihydro-1-{2-[4-(4-methylpyridin-2-yl)piperazin-1-yl]-1,2-dioxoethyl}-4H-pyrrolo[3,2,1-ij]quinoline were obtained.

D) 2.7 g of the product obtained above were dissolved in 15 ml of tetrahydrofuran, then 30 ml of a 1-molar solution of diborane in tetrahydrofuran were added to the solution under a nitrogen atmosphere, whereupon gas was evolved. The reaction mixture was heated under reflux for 3 hours. To work up the reaction mixture and destroy the diborane complex, the mixture was evaporated to dryness, the residue was taken up in 30 ml of 3 N hydrochloric acid, and the mixture was left at room temperature for 4 hours. It was then neutralized by addition of 10 ml of dilute sodium hydroxide solution and extracted with 100 ml of dichloromethane. The organic phase was washed twice with 100 ml portions of water, dried and evaporated. The same treatment was repeated twice more and the resulting crude product was then purified by chromatography on a silica gel column using toluene/ethanol 99:1. 0.9 g of crude 2-benzyl-5,6-dihydro-1-{2-[4-(4-methylpyridin-2-yl)piperazin-1-yl]ethyl}-4H-pyrrolo[3,2,1-ij]quinoline was obtained as a yellow oil.

The title base obtained above was converted into the corresponding hydrochloride as described in Example 13C). 1.5 g of 2-benzyl-5,6-dihydro-1-{2-[4-(4-methylpyridin-2-yl)-piperazin-1-yl]ethyl}-4H-pyrrolo[3,2,1-ij]quinoline.2.4 HCl 2 H₂O were obtained as a pale grey powder having a melting point of 186°-208° C.

The compounds of formula I shown in the following Table 1 can also be prepared by the processes described in the foregoing examples.

| Example No. | R¹ | R² | R³ | R⁴ | A | Z | B | D | R⁵ | Salt Form (H₂O) content in mol/mol | M.p. in °C. |
|---|---|---|---|---|---|---|---|---|---|---|---|
| 33 | H | H | CH₃ | CH₃ | bi | (CH₂)₂ | N | bi | 4-CH₃-pyrid-2 | 1.8 HCl (4.5) | 250 |
| 34 | H | H | CH₃ | H | CH₂ | (CH₂)₃ | N | bi | 4-F-phen | 1.5 HCl | 250 (z) |
| 35 | 7-Cl | H | CH₃ | H | O | (CH₂)₂ | N | bi | 4-CH₃-pyrid-2 | 2.7 HCl | 200 |
| 36 | H | H | CH₃ | H | CH₂ | (CH₂)₂ | N | bi | 4-F-phen | 1.7 HCl | 245 (z) |
| 37 | H | H | CH₃ | H | CH₂ | (CH₂)₂ | N | bi | pyrid-2 | Ba | 96 |
| 38 | H | H | CH₃ | phen | CH₂ | (CH₂)₂ | N | bi | 4-phen | Ba | 141 |
| 39 | H | H | CH₃ | n-C₄H₉ | CH₂ | (CH₂)₂ | N | bi | 4-phen | 1.2 HCl | >250 |
| 40 | H | H | phen | H | CH₂ | (CH₂)₂ | N | bi | 4-CH₃-pyrid-2 | 2 HCl (0.1) | 210 |
| 41 | 8-n-C₆H₁₃—CO | H | CH₃ | H | CH₂ | (CH₂)₂ | N | bi | 4-CH₃-pyrid-2 | 1 HCl | 215 |
| 42 | H | H | CH₃ | H | CH₂ | (CH₂)₂ | N | bi | 5-CH₃-pyrid-2 | 1 HCl (0.2) | >260 |
| 43 | H | H | CH₃ | H | CH₂ | (CH₂)₂ | N | bi | 5-Br-pyrid-2 | Ba | 239 |
| 44 | H | H | CH₃ | H | CH₂ | (CH₂)₂ | N | bi | 4-F-3-Cl-phen | Ba | 144 |
| 45 | H | H | 4-Cl-phen | H | CH₂ | (CH₂)₂ | CH | bi | phen | Ba | 108 |
| 46 | H | H | 4-F-phen | H | CH₂ | (CH₂)₂ | N | bi | 4-CH₃-pyrid-2 | Ba | 165 |
| 47 | H | H | CH₃ | H | CH₂ | (CH₂)₂ | N | bi | 4-CH₃-pyrid-2 | Ba | 142 |
| 48 | H | H | CH₃ | H | CH₂ | (CH₂)₂ | N | bi | 3-CH₃O-phen | Ba | 94 |
| 49 | H | H | CH₃ | H | CH₂ | (CH₂)₂ | N | bi | 4-CH₃O-phen | Ba | 114 |
| 50 | H | H | CH₃ | H | CH₂ | (CH₂)₂ | N | bi | 6-CH₃-pyrid-2 | Ba | 100 |
| 51 | H | H | CH₃ | H | CH₂ | (CH₂)₂ | N | bi | 3-CH₃-pyrid-2 | Ba | 98 |
| 52 | H | H | 4-Cl-phen | H | CH₂ | (CH₂)₂ | N | bi | pyrid-2 | 2 HCl (1.5) | 250 |
| 53 | H | H | CH₃ | H | bi | (CH₂)₂ | N | bi | 4-CH₃-pyrid-2 | 1 Fu | 194 |
| 54 | 8-CH₃ | H | CH₃ | H | CH₂ | (CH₂)₂ | N | bi | 4-CH₃-pyrid-2 | 2 HCl (1) | 232 |
| 55 | 8-CH₃ | H | CH₃ | H | CH₂ | (CH₂)₂ | CH | CO | 4-F-phen | 1 HCl (0.6) | 230 |
| 56 | H | H | CH₃ | H | CH—CH₃ | (CH₂)₂ | CH | CO | phen | 2 HCl (0.2) | 238 |
| 57 | H | H | CH₃ | H | CH—CH₃ | (CH₂)₂ | N | bi | 4-CH₃-pyrid-2 | 2 HCl (0.7) | 232 |
| 58 | H | H | CH₃ | CH₃ | CH₂ | (CH₂)₂ | N | bi | 4-CH₃-pyrid-2 | 2 HCl (2) | 190 |
| 59 | H | H | CH₃ | 4-CH₃—O-phen | CH₂ | (CH₂)₂ | N | bi | 4-CH₃-pyrid-2 | 2 HCl (1) | 240 |
| 60 | 8-(CH₃)₂CH—CO—NH | H | CH₃ | H | CH₂ | (CH₂)₂ | N | bi | 4-CH₃-pyrid-2 | 2.2 HCl (2.2) | >250 |
| 61 | H | H | CH₃ | 4-OH-phen | CH₂ | (CH₂)₂ | N | bi | 4-CH₃-pyrid-2 | ba | >242 |
| 62 | H | H | CH₃ | CH₂=CH—(CH₂)₂ | CH₂ | (CH₂)₂ | N | bi | 4-CH₃-pyrid-2 | 1.2 HCl | 148 |
| 63 | 8-CH₃O | H | CH₃ | n-C₄H₉ | CH₂ | (CH₂)₂ | N | bi | 4-CH₃-pyrid-2 | 2 HCl (1) | 178 |
| 64 | 8-OH | H | CH₃ | n-C₄H₉ | CH₂ | (CH₂)₂ | N | bi | 4-CH₃-pyrid-2 | Ba | 135 |
| 65 | 8-CH₃O | H | CH₃ | 4-CH₃O-phen | CH₂ | (CH₂)₂ | N | bi | 4-CH₃-pyrid-2 | 2 HCl | 125 |

-continued

| Example No. | R¹ | R² | R³ | R⁴ | A | Z | B | D | R⁵ | Salt Form (H₂O) content in mol/mol | M.p. in °C. |
|---|---|---|---|---|---|---|---|---|---|---|---|
| 66 | 8-phen-CO | H | CH₃ | H | CH₂ | (CH₂)₂ | N | bi | 4-CH₃-pyrid-2 | 2 HCl | 210 |
| 67 | 8-CH₃-CO | H | CH₃ | H | CH₂ | (CH₂)₂ | N | bi | 4-CH₃-pyrid-2 | 2 HCl | 258 |
| 68 | H | H | CH₃ | H | O | (CH₂)₂ | N | bi | 4-CH₃-pyrid-2 | Ba | 156 |
| 69 | H | H | CH₃ | H | S | (CH₂)₂ | N | bi | 4-F-phen | 1.3 HCl | 242 |
| 70 | 8-(CH₃)₃C—CO | H | CH₃ | H | CH₂ | (CH₂)₂ | N | bi | 4-CH₃-pyrid-2 | 2 HCl (1) | 260 |
| 71 | 8-Cin | H | CH₃ | H | CH₂ | (CH₂)₂ | N | bi | 4-CH₃-pyrid-2 | 1.3 HCl (1.2) | 215 |
| 72 | H | H | CH₃ | H | CH₂ | CH—CH₂—CH₃ | N | bi | 4-CH₃-pyrid-2 | 1.8 HCl (0.9) | 180 |
| 73 | H | H | CH₃ | n-C₄H₉ | CH₂ | (CH₂)₂ | N | bi | 4-CH₃-pyrid-2 | 1.1 Fu (0.1) | 166 |
| 74 | H | H | CH₃ | H | CH—CH₃ | (CH₂)₂ | N | bi | 4-CH₃-pyrid-2 | 2 HCl (0.7) | 232 |
| 75 | 8-CH₃O | H | CH₃ | n-C₄H₉ | CH₂ | (CH₂)₂ | N | bi | 4-CH₃-pyrid-2 | 2 HCl (1) | 178 |
| 76 | 8-OH | H | CH₃ | n-C₄H₉ | CH₂ | (CH₂)₂ | N | bi | 4-CH₃-pyrid-2 | Ba | 135 |
| 77 | 8-phen-CH₂ | H | CH₃ | H | CH₂ | (CH₂)₂ | N | bi | 4-CH₃-pyrid-2 | Ba (0.4) | 152 |
| 78 | 8-CH₃—S | H | CH₃ | H | S | (CH₂)₂ | N | bi | 4-CH₃-pyrid-2 | 1.8 HCl (1) | 203–211 |
| 79 | 7-Cl | 9-Cl | CH₃ | H | O | (CH₂)₂ | N | bi | 4-CH₃-pyrid-2 | Ba | 174 |
| 80 | 8-CH₃NH | H | CH₃ | H | CH₂ | (CH₂)₂ | N | bi | 4-CH₃-pyrid-2 | 2.5 HTA (4) | 140 |
| 81 | 8-(CH₃)₂N | H | CH₃ | H | CH₂ | (CH₂)₂ | N | bi | 4-CH₃-pyrid-2 | 2.4 HCl (4) | 215–260 (Z) |
| 82 | 8-(4-Cl-phen)CO | H | CH₃ | H | CH₂ | (CH₂)₂ | N | bi | 4-CH₃-pyrid-2 | Ba (1.3) | 110 |
| 83 | 8-cyh-CO | H | CH₃ | H | CH₂ | (CH₂)₂ | N | bi | 4-CH₃-pyrid-2 | 2.1 HCl (1) | 195 |
| 84 | 8-cyh-CH₂ | H | CH₃ | H | CH₂ | (CH₂)₂ | N | bi | 4-CH₃-pyrid-2 | 2 HCl (1.5) | 243 |
| 85 | H | H | cyh | H | CH₂ | —CH—CH₂—<br>\|<br>OH | N | bi | 4-CH₃-pyrid-2 | Ba | 160 |
| 86 | H | H | 4-CH₃-phen | H | CH₂ | (CH₂)₂ | N | bi | 4-CH₃-pyrid-2 | Ba | 67 |
| 87 | H | H | CH₃ | cyh | CH₂ | (CH₂)₂ | N | bi | 4-CH₃-pyrid-2 | 2 HCl (0.7) | 180 |
| 88 | 8-(CH₃)₂—CH—CO | H | CH₃ | H | (CH₂)₂ | (CH₂)₂ | N | bi | 4-CH₃-pyrid-2 | 2 HCl (1) | 248–252 |

-continued

| Example No. | R¹ | R² | R³ | R⁴ | A | Z | B | D | R⁵ | Salt Form (H₂O) content in mol/mol | M.p. in °C. |
|---|---|---|---|---|---|---|---|---|---|---|---|
| 89 | 9-(CH₃)₂CH—CH—OH | H | CH₃ | H | S | (CH₂)₂ | N | bi | 4-CH₃-pyrid-2 | Ba | 100 |
| 90 | 7-(CH₃)₂CH—CH—OH | H | CH₃ | H | S | (CH₂)₂ | N | bi | 4-CH₃-pyrid-2 | Ba | 100 |
| 91 | 7-(CH₃)₂CH—CO | H | CH₃ | H | S | (CH₂)₂ | N | bi | 4-CH₃-pyrid-2 | 2.1 HCl (2.3) | 200-240 |
| 92 | (4-OH-phen)-CO | H | CH₃ | n-C₄H₉ | CH₂ | (CH₂)₂ | N | bi | 4-CH₃-pyrid-2 | Ba | 119 |
| 93 | (4-OH-phen)-CO | H | CH₃ | n-C₄H₉ | CH₂ | (CH₂)₂ | N | bi | 4-CH₃-pyrid-2 | Ba | 147 |
| 94 | 8-(CH₃)₂CH—CO | H | CH₃ | H | CH₂ | (CH₂)₂ | N | bi | 4-F-phen | Ba | 144-145 |
| 95 | 8-(CH₃)₂CH—CO | H | CH₃ | H | CH₂ | (CH₂)₂ | N | bi | 5-CH₃-pyrid-2 | 2 HCl | >250 |
| 96 | H | H | 4-CH₃O-phen | H | CH₂ | (CH₂)₂ | N | bi | 4-CH₃-pyrid-2 | Ba | 120-123 |
| 97 | H | H | 4-OH-phen | H | CH₂ | (CH₂)₂ | N | bi | 4-CH₃-pyrid-2 | Ba | 278-284 | pyrid-2 = pyrid-2-yl  bi = Bond  phen = phenyl  cyh = cyclohexyl  HCl = Hydrochloride  Ba = base  cin = cinnamoyl  HTA = Hydrogentartrate  z = Decomposition  Fu = Fumarate

EXAMPLE I

Tablets containing 5,6-dihydro-2-methyl-1-{2-[4-(4-methylpyridin-2-yl)piperazin-1-yl]-ethyl}4H-pyrrolo-[3,2,1-ij]quinoline Tablets were prepared having the following composition per tablet:

| | |
|---|---|
| 5,6-Dihydro-2-methyl-1-{2-[4-(4-methyl-pyridin-2-yl)-piperazin-1-yl]ethyl}-4H-pyrrolo[3,2,1-ij]-quinoline | 20 mg |
| Maize starch | 60 mg |
| Lactose | 135 mg |
| Gelatin (as a 10% strength solution) | 6 mg |

The active substance, the maize starch and the lactose were thickened with the 10% strength gelatin solution. The paste was comminuted, and the resulting granules were transferred to a suitable sheet and dried at 45° C. The dried granules were passed through a comminutor and mixed with the following further auxiliaries in a mixer:

| | |
|---|---|
| Talc | 5 mg |
| Magnesium stearate | 5 mg |
| Maize starch | 9 mg | ps and then compressed to give 240 mg tablets.

The foregoing description and examples have been set forth merely to illustrate the invention and are not intended to be limiting. Since modifications of the described embodiments incorporating the spirit and substance of the invention may occur to persons skilled in the art, the scope of the invention should be limited solely with reference to the appended claims and equivalents.

What is claimed is:

1. A compound corresponding to the formula I

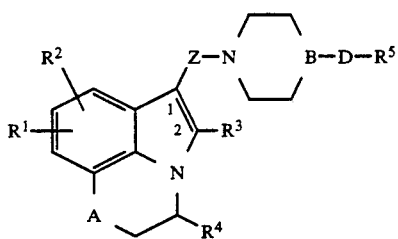

wherein $R^1$ denotes hydrogen, lower alkoxy, lower alkylthio, hydroxyl, halogen, trifluoromethyl, nitro, amino, lower mono- or dialkylamino, $C_1$-$C_7$-alkyl which may be substituted by hydroxyl, or denotes a phenyl-lower alkyl group which may be substituted in the phenyl ring by lower alkyl, lower alkoxy, hydroxyl or halogen, or denotes $C_3$-$C_6$-cycloalkyl, $C_4$-$C_7$-cycloalkylalkyl, $C_3$-$C_7$-alkenyl, $C_2$-$C_7$-alkanoyl, lower alkanoyloxy, lower alkanoylamino, a benzoyl, benzoyloxy or benzoylamino group whose phenyl ring may be substituted by lower alkyl, lower alkoxy, hydroxyl or halogen, or denotes a cinnamoyl, cinnamoyloxy or cinnamoylamino group whose phenyl ring may be substituted by lower alkyl, lower alkoxy, hydroxyl or halogen;

$R^2$ denotes hydrogen, halogen, lower alkyl or, if $R^1$ is not hydroxyl or a hydroxyphenyl-containing group, $R^2$ may also denote lower alkoxy;

$R^3$ denotes hydrogen, lower alkyl which may be substituted by hydroxyl, or denotes lower alkenyl, $C_3$-$C_6$-cycloalkyl, $C_4$-$C_7$-cycloalkylalkyl or a phenyl or phenyl-lower alkyl group, which may be substituted in the phenyl ring by lower alkyl, halogen, lower alkoxy, hydroxyl or hydroxyalkoxy, but where $R^3$ can only contain a free hydroxyl group if $R^1$ does not contain a carbonyloxy group;

$R^4$ denotes hydrogen, $C_1$-$C_7$-alkyl which may be substituted by hydroxyl, or denotes $C_3$-$C_7$-alkenyl, $C_3$-$C_6$-cycloalkyl, $C_4$-$C_7$-cycloalkylalkyl or a phenyl or phenyl-lower alkyl group which may be substituted in the phenyl ring by lower alkyl, halogen, lower alkoxy, hydroxyl or hydroxyalkoxy but where $R^4$ can only contain a free hydroxyl group if R does not contain a carbonyloxy group;

A denotes an alkylene chain having 1-2 carbon atoms, which may be substituted by lower alkyl, or denotes a bond;

Z denotes an alkylene chain having 2-4 carbon atoms, which may be substituted by lower alkyl or, if $R^1$ does not contain a carbonyloxy group, also by hydroxyl;

B denotes nitrogen or the CH group;

$R^5$ denotes a pyridyl or phenyl radical which may be substituted by lower alkyl, lower alkoxy or halogen, and D represents a bond or, if B denotes the CH group and $R^5$ denotes a phenyl radical which may be substituted as described above, D may also represent a CO group, and its acid addition salts.

2. A compound according to claim 1, wherein $R^1$ denotes hydrogen, $C_1$-$C_6$-alkyl which may be substituted by hydroxyl, or denotes halogen, hydroxyl, lower alkoxy, lower alkanoyl, lower alkanoyloxy, lower alkanoylamino, or a benzoyl, benzoyloxy, benzoylamino, cinnamoyl, cinnamoyloxy or cinnamoylamino group which may be substituted by lower alkyl, lower alkoxy or halogen in the phenyl ring.

3. A compound according to claim wherein $R^2$ denotes hydrogen.

4. A compound according to claim 1, wherein $R^3$ denotes lower alkyl.

5. A compound according to claim 1, wherein A denotes a methylene group which may be substituted by lower alkyl.

6. A compound according to claim 1, wherein Z denotes an ethylene chain which may be substituted by hydroxyl or lower 7. A compound according to claim 1, wherein $R^5$ denotes a pyridyl radical which may be substituted by lower alkyl, lower alkoxy or halogen.

8. A compound according to claim 7, wherein $R^4$ is a 4-methylpyrid-2-yl radical.

9. A pharmaceutical composition comprising an effective anti-inflammatory or anti-allergic amount of a compound according to claim 1 and at least one pharmaceutical carrier or adjuvant.

10. A compound corresponding to the formula IV

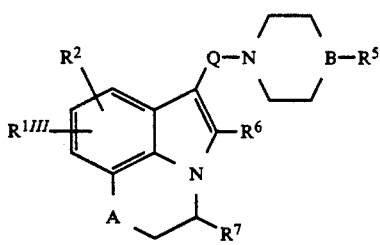

IV in which
- R$^{1III}$ denotes hydrogen, lower alkoxy, lower alkylthio, hydroxyl, halogen, trifluoromethyl, nitro, amino, lower mono- or dialkylamino, C$_1$-C$_7$-alkyl, a phenyl-lower alkyl group which may be substituted in the phenyl ring by lower alkyl, lower alkoxy, hydroxyl or halogen, or denotes C$_3$-C$_6$-cycloalkyl, C$_4$-C$_7$-cycloalkylalkyl, C$_3$-C$_7$-alkenyl, C$_2$-C$_7$-alkanoyl, a benzoyl or cinnamoyl group whose phenyl ring may be substituted by lower alkyl, lower alkoxy, hydroxyl or halogen, or denotes an N-formyl-substituted or N-lower alkanoyl-substituted amino or lower alkylamino group,
- R$^2$ denotes hydrogen, halogen, lower alkyl or, if R$^{1III}$ is not hydroxyl or a hydroxyphenyl-containing group, also denotes lower alkoxy,
- R$^6$ denotes hydrogen, lower alkyl which may be substituted by hydroxyl, or denotes lower alkenyl, C$_3$-C$_6$-cycloalkyl, C$_4$-C$_7$-cycloalkylalkyl or a phenyl or phenyl-lower alkyl group which may be substituted in the phenyl ring by lower alkyl, halogen, lower alkoxy, hydroxyl or hydroxyalkoxy, or denotes a lower alkoxycarbonyl or lower alkoxycarbonyl-lower alkyl group or a phenyl or phenyl-lower alkyl group substituted in the phenyl ring by lower alkoxycarbonyl-lower alkoxy,
- R$^7$ denotes hydrogen, C$_1$-C$_7$-alkyl which may be substituted by hydroxyl, or denotes C$_3$-C$_7$-alkenyl, C$_3$-C$_6$-cycloalkyl, C$_4$-C$_7$-cycloalkylalkyl or a phenyl or phenyl-lower alkyl group which may be substituted in the phenyl ring by lower alkyl, halogen, lower alkoxy, hydroxyl or hydroxyalkoxy, or denotes a lower alkoxycarbonyl or lower alkoxycarbonyl-lower alkoxy group or a phenyl or phenyl-lower alkyl group substituted in the phenyl ring by lower alkoxycarbonyl-lower alkoxy,
- A denotes an alkylene chain having 1-2 carbon atoms, which is optionally substituted by lower alkyl, or denotes a bond,
- B denotes nitrogen or the CH group,
- R$^5$ denotes a pyridyl or phenyl radical which is optionally substituted by lower alkyl, lower alkoxy or halogen, and
- Q represents a —Q'—CO chain, in which Q' represents an alkylene chain having 1-3 carbon atoms, which may be substituted by lower alkyl or by oxo, or Q denotes an alkylene chain having 2-4 carbon atoms substituted in the position adjacent to the indole structure by oxo, and which may be substituted by lower alkyl, or, if R$^{1III}$, R$^6$ and/or R$^7$ denote a CO-containing radical, Q can also denote an alkylene chain having 2-4 carbon atoms, which may be substituted by lower alkyl or in the position adjacent to the indole structure also by hydroxyl.

* * * * *